United States Patent
Abokitse et al.

(10) Patent No.: US 10,227,575 B2
(45) Date of Patent: *Mar. 12, 2019

(54) MULTI-DOMAIN ENZYMES HAVING CUTINASE ACTIVITY, COMPOSITIONS COMPRISING SAME AND USES THEREOF

(71) Applicants: OZYMES, Trois-Rivieres (CA); NATIONAL RESEARCH COUNCIL OF CANADA, Ottawa (CA)

(72) Inventors: Kofi Abokitse, Quebec (CA); Peter C. K. Lau, Kirkland (CA); Stephan Grosse, Longueuil (CA)

(73) Assignees: Ozymes, Tois-Rivières, Quebec (CA); National Research Council of Canada, Ottawa, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/673,065

(22) Filed: Aug. 9, 2017

(65) Prior Publication Data
US 2017/0335298 A1    Nov. 23, 2017

Related U.S. Application Data

(63) Continuation of application No. 15/044,715, filed on Feb. 16, 2016, now Pat. No. 9,752,131.

(60) Provisional application No. 62/116,761, filed on Feb. 16, 2015.

(51) Int. Cl.
| | |
|---|---|
| *C11D 3/39* | (2006.01) |
| *C11D 3/43* | (2006.01) |
| *C11D 7/50* | (2006.01) |
| *C12N 9/16* | (2006.01) |
| *C12N 9/18* | (2006.01) |
| *C12N 9/96* | (2006.01) |
| *C07K 19/00* | (2006.01) |
| *C09K 8/582* | (2006.01) |
| *C11D 3/386* | (2006.01) |
| *A23K 20/189* | (2016.01) |

(52) U.S. Cl.
CPC .............. *C12N 9/18* (2013.01); *A23K 20/189* (2016.05); *C07K 19/00* (2013.01); *C09K 8/582* (2013.01); *C11D 3/38636* (2013.01); *C11D 3/38681* (2013.01); *C11D 3/39* (2013.01); *C11D 3/43* (2013.01); *C11D 7/5004* (2013.01); *C12N 9/16* (2013.01); *C12N 9/96* (2013.01); *C12Y 301/01074* (2013.01); *C07K 2319/00* (2013.01); *C07K 2319/036* (2013.01); *C07K 2319/20* (2013.01)

(58) Field of Classification Search
None
See application file for complete search history.

(56) References Cited

U.S. PATENT DOCUMENTS

| | | |
|---|---|---|
| 7,985,569 B2 | 7/2011 | Aehle et al. |
| 2010/0029538 A1 | 2/2010 | Auterinen et al. |
| 2014/0031272 A1 | 1/2014 | Shipovskov et al. |
| 2014/0187468 A1 | 7/2014 | Estell et al. |
| 2015/0017700 A1 | 1/2015 | Estell et al. |
| 2015/0191607 A1 | 7/2015 | McDaniel |

FOREIGN PATENT DOCUMENTS

| | | |
|---|---|---|
| WO | WO 1990009446 | 8/1990 |
| WO | WO 198009367 | 12/1998 |
| WO | WO 2008039353 | 4/2008 |
| WO | WO 2009155115 | 12/2009 |

OTHER PUBLICATIONS

Abt B. et al., "Complete genome sequence of Cellulomonas flavigena type strain (134)", Cutinase [Cellulomonas flavigena DSM 20109], GenBank: ADG75999.1, Jan. 28, 2014.

Bagwell CE et al., "Survival in Nuclear Waste, Extreme Resistance, and Potential Applications Gleaned from the Genome Sequence of Kineococcus radiotolerans SRS30216" PLoS ONE, Dec. 2008, vol. 3, issue 12, e3878.

Bligh, E.G. and W.J. Dyer, "A rapid method for total lipid extraction and purification", Canadian Journal of Biochemistry and Physiology, Aug. 1959, p. 911-917, vol. 37.

Chen F. et al., "Genome sequencing of Cellulomonas bogoriensis 69B4", Cutinase [Cellulomonas bogoriensis 69B4 = DSM 16987], GenBank: KGM14008.1, Oct. 16, 2014.

Chen F. et al., "Genome sequencing of Cellulomonas bogoriensis 69B4", Cutinase [Cellulomonas bogoriensis 69B4 = DSM 16987], GenBank: KGM14009.1, Oct. 16, 2014.

Copeland A. et al., "Complete sequence of chromosome of Kineococcus radiotolerans SRS30216" Kineococcus radiotolerans SRS30216, complete genome, GenBank, NCBI Ref. Seq.: NC_009664.2, Jul. 31, 2015.

Copeland A. et al., "Complete sequence of chromosome of kineococcus radiotolerans SRS30216", Cutinase [Kineococcus radiotolerans SRS30216 = ATCC BAA-149],GenBank: ABS05574.1, Jan. 28, 2014.

Gerard H.C. et al., "Evaluation of cutinase activity of various industrial lipases", Biotechnol. Appl. Biochem, 1993, pp. 181-189, vol. 17.

Kallio H. et al., "Cutin composition of five Finnish berries", Journal of Agricultural and Food Chemistry, 2006, pp. 457-462. vol. 54.

Kasuya K. et al., "Substrate and binding specificities of bacterial polyhydroxybutyrate depolymerases", International Journal of Biological Macromolecules, 1999, pp. 329-336, vol. 24.

(Continued)

*Primary Examiner* — Iqbal H Chowdhury

(74) *Attorney, Agent, or Firm* — Knobbe, Martens, Olson & Bear, LLP

(57) ABSTRACT

An isolated chimeric recombinant protein has cutinase activity. The protein includes a cutinase catalytic domain and a polymer binding domain operably linked by a proline/threonine-rich linker domain. The proline/threonine-rich linker domain includes at least 50% proline or threonine residues over a stretch of 15 to 55 consecutive amino acids.

20 Claims, 13 Drawing Sheets

Specification includes a Sequence Listing.

(56) References Cited

OTHER PUBLICATIONS

Kim Y.-H. et al., "Uniqueness of microbial cutinases in hydrolysis of p-nitrophenyl esters", Journal of Microbiology and Biotechnology, 2003, pp. 57-63, vol. 13(1).

Martinez C. et al. "Fusarium solani cutinase is a lipolytic enzyme with a catalytic serine accessible to solvent", Nature, Apr. 16, 1992, pp. 615-618, vol. 356.

Phillips R.W. et al., "*Kineococcus radiotolerans* sp. nov., a radiation-resistant, Gram-positive bacterium", International Journal of Systematic and Evolutionary Microbiology, 2002, pp. 933-938, vol. 52.

Smith P. K. et al., "Measurement of protein using bicinchoninic acid", Analytical Biochemistry, 1985, pp. 76-85, vol. 150.

Soliday C.L. et al., "Cloning and structure determination of cDNA for cutinase, an enzyme involved in fungal penetration of plants", Proc. Natl. Acad. Sci. USA, Jul. 1984, pp. 3939-3943, vol. 81.

Tamura K. et al., "MEGA4: Molecular Evolutionary Genetics Analysis (MEGA) software version 4.0.", Mol. Biol. Evol., 2007, pp. 1596-1599, vol. 24(8).

Verma D. et al., "Heterogeneity among Homologs of Cutinase-Like Protein Cut5 in Mycobacteria", PLOS ONE, DOL:10.1371, Journal.pone.0133186, Jul. 15, 2015.

Wang P. et al., "Combined use of mild oxidation and cutinase/lipase pretreatments for enzymatic processing of wool fabrics", Eng. Life. Sci., 2010, pp. 19-25, vol. 10.

Wang, G. and Zhuang, W., "Direct Submission", Hypothetical protein Q760_05675 [Cellulomonas cellasea DSM 20118], GenBank: KGM03336.1. Oct. 16, 2014.

Xiao Z. et al., "Improvement of the thermostability and activity of a pectate lyase by single amino acid substitutions, using a strategy based on melting-temperature-guided sequence alignment", Applied and Environmental Microbiology, Feb. 2008, pp. 1183-1189, vol. 74.

Zhang G. et al., "Extracellular accumulation of recombinant proteins fused to the carrier protein YebF in *Escherichia coli*", Nature Biotechnology, Jan. 2006, pp. 100-104, vol. 24.

```
CLUSTAL 2.1 multiple sequence alignment

KrCUT    -ATCSDVDVVFARGTGETPGLGVVGGPFVRSLTGELSDRTVTSHAVDYAASSSQASAGPG
CcCUT    APACADVEVLFARGTGEAPGLGVLGTPFVRSVTSALSDRTVTSYAVNYAAESSQRSAGPG
CfCUT    APACPDVELVFARGTGEAAGLGIVGRPLERALAAELPGRTVVATAVDYAASSSQASAGPG
CbCUT2   AGSCPDVQVVFARGTGERAGLGIIGRPFARALADELPGMTVTSHAVDYAAAASQRSAGPG
CbCUT1   TGDCPDVHVVFARGTGEPRGLGIVGRPFVSDLGDALPTMTVTSYAVNYSANASQTSAGPG
         *.**.:.*******  ***.:*  *:      *.  **.: **:*:*  :** *****

KrCUT    ATAMSAHVREVAAACPSTRFVLGGYSQGATVTDIALGIRTGTTTGTPVPAELAGRVAAVV
CcCUT    ATDLTNHLTATAAACPGTRFVLGGYSQGATVVDLALGIRTGTTTGTAIPAALEPRVAAIV
CfCUT    SGDMVAKVRSRAAACPGTQFVLGGYSQGATVTDLALGIRTGVTAGTALPEDLAARVAAVV
CbCUT2   ATAMTDHVTAMAARCPGTQFVLGGYSQGATVTSIALGIRAGTTTGRAIPDELSDRVAAVV
CbCUT1   AGDMTSHVTSMAARCPGTQFVLGGYSQGATVTSIAVGARSTSIRSRVLPANLEPRVAAVV
         :   :  ::  **  **.*:*********...:*.*;     .  :*   * ****:*

KrCUT    VFGNPLGLSGRTIATASSTYGPKSKDYCNSSDSVCGSAPKTGTGGHLSYASNGSTTDGAR
CcCUT    VFGNPLGISGRTIATASPTYAARARDFCATGDPVCGGG--SSFAAHLAYRTNGDVTAGAD
CfCUT    VYGNPLGLTRRTIAQAAPAFATRTVEYCNAGDPVCEPGG-GRFTAHITYATNGTVLEGAR
CbCUT2   VFGNPLGMRGQTIASASRTYADRAKDYCNSGDSICGRQPSTGRGTHTGYATNGSTTDGAR
CbCUT1   VFGNPLGLTRRTIASEAPAYAAKSRDYCNRSDTVCGGR-GDAPGGHLAYVSNGSVADGAA
         *:*****:  :***     :  :::  ::  ::*   .*.:*      *  *  :**   .  **

KrCUT    FAAGLVRAAGTPT-------------------------TPTPTPTPTPVP-TTCVRDSTR
CcCUT    FAAGLARATTVPVPTPTVPGTPTPSPTAPGTPTPVPTTSPTPAPSPTAPG-AACVRASTR
CfCUT    FAAARVTAPAPTP------------------TPGPTGTPAPVPSAEPTPAPGDTCVTASSL
CbCUT2   FAAGLVTANPPEA---------------------APPTAPPTTPPTTPAPPSDQVTCVTAQVS
CbCUT1   FAASLVGVAP--------------------------------------GDPASCVTARAV
         ***.  ..                                         :**

KrCUT    DHVAADRAVSLYGRAYARGSRDSLGATSSYNVVSLQQVEGG-WRLVTAC
CcCUT    AHVEAGRAERRHGIAYATGSGDRIGWVSSFVRVSVQQTADG-WERVLSC
CfCUT    QHVRDGRAYPLWMRTYARGSGDPLGVLSSRTVVSLQADGTDTWRKVAAC
CbCUT2   EHVEARRAIRGLTRAYARGTLEDIGRLRSTEEVSLRRSGTFSWTPTASC
CbCUT1   DHVEADRAFRSVLRAYARGSRDPLGRLTSSDLVSLQRTGQDSWSVVPAC
         **  **    :**  *: : :*   *    **::       *   .  :*
```

B.

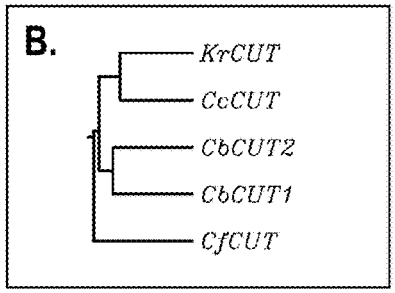

SEQUENCE LISTING

```
<160> NUMBER OF SEQ ID NOS: 69

<210> SEQ ID NO 1
<211> LENGTH: 294
<212> TYPE: PRT
<213> ORGANISM: Kineococcus radiotolerans
<220> FEATURE:
<221> NAME/KEY: MISC_FEATURE
<222> LOCATION: (1)..(194)
<223> OTHER INFORMATION: Full-length ssKrCUT

<400> SEQUENCE: 1

Met Leu Arg Ala Arg Pro Ser His Arg Leu Ala Ser Ala Ala Ala Val
1               5                   10                  15

Val Ala Ala Thr Gly Ala Ala Leu Leu Ala Gly Ser Ser Pro Ala Ala
            20                  25                  30

Ala Ala Thr Cys Ser Asp Val Asp Val Val Phe Ala Arg Gly Thr Gly
        35                  40                  45

Glu Thr Pro Gly Leu Gly Val Val Gly Gly Pro Phe Val Arg Ser Leu
    50                  55                  60

Thr Gly Glu Leu Ser Asp Arg Thr Val Thr Ser His Ala Val Asp Tyr
65                  70                  75                  80

Ala Ala Ser Ser Ser Gln Ala Ser Ala Gly Pro Gly Ala Thr Ala Met
                85                  90                  95

Ser Ala His Val Arg Glu Val Ala Ala Ala Cys Pro Ser Thr Arg Phe
            100                 105                 110

Val Leu Gly Gly Tyr Ser Gln Gly Ala Thr Val Thr Asp Ile Ala Leu
        115                 120                 125

Gly Ile Arg Thr Gly Thr Thr Thr Gly Thr Pro Val Pro Ala Glu Leu
    130                 135                 140

Ala Gly Arg Val Ala Ala Val Val Val Phe Gly Asn Pro Leu Gly Leu
145                 150                 155                 160

Ser Gly Arg Thr Ile Ala Thr Ala Ser Ser Thr Tyr Gly Pro Lys Ser
                165                 170                 175

Lys Asp Tyr Cys Asn Ser Ser Asp Ser Val Cys Gly Ser Ala Pro Lys
            180                 185                 190

Thr Gly Thr Gly Gly His Leu Ser Tyr Ala Ser Asn Gly Ser Thr Thr
        195                 200                 205

Asp Gly Ala Arg Phe Ala Ala Gly Leu Val Arg Ala Ala Gly Thr Pro
    210                 215                 220

Thr Thr Pro Thr Pro Thr Pro Thr Pro Thr Pro Val Pro Thr Thr Cys
225                 230                 235                 240

Val Arg Asp Ser Thr Arg Asp His Val Ala Ala Asp Arg Ala Val Ser
                245                 250                 255
```

```
Leu Tyr Gly Arg Ala Tyr Ala Arg Gly Ser Arg Asp Ser Leu Gly Ala
            260                 265                 270

Thr Ser Ser Tyr Asn Val Val Ser Leu Gln Gln Val Glu Gly Gly Trp
        275                 280                 285

Arg Leu Val Thr Ala Cys
        290

<210> SEQ ID NO 2
<211> LENGTH: 189
<212> TYPE: PRT
<213> ORGANISM: Kineococcus radiotolerans
<220> FEATURE:
<221> NAME/KEY: MISC_FEATURE
<222> LOCATION: (1)..(189)
<223> OTHER INFORMATION: KrCUT catalytic domain (KrCUT189)

<400> SEQUENCE: 2

Ala Thr Cys Ser Asp Val Asp Val Val Phe Ala Arg Gly Thr Gly Glu
1               5                   10                  15

Thr Pro Gly Leu Gly Val Val Gly Gly Pro Phe Val Arg Ser Leu Thr
            20                  25                  30

Gly Glu Leu Ser Asp Arg Thr Val Thr Ser His Ala Val Asp Tyr Ala
        35                  40                  45

Ala Ser Ser Ser Gln Ala Ser Ala Gly Pro Gly Ala Thr Ala Met Ser
    50                  55                  60

Ala His Val Arg Glu Val Ala Ala Ala Cys Pro Ser Thr Arg Phe Val
65                  70                  75                  80

Leu Gly Gly Tyr Ser Gln Gly Ala Thr Val Thr Asp Ile Ala Leu Gly
                85                  90                  95

Ile Arg Thr Gly Thr Thr Thr Gly Thr Pro Val Pro Ala Glu Leu Ala
            100                 105                 110

Gly Arg Val Ala Ala Val Val Val Phe Gly Asn Pro Leu Gly Leu Ser
        115                 120                 125

Gly Arg Thr Ile Ala Thr Ala Ser Ser Thr Tyr Gly Pro Lys Ser Lys
    130                 135                 140

Asp Tyr Cys Asn Ser Ser Asp Ser Val Cys Gly Ser Ala Pro Lys Thr
145                 150                 155                 160

Gly Thr Gly Gly His Leu Ser Tyr Ala Ser Asn Gly Ser Thr Thr Asp
                165                 170                 175

Gly Ala Arg Phe Ala Ala Gly Leu Val Arg Ala Ala Gly
            180                 185

<210> SEQ ID NO 3
<211> LENGTH: 17
<212> TYPE: PRT
<213> ORGANISM: Kineococcus radiotolerans
<220> FEATURE:
<221> NAME/KEY: MISC_FEATURE
<222> LOCATION: (1)..(17)
<223> OTHER INFORMATION: Threonine/proline-rich linker domain of KrCUT

<400> SEQUENCE: 3

Thr Pro Thr Thr Pro Thr Pro Thr Pro Thr Pro Thr Pro Val Pro Thr
1               5                   10                  15

Thr

<210> SEQ ID NO 4
<211> LENGTH: 55
<212> TYPE: PRT
<213> ORGANISM: Kineococcus radiotolerans
```

<220> FEATURE:
<221> NAME/KEY: MISC_FEATURE
<222> LOCATION: (1)..(55)
<223> OTHER INFORMATION: polymer-binding domain of KrCUT

<400> SEQUENCE: 4

Cys Val Arg Asp Ser Thr Arg Asp His Val Ala Ala Asp Arg Ala Val
1               5                   10                  15

Ser Leu Tyr Gly Arg Ala Tyr Ala Arg Gly Ser Arg Asp Ser Leu Gly
            20                  25                  30

Ala Thr Ser Ser Tyr Asn Val Val Ser Leu Gln Gln Val Glu Gly Gly
        35                  40                  45

Trp Arg Leu Val Thr Ala Cys
    50                  55

<210> SEQ ID NO 5
<211> LENGTH: 786
<212> TYPE: DNA
<213> ORGANISM: Artificial Sequence
<220> FEATURE:
<223> OTHER INFORMATION: polynucleotide encoding KrCUT optimized for
      expression in E. coli

<400> SEQUENCE: 5
gcgacttgca gtgacgtcga tgtggttttc gcgcgtggca ctggtgaaac gccgggcctg      60
ggcgttgtgg gaggaccgtt tgtgcgttct ttaaccggcg aattaagcga tcgtaccgtg     120
acaagccatg cggttgacta tgcagccagt agttcccagg ctagcgctgg tccgggtgca     180
acggcaatgt ctgcccacgt ccgcgaagta gctgccgcct gcccgtcgac ccgttttgtt     240
ctgggtggtt attcgcaagg tgcaacggtt acagacatcg ccttagggat acgtaccggt     300
accaccaccg gtactcctgt accggccgaa ctggcgggcc gcgttgcagc tgttgtggtc     360
tttggaaatc cgctgggtct gtcaggacgt actattgcta ccgcgtcatc tacgtatggt     420
ccgaaatcca aagattactg taattcttca gattcagtgt gcggctccgc cccgaaaacc     480
ggcacaggcg gtcatctgtc atacgcgagt aatggttcta ccactgatgg tgctcgtttt     540
gcagcgggac ttgtccgtgc agccggtacg cctaccaccc cgaccccgac gccgacccct     600
acgccggttc ctaccacatg tgtacgtgat tcgacacgcg atcatgtggc cgccgatcgt     660
gcggtatcat tatatggccg cgcttatgct agaggatctc gcgattccct gggcgctact     720
agctcttaca acgtggtgag cctgcaacag gtcgaggggg gttggcgctt ggtaactgct     780
tgttga                                                                786

<210> SEQ ID NO 6
<211> LENGTH: 261
<212> TYPE: PRT
<213> ORGANISM: Kineococcus radiotolerans
<220> FEATURE:
<221> NAME/KEY: MISC_FEATURE
<222> LOCATION: (1)..(261)
<223> OTHER INFORMATION: KrCUT (lacking residues 1-33 of ssKrCUT)

<400> SEQUENCE: 6

Ala Thr Cys Ser Asp Val Asp Val Val Phe Ala Arg Gly Thr Gly Glu
1               5                   10                  15

Thr Pro Gly Leu Gly Val Val Gly Gly Pro Phe Val Arg Ser Leu Thr
            20                  25                  30

Gly Glu Leu Ser Asp Arg Thr Val Thr Ser His Ala Val Asp Tyr Ala
        35                  40                  45

```
Ala Ser Ser Gln Ala Ser Ala Gly Pro Gly Ala Thr Ala Met Ser
    50              55                  60
Ala His Val Arg Glu Val Ala Ala Cys Pro Ser Thr Arg Phe Val
 65              70              75                  80
Leu Gly Gly Tyr Ser Gln Gly Ala Thr Val Thr Asp Ile Ala Leu Gly
                 85              90                  95
Ile Arg Thr Gly Thr Thr Thr Gly Thr Pro Val Pro Ala Glu Leu Ala
                100             105                 110
Gly Arg Val Ala Ala Val Val Phe Gly Asn Pro Leu Gly Leu Ser
             115             120             125
Gly Arg Thr Ile Ala Thr Ala Ser Ser Thr Tyr Gly Pro Lys Ser Lys
             130             135             140
Asp Tyr Cys Asn Ser Ser Asp Ser Val Cys Gly Ser Ala Pro Lys Thr
145             150             155                 160
Gly Thr Gly Gly His Leu Ser Tyr Ala Ser Asn Gly Ser Thr Thr Asp
                 165             170                 175
Gly Ala Arg Phe Ala Ala Gly Leu Val Arg Ala Ala Gly Thr Pro Thr
            180             185                 190
Thr Pro Thr Pro Thr Pro Thr Pro Thr Pro Val Pro Thr Thr Cys Val
         195             200             205
Arg Asp Ser Thr Arg Asp His Val Ala Ala Asp Arg Ala Val Ser Leu
         210             215             220
Tyr Gly Arg Ala Tyr Ala Arg Gly Ser Arg Asp Ser Leu Gly Ala Thr
225             230             235                 240
Ser Ser Tyr Asn Val Val Ser Leu Gln Gln Val Glu Gly Gly Trp Arg
                245             250             255
Leu Val Thr Ala Cys
            260

<210> SEQ ID NO 7
<211> LENGTH: 366
<212> TYPE: DNA
<213> ORGANISM: Artificial Sequence
<220> FEATURE:
<223> OTHER INFORMATION: YebF coding sequence (minus stop codon)
<220> FEATURE:
<221> NAME/KEY: misc_feature
<222> LOCATION: (1)..(366)
<223> OTHER INFORMATION: YebF coding sequence

<400> SEQUENCE: 7
atggagaaaa acatgaaaaa aagaggggcg ttttagggc tgttgttggt ttctgcctgc      60
gcatcagttt tcgctgccaa taatgaaacc agcaagtcgg tcactttccc aaagtgtgaa    120
gatctggatg ctgccggaat tgccgcgagc gtaaaacgtg attatcaaca aaatcgcgtg    180
gcgcgttggg cagatgatca aaaaattgtc ggtcaggccg atcccgtggc ttgggtcagt    240
ttgcaggaca ttcagggtaa agatgataaa tggtcagtac cgctaaccgt gcgtggtaaa    300
agtgccgata ttcattacca ggtcagcgtg gactgcaaag cgggaatggc ggaatatcag    360
cggcgt                                                               366

<210> SEQ ID NO 8
<211> LENGTH: 122
<212> TYPE: PRT
<213> ORGANISM: Artificial Sequence
<220> FEATURE:
<223> OTHER INFORMATION: YebF amino acid sequence
<220> FEATURE:
<221> NAME/KEY: MISC_FEATURE
```

<222> LOCATION: (1)..(122)
<223> OTHER INFORMATION: YebF

<400> SEQUENCE: 8

```
Met Glu Lys Asn Met Lys Lys Arg Gly Ala Phe Leu Gly Leu Leu Leu
1               5                   10                  15
Val Ser Ala Cys Ala Ser Val Phe Ala Ala Asn Asn Glu Thr Ser Lys
            20                  25                  30
Ser Val Thr Phe Pro Lys Cys Glu Asp Leu Asp Ala Ala Gly Ile Ala
        35                  40                  45
Ala Ser Val Lys Arg Asp Tyr Gln Gln Asn Arg Val Ala Arg Trp Ala
    50                  55                  60
Asp Asp Gln Lys Ile Val Gly Gln Ala Asp Pro Val Ala Trp Val Ser
65                  70                  75                  80
Leu Gln Asp Ile Gln Gly Lys Asp Asp Lys Trp Ser Val Pro Leu Thr
                85                  90                  95
Val Arg Gly Lys Ser Ala Asp Ile His Tyr Gln Val Ser Val Asp Cys
            100                 105                 110
Lys Ala Gly Met Ala Glu Tyr Gln Arg Arg
        115                 120
```

<210> SEQ ID NO 9
<211> LENGTH: 1152
<212> TYPE: DNA
<213> ORGANISM: Artificial Sequence
<220> FEATURE:
<223> OTHER INFORMATION: polynucleotide encoding YebF-KrCUT
<220> FEATURE:
<221> NAME/KEY: misc_feature
<222> LOCATION: (1)..(1152)
<223> OTHER INFORMATION: cDNA encoding YebF-KrCUT

<400> SEQUENCE: 9

```
atggagaaaa acatgaaaaa aagaggggcg ttttagggc tgttgttggt ttctgcctgc      60
gcatcagttt tcgctgccaa taatgaaacc agcaagtcgg tcactttccc aaagtgtgaa    120
gatctggatg ctgccggaat tgccgcgagc gtaaaacgtg attatcaaca aaatcgcgtg    180
gcgcgttggg cagatgatca aaaaattgtc ggtcaggccg atcccgtggc ttgggtcagt    240
ttgcaggaca ttcagggtaa agatgataaa tggtcagtac cgctaaccgt gcgtggtaaa    300
agtgccgata ttcattacca ggtcagcgtg gactgcaaag cgggaatggc ggaatatcag    360
cggcgtgcga cttgcagtga cgtcgatgtg gttttcgcgc gtggcactgg tgaaacgccg    420
ggcctgggcg ttgtgggagg accgtttgtg cgttctttaa ccggcgaatt aagcgatcgt    480
accgtgacaa gccatgcggt tgactatgca gccagtagtt cccaggctag cgctggtccg    540
ggtgcaacgg caatgtctgc ccacgtccgc gaagtagctg ccgcctgccc gtcgacccgt    600
tttgttctgg gtggttattc gcaaggtgca acggttacag acatcgcctt agggatacgt    660
accggtacca ccaccggtac tcctgtaccg gccgaactgg cgggccgcgt tgcagctgtt    720
gtggtctttg gaaatccgct gggtctgtca ggacgtacta ttgctaccgc gtcatctacg    780
tatggtccga aatccaaaga ttactgtaat tcttcagatt cagtgtgcgg ctccgccccg    840
aaaaccggca caggcggtca tctgtcatac gcgagtaatg gttctaccac tgatggtgct    900
cgttttgcag cgggacttgt ccgtgcagcc ggtacgccta ccaccccgac cccgacgccg    960
accccctacgc cggttcctac cacatgtgta cgtgattcga cacgcgatca tgtggccgcc   1020
gatcgtgcgg tatcattata tggccgcgct atgctagag atctcgcga ttccctgggc     1080
```

```
gctactagct cttacaacgt ggtgagcctg caacaggtcg aggggggttg gcgcttggta    1140
actgcttgtt ga                                                        1152
```

<210> SEQ ID NO 10
<211> LENGTH: 383
<212> TYPE: PRT
<213> ORGANISM: Artificial Sequence
<220> FEATURE:
<223> OTHER INFORMATION: amino acid sequence of YebF-KrCUT

<400> SEQUENCE: 10

```
Met Glu Lys Asn Met Lys Lys Arg Gly Ala Phe Leu Gly Leu Leu Leu
1               5                   10                  15

Val Ser Ala Cys Ala Ser Val Phe Ala Ala Asn Asn Glu Thr Ser Lys
            20                  25                  30

Ser Val Thr Phe Pro Lys Cys Glu Asp Leu Asp Ala Ala Gly Ile Ala
        35                  40                  45

Ala Ser Val Lys Arg Asp Tyr Gln Gln Asn Arg Val Ala Arg Trp Ala
    50                  55                  60

Asp Asp Gln Lys Ile Val Gly Gln Ala Asp Pro Val Ala Trp Val Ser
65                  70                  75                  80

Leu Gln Asp Ile Gln Gly Lys Asp Lys Trp Ser Val Pro Leu Thr
                85                  90                  95

Val Arg Gly Lys Ser Ala Asp Ile His Tyr Gln Val Ser Val Asp Cys
            100                 105                 110

Lys Ala Gly Met Ala Glu Tyr Gln Arg Arg Ala Thr Cys Ser Asp Val
        115                 120                 125

Asp Val Val Phe Ala Arg Gly Thr Gly Glu Thr Pro Gly Leu Gly Val
    130                 135                 140

Val Gly Gly Pro Phe Val Arg Ser Leu Thr Gly Glu Leu Ser Asp Arg
145                 150                 155                 160

Thr Val Thr Ser His Ala Val Asp Tyr Ala Ala Ser Ser Ser Gln Ala
                165                 170                 175

Ser Ala Gly Pro Gly Ala Thr Ala Met Ser Ala His Val Arg Glu Val
            180                 185                 190

Ala Ala Ala Cys Pro Ser Thr Arg Phe Val Leu Gly Gly Tyr Ser Gln
        195                 200                 205

Gly Ala Thr Val Thr Asp Ile Ala Leu Gly Ile Arg Thr Gly Thr Thr
    210                 215                 220

Thr Gly Thr Pro Val Pro Ala Glu Leu Ala Gly Arg Val Ala Ala Val
225                 230                 235                 240

Val Val Phe Gly Asn Pro Leu Gly Leu Ser Gly Arg Thr Ile Ala Thr
                245                 250                 255

Ala Ser Ser Thr Tyr Gly Pro Lys Ser Lys Asp Tyr Cys Asn Ser Ser
            260                 265                 270

Asp Ser Val Cys Gly Ser Ala Pro Lys Thr Gly Thr Gly His Leu
        275                 280                 285

Ser Tyr Ala Ser Asn Gly Ser Thr Thr Asp Gly Ala Arg Phe Ala Ala
    290                 295                 300

Gly Leu Val Arg Ala Ala Gly Thr Pro Thr Thr Pro Thr Pro Thr Pro
305                 310                 315                 320

Thr Pro Thr Pro Val Pro Thr Thr Cys Val Arg Asp Ser Thr Arg Asp
                325                 330                 335

His Val Ala Ala Asp Arg Ala Val Ser Leu Tyr Gly Arg Ala Tyr Ala
            340                 345                 350
```

Arg Gly Ser Arg Asp Ser Leu Gly Ala Thr Ser Ser Tyr Asn Val Val
         355                 360                 365

Ser Leu Gln Gln Val Glu Gly Gly Trp Arg Leu Val Thr Ala Cys
         370                 375                 380

<210> SEQ ID NO 11
<211> LENGTH: 936
<212> TYPE: DNA
<213> ORGANISM: Artificial Sequence
<220> FEATURE:
<223> OTHER INFORMATION: polynucleotide encoding YebF-KrCUT189

<400> SEQUENCE: 11

```
atggagaaaa acatgaaaaa aagaggggcg tttttagggc tgttgttggt ttctgcctgc     60
gcatcagttt tcgctgccaa taatgaaacc agcaagtcgg tcactttccc aaagtgtgaa   120
gatctggatg ctgccggaat tgccgcgagc gtaaaacgtg attatcaaca aaatcgcgtg   180
gcgcgttggg cagatgatca aaaaattgtc ggtcaggccg atcccgtggc ttgggtcagt   240
ttgcaggaca ttcagggtaa agatgataaa tggtcagtac cgctaaccgt gcgtggtaaa   300
agtgccgata tcattacca ggtcagcgtg gactgcaaag cgggaatggc ggaatatcag   360
cggcgtgcga cttgcagtga cgtcgatgtg gttttcgcgc gtggcactgg tgaaacgccg   420
ggcctgggcg ttgtgggagg accgtttgtg cgttctttaa ccggcgaatt aagcgatcgt   480
accgtgacaa gccatgcggt tgactatgca gccagtagtt cccaggctag cgctggtccg   540
ggtgcaacgg caatgtctgc ccacgtccgc gaagtagctg ccgcctgccc gtcgacccgt   600
tttgttctgg gtggttattc gcaaggtgca acggttacag acatcgcctt agggatacgt   660
accggtacca ccaccggtac tcctgtaccg gccgaactgg cgggccgcgt tgcagctgtt   720
gtggtctttg gaaatccgct gggtctgtca ggacgtacta ttgctaccgc gtcatctacg   780
tatggtccga aatccaaaga ttactgtaat tcttcagatt cagtgtgcgg ctccgccccg   840
aaaaccggca caggcggtca tctgtcatac gcgagtaatg gttctaccac tgatggtgct   900
cgttttgcag cgggacttgt ccgtgcagcc ggttga                              936
```

<210> SEQ ID NO 12
<211> LENGTH: 311
<212> TYPE: PRT
<213> ORGANISM: Artificial Sequence
<220> FEATURE:
<223> OTHER INFORMATION: amino acid sequence of YebF-KrCUT189

<400> SEQUENCE: 12

Met Glu Lys Asn Met Lys Lys Arg Gly Ala Phe Leu Gly Leu Leu Leu
1               5                   10                  15

Val Ser Ala Cys Ala Ser Val Phe Ala Ala Asn Asn Glu Thr Ser Lys
            20                  25                  30

Ser Val Thr Phe Pro Lys Cys Glu Asp Leu Asp Ala Ala Gly Ile Ala
        35                  40                  45

Ala Ser Val Lys Arg Asp Tyr Gln Gln Asn Arg Val Ala Arg Trp Ala
    50                  55                  60

Asp Asp Gln Lys Ile Val Gly Gln Ala Asp Pro Val Ala Trp Val Ser
65                  70                  75                  80

Leu Gln Asp Ile Gln Gly Lys Asp Asp Lys Trp Ser Val Pro Leu Thr
                85                  90                  95

Val Arg Gly Lys Ser Ala Asp Ile His Tyr Gln Val Ser Val Asp Cys
            100                 105                 110

```
Lys Ala Gly Met Ala Glu Tyr Gln Arg Arg Ala Thr Cys Ser Asp Val
        115                 120                 125

Asp Val Val Phe Ala Arg Gly Thr Gly Glu Thr Pro Gly Leu Gly Val
130                 135                 140

Val Gly Gly Pro Phe Val Arg Ser Leu Thr Gly Glu Leu Ser Asp Arg
145                 150                 155                 160

Thr Val Thr Ser His Ala Val Asp Tyr Ala Ala Ser Ser Gln Ala
                165                 170                 175

Ser Ala Gly Pro Gly Ala Thr Ala Met Ser Ala His Val Arg Glu Val
            180                 185                 190

Ala Ala Ala Cys Pro Ser Thr Arg Phe Val Leu Gly Gly Tyr Ser Gln
        195                 200                 205

Gly Ala Thr Val Thr Asp Ile Ala Leu Gly Ile Arg Thr Gly Thr Thr
    210                 215                 220

Thr Gly Thr Pro Val Pro Ala Glu Leu Ala Gly Arg Val Ala Ala Val
225                 230                 235                 240

Val Val Phe Gly Asn Pro Leu Gly Leu Ser Gly Arg Thr Ile Ala Thr
                245                 250                 255

Ala Ser Ser Thr Tyr Gly Pro Lys Ser Lys Asp Tyr Cys Asn Ser Ser
        260                 265                 270

Asp Ser Val Cys Gly Ser Ala Pro Lys Thr Gly Thr Gly His Leu
            275                 280                 285

Ser Tyr Ala Ser Asn Gly Ser Thr Thr Asp Gly Ala Arg Phe Ala Ala
        290                 295                 300

Gly Leu Val Arg Ala Ala Gly
305                 310

<210> SEQ ID NO 13
<211> LENGTH: 303
<212> TYPE: PRT
<213> ORGANISM: Cellulomonas flavigena

<400> SEQUENCE: 13

Met Gln Val Thr Pro Thr Arg Arg Thr Leu Ala Gly Val Val Ala Ala
1               5                   10                  15

Val Ala Ala Leu Ala Ser Val Thr Thr Leu Ala Thr Gly Ala Ser Ala
            20                  25                  30

Ala Pro Ala Cys Pro Asp Val Glu Leu Val Phe Ala Arg Gly Thr Gly
        35                  40                  45

Glu Ala Ala Gly Leu Gly Ile Val Gly Arg Pro Leu Glu Arg Ala Leu
    50                  55                  60

Ala Ala Glu Leu Pro Gly Arg Thr Val Ala Thr Ala Val Asp Tyr
65                  70                  75                  80

Ala Ala Ser Ser Ser Gln Ala Ser Ala Gly Pro Gly Ser Gly Asp Met
                85                  90                  95

Val Ala Lys Val Arg Ser Arg Ala Ala Cys Pro Gly Thr Gln Phe
            100                 105                 110

Val Leu Gly Gly Tyr Ser Gln Gly Ala Thr Val Thr Asp Leu Ala Leu
        115                 120                 125

Gly Ile Arg Thr Gly Val Thr Ala Gly Thr Ala Pro Glu Asp Leu
    130                 135                 140

Ala Ala Arg Val Ala Ala Val Val Val Tyr Gly Asn Pro Leu Gly Leu
145                 150                 155                 160

Thr Arg Arg Thr Ile Ala Gln Ala Ala Pro Ala Phe Ala Thr Arg Thr
```

```
                            165                 170                 175
Val Glu Tyr Cys Asn Ala Gly Asp Pro Val Cys Glu Pro Gly Gly Gly
            180                 185                 190

Arg Phe Thr Ala His Ile Thr Tyr Ala Thr Asn Gly Thr Val Leu Glu
            195                 200                 205

Gly Ala Arg Phe Ala Ala Arg Val Thr Ala Pro Ala Pro Thr Pro
            210                 215                 220

Thr Pro Gly Pro Thr Gly Thr Pro Ala Pro Val Pro Ser Ala Glu Pro
225                 230                 235                 240

Thr Pro Ala Pro Gly Asp Thr Cys Val Thr Ala Ser Ser Leu Gln His
                245                 250                 255

Val Arg Asp Gly Arg Ala Tyr Pro Leu Trp Met Arg Thr Tyr Ala Arg
            260                 265                 270

Gly Ser Gly Asp Pro Leu Gly Val Leu Ser Ser Arg Thr Val Val Ser
            275                 280                 285

Leu Gln Ala Asp Gly Thr Asp Thr Trp Arg Lys Val Ala Ala Cys
            290                 295                 300
```

<210> SEQ ID NO 14
<211> LENGTH: 293
<212> TYPE: PRT
<213> ORGANISM: Cellulomonas bogoriensis
<400> SEQUENCE: 14

```
Met Ser Ile Thr Pro Gly Gly Arg Lys Val Ala Ala Leu Ile Thr
1               5                   10                  15

Thr Ala Ala Leu Thr Ser Thr Ala Ala Ile Ala Thr Pro Ala Thr Ala
            20                  25                  30

Ala Ala Pro Val Ala Gly Pro Val Ala Thr Ser Thr Gly Asp Cys Pro
            35                  40                  45

Asp Val His Val Val Phe Ala Arg Gly Thr Gly Glu Pro Arg Gly Leu
        50                  55                  60

Gly Ile Val Gly Arg Pro Phe Val Ser Asp Leu Gly Asp Ala Leu Pro
65                  70                  75                  80

Thr Met Thr Val Thr Ser Tyr Ala Val Asn Tyr Ser Ala Asn Ala Ser
                85                  90                  95

Gln Thr Ser Ala Gly Pro Gly Ala Gly Asp Met Thr Ser His Val Thr
            100                 105                 110

Ser Met Ala Ala Arg Cys Pro Gly Thr Gln Phe Val Leu Gly Gly Tyr
            115                 120                 125

Ser Gln Gly Ala Thr Val Thr Ser Ile Ala Val Gly Ala Arg Ser Thr
130                 135                 140

Ser Ile Arg Ser Arg Val Leu Pro Ala Asn Leu Glu Pro Arg Val Ala
145                 150                 155                 160

Ala Val Val Val Phe Gly Asn Pro Leu Gly Leu Thr Arg Arg Thr Ile
                165                 170                 175

Ala Ser Glu Ala Pro Ala Tyr Ala Ala Lys Ser Arg Asp Tyr Cys Asn
            180                 185                 190

Arg Ser Asp Thr Val Cys Gly Gly Arg Gly Asp Ala Arg Gly His
            195                 200                 205

Leu Ala Tyr Val Ser Asn Gly Ser Val Ala Asp Gly Ala Ala Phe Ala
        210                 215                 220

Ala Ser Leu Val Gly Val Ala Pro Gly Asp Pro Ala Ser Cys Val Thr
225                 230                 235                 240
```

```
Ala Arg Ala Val Asp His Val Glu Ala Asp Arg Ala Phe Arg Ser Val
            245                 250                 255

Leu Arg Ala Tyr Ala Arg Gly Ser Arg Asp Pro Leu Gly Arg Leu Thr
        260                 265                 270

Ser Ser Asp Leu Val Ser Leu Gln Arg Thr Gly Gln Asp Ser Trp Ser
        275                 280                 285

Val Val Pro Ala Cys
        290

<210> SEQ ID NO 15
<211> LENGTH: 331
<212> TYPE: PRT
<213> ORGANISM: Cellulomonas cellasea

<400> SEQUENCE: 15

Met His Gln Leu Thr Pro Pro Ala Ala Pro Ser Arg Pro Arg Ala Ala
1               5                   10                  15

Arg Arg Pro Arg Arg Leu Leu Ala Ala Ala Leu Ala Leu Ala Ala Thr
            20                  25                  30

Ser Gly Ala Leu Ser Thr Leu Ala Ala Pro Thr Ala Val Ala Ala Pro
        35                  40                  45

Ala Cys Ala Asp Val Glu Val Leu Phe Ala Arg Gly Thr Gly Glu Ala
    50                  55                  60

Pro Gly Leu Gly Val Leu Gly Thr Pro Phe Val Arg Ser Val Thr Ser
65                  70                  75                  80

Ala Leu Ser Asp Arg Thr Val Thr Ser Tyr Ala Val Asn Tyr Ala Ala
                85                  90                  95

Glu Ser Ser Gln Arg Ser Ala Gly Pro Gly Ala Thr Asp Leu Thr Asn
            100                 105                 110

His Leu Thr Ala Thr Ala Ala Cys Pro Gly Thr Arg Phe Val Leu
        115                 120                 125

Gly Gly Tyr Ser Gln Gly Ala Thr Val Val Asp Leu Ala Leu Gly Ile
        130                 135                 140

Arg Thr Gly Thr Thr Thr Gly Thr Ala Ile Pro Ala Ala Leu Glu Pro
145                 150                 155                 160

Arg Val Ala Ala Ile Val Val Phe Gly Asn Pro Leu Gly Ile Ser Gly
                165                 170                 175

Arg Thr Ile Ala Thr Ala Ser Pro Thr Tyr Ala Ala Arg Ala Arg Asp
            180                 185                 190

Phe Cys Ala Thr Gly Asp Pro Val Cys Gly Gly Ser Ser Phe Ala
        195                 200                 205

Ala His Leu Ala Tyr Arg Thr Asn Gly Asp Val Thr Ala Gly Ala Asp
    210                 215                 220

Phe Ala Gly Leu Arg Ala Thr Thr Pro Val Pro Thr Pro
225                 230                 235                 240

Thr Val Pro Gly Thr Pro Thr Pro Ser Pro Thr Ala Pro Gly Thr Pro
                245                 250                 255

Thr Pro Val Pro Thr Thr Ser Pro Thr Pro Ala Pro Ser Pro Thr Ala
            260                 265                 270

Pro Gly Ala Ala Cys Val Arg Ala Ser Thr Arg Ala His Val Glu Ala
        275                 280                 285

Gly Arg Ala Glu Arg Arg His Gly Ile Ala Tyr Ala Thr Gly Ser Gly
    290                 295                 300

Asp Arg Ile Gly Trp Val Ser Ser Phe Val Arg Val Ser Val Gln Gln
305                 310                 315                 320
```

Thr Ala Asp Gly Trp Glu Arg Val Leu Ser Cys
            325                 330

<210> SEQ ID NO 16
<211> LENGTH: 222
<212> TYPE: PRT
<213> ORGANISM: Amycolatopsis sp. ATCC 39116

<400> SEQUENCE: 16

Met Val His Asn Arg Leu Arg Lys Leu Thr Leu Leu Ala Cys Ala Val
1               5                   10                  15

Val Gly Leu Ala Gly Thr Ala Thr Val Gly Thr Ala Ser Gly Ala Thr
            20                  25                  30

Ser Ala Ala Cys Ser Asp Leu Glu Ile Val Phe Ala Arg Gly Ser
        35                  40                  45

Gly Glu Ala Pro Gly Leu Gly Ile Thr Gly Thr Pro Leu Val Ser Asp
    50                  55                  60

Val Lys Ser Ala Leu Ser Ser Ala Ser Val Ser Ser Tyr Ala Val Asp
65                  70                  75                  80

Tyr Ala Ala Ser Tyr Asp Gln Thr Ser Ala Gly Pro Gly Ala Thr Asp
                85                  90                  95

Met Ser Asn His Ile Lys Ser Thr Ala Ala Ala Cys Pro Asp Thr Lys
            100                 105                 110

Phe Ala Ile Gly Gly Tyr Ser Gln Gly Ala Ser Val Thr Asp Ile Ala
        115                 120                 125

Ile Gly Ile Arg Thr Tyr Leu Gly Thr Gly Gln Thr Ile Pro Thr Glu
    130                 135                 140

Leu Ala Pro Arg Val Val Ala Val Ile Ala Phe Gly Asn Pro Leu Gly
145                 150                 155                 160

Leu Tyr Gly Gln Thr Ile Lys Thr Ala Ser Pro Thr Tyr Gly Pro Lys
                165                 170                 175

Ser Leu Glu Phe Cys Asn Arg Gly Asp Asn Val Cys Gly Gly Thr Gly
            180                 185                 190

Thr Gly Pro Gly Tyr Gly His Leu Ser Tyr Ala Arg Asp Gly Ser Val
        195                 200                 205

Asp Gln Ala Ala Ala Phe Ile Ala Lys Gln Tyr Asn Ala Ser
    210                 215                 220

<210> SEQ ID NO 17
<211> LENGTH: 219
<212> TYPE: PRT
<213> ORGANISM: Frankia sp. BMG5.12

<400> SEQUENCE: 17

Met Arg Leu Ala Arg Ser Trp Lys Gln Arg Ala Val Ala Val Phe Leu
1               5                   10                  15

Thr Ala Val Ala Gly Thr Leu Gly Ala Gly Ile Thr Ala Ser Pro Val
            20                  25                  30

Ser Ala Ala Thr Cys Ser Asp Val Asp Val Val Phe Ala Arg Gly Ser
        35                  40                  45

Gly Glu Leu Pro Gly Leu Gly Ile Thr Gly Thr Pro Phe Val Asn Ser
    50                  55                  60

Val Lys Gln Gly Leu Thr Gly Lys Thr Val Ser Ser Tyr Ala Val Asn
65                  70                  75                  80

Tyr Ala Ala Asp Ile Ala Gln Thr Ser Asp Gly Ala Gly Ala Thr Asp
                85                  90                  95

-continued

Met Thr Arg His Val Arg Ser Val Ala Ala Ser Cys Pro Asn Thr Lys
            100                 105                 110

Phe Val Leu Gly Gly Tyr Ser Gln Gly Ala Ser Val Thr Asp Ile Ser
        115                 120                 125

Ile Gly Ile Arg Thr Phe Leu Gly Ser Gly Glu Thr Ile Pro Thr Glu
    130                 135                 140

Leu Ala Pro Arg Val Ala Ala Val Val Phe Gly Asn Pro Leu Ala
145                 150                 155                 160

Leu Phe Gly Gln Lys Ile Thr Thr Ala Ser Pro Leu Tyr Gly Pro Lys
                165                 170                 175

Ala Lys Glu Phe Cys Asn Leu Gly Asp Pro Val Cys Ala Gly Gly Phe
            180                 185                 190

Asn Val Phe Ala His Leu Thr Tyr Gly Phe Asp Gly Ser Thr Ala Asn
        195                 200                 205

Gly Ala Ser Phe Ala Val Ser Lys Val Arg Ala
    210                 215

<210> SEQ ID NO 18
<211> LENGTH: 228
<212> TYPE: PRT
<213> ORGANISM: Actinoplanes missouriensis

<400> SEQUENCE: 18

Met Asn Lys Arg Arg Lys Arg Asn Val Ala Thr Val Gly Ile Cys Ala
1               5                   10                  15

Ala Val Val Ala Ala Gly Ala Val Ile Thr Pro Gln Ala Phe Ala Gly
            20                  25                  30

Thr Leu Phe Gly Gly Arg Ala Thr Thr Ala Ala Gly Asp Cys Ser Asp
        35                  40                  45

Val Glu Leu Val Phe Ala Arg Gly Thr Gly Glu Pro Gln Gly Leu Gly
    50                  55                  60

Ile Val Gly Arg Pro Leu Ala Arg Glu Leu Ala Ala Ala Leu Pro Asp
65                  70                  75                  80

Leu Ala Val Gly Ser Phe Ala Val Val Tyr Ala Ala Ala Gly Asn Gln
                85                  90                  95

Arg Ser Ala Gly Pro Gly Ala Thr Asn Met Ser Arg His Ile Thr Glu
            100                 105                 110

Val Ala Gly Glu Cys Pro Asp Thr Arg Phe Val Ile Gly Gly Tyr Ser
        115                 120                 125

Gln Gly Ala Ser Val Thr Asp Ile Ala Ile Gly Ile Arg Gly Ala Gly
    130                 135                 140

Thr Ala Gly Glu Ala Ile Pro Glu Arg Leu Ala Asp Arg Val Ala Ala
145                 150                 155                 160

Val Val Val Phe Gly Asn Pro Leu Gly Leu Gln Arg Arg Thr Ile Ala
                165                 170                 175

Gly Ser Ser Ala Val Phe Gly Pro Lys Ala Lys Glu Phe Cys Asn Thr
            180                 185                 190

Gly Asp Pro Val Cys Gly Gly Gly Asn Phe Ala Ala His Leu Ala
        195                 200                 205

Tyr Pro Arg Asn Gly Ser Val Gln Gln Ala Ala Phe Ala Ala Ser
    210                 215                 220

Lys Ile Ala Gly
225

<210> SEQ ID NO 19
<211> LENGTH: 218
<212> TYPE: PRT
<213> ORGANISM: Cryptosporangium arvum

<400> SEQUENCE: 19

Met Ser Val Leu Leu Thr Val Arg Arg Val Val Thr Ala Val Ala Leu
1               5                   10                  15

Thr Ala Thr Gly Leu Thr Gly Ile Ala Phe Ala Ala Ser Pro Ala Thr
            20                  25                  30

Ala Ala Cys Ser Asp Val Gln Val Val Phe Ala Arg Gly Ser Thr Glu
        35                  40                  45

Ala Pro Gly Leu Gly Ile Leu Gly Arg Pro Leu Val Ser Ala Val Gln
    50                  55                  60

Gln Gln Leu Pro Gly Leu Thr Val Asp Ser Tyr Ala Val Asp Tyr Ala
65                  70                  75                  80

Ala Asn Val Ser Gln Thr Ser Ala Gly Pro Gly Ala Thr Asp Met Ser
                85                  90                  95

Asp His Ile Thr Glu Val Ala Ala Arg Cys Pro Asp Thr Glu Phe Val
            100                 105                 110

Ile Gly Gly Tyr Ser Gln Gly Ala Ser Val Thr Asp Ile Ala Ile Gly
        115                 120                 125

Ile Arg Thr Thr Leu Gly Arg Gly Gly Thr Ile Pro Glu Asn Leu Ala
    130                 135                 140

Pro Arg Ile Lys Ala Val Thr Val Phe Gly Asn Pro Leu Arg Leu Ser
145                 150                 155                 160

Arg Gln Thr Ile Asn Ser Ala Ser Gln Leu Tyr Gly Arg Lys Ala Ile
                165                 170                 175

Asp Ile Cys Ala Thr Gly Asp Pro Val Cys Gly Asn Gly Ala Asn Ala
            180                 185                 190

Ala Ala His Leu Arg Tyr Ala Phe Asp Gly Ser Val Thr Arg Ala Ala
        195                 200                 205

Gln Phe Ala Ala Asn Leu Val Arg Thr Thr
    210                 215

<210> SEQ ID NO 20
<211> LENGTH: 216
<212> TYPE: PRT
<213> ORGANISM: Rhodococcus

<400> SEQUENCE: 20

Met Lys Arg Arg Leu Ile Ala Tyr Ser Ile Ala Ala Leu Ala Ile Ser
1               5                   10                  15

Ala Thr Ala Val Ala Leu Pro Thr Gly Val Ala Ser Ala Ala Pro Cys
            20                  25                  30

Ser Asp Val Asp Val Ser Phe Ala Arg Gly Thr Gly Glu Leu Pro Gly
        35                  40                  45

Leu Gly Ile Thr Gly Thr Pro Phe Val Asn Ser Val Lys Ser Gln Leu
    50                  55                  60

Ser Asp Arg Ser Val Ser Thr Tyr Ala Val Asn Tyr Ala Ala Asp Phe
65                  70                  75                  80

Thr Gln Ala Ser Ala Gly Pro Gly Ser Arg Asp Leu Val Ala His Leu
                85                  90                  95

Asn Ser Val Ala Ala Ser Cys Pro Ser Thr Lys Phe Val Ile Gly Gly
            100                 105                 110

Tyr Ser Gln Gly Ala Thr Val Val Thr Asn Ala Val Gly Leu Arg Thr

```
                    115                 120                 125
Pro Ser Ser Phe Thr Gly Ala Val Ile Pro Ala Ala Ile Ala Asp Arg
    130                 135                 140

Ile Glu Ala Val Val Val Phe Gly Asn Pro Phe Gly Leu Thr Gly Arg
145                 150                 155                 160

Lys Ile Glu Thr Ala Ser Ser Thr Tyr Gly Ser Arg Thr Asn Ser Phe
                    165                 170                 175

Cys Asn Phe Gly Asp Pro Val Cys Gln Ile Gly Gly Phe Asn Thr Phe
                180                 185                 190

Ala His Leu Thr Tyr Gly Thr Asn Gly Ser Thr Thr Gln Gly Ala Ser
                    195                 200                 205

Phe Ala Ala Ala Gln Val Arg Ser
    210                 215

<210> SEQ ID NO 21
<211> LENGTH: 262
<212> TYPE: PRT
<213> ORGANISM: Artificial Sequence
<220> FEATURE:
<223> OTHER INFORMATION: CfKr fusion protein

<400> SEQUENCE: 21

Ala Pro Ala Cys Pro Asp Val Glu Leu Val Phe Ala Arg Gly Thr Gly
1               5                   10                  15

Glu Ala Ala Gly Leu Gly Ile Val Gly Arg Pro Leu Glu Arg Ala Leu
                20                  25                  30

Ala Ala Glu Leu Pro Gly Arg Thr Val Val Ala Thr Ala Val Asp Tyr
            35                  40                  45

Ala Ala Ser Ser Ser Gln Ala Ser Ala Gly Pro Gly Ser Gly Asp Met
        50                  55                  60

Val Ala Lys Val Arg Ser Arg Ala Ala Cys Pro Gly Thr Gln Phe
65                  70                  75                  80

Val Leu Gly Gly Tyr Ser Gln Gly Ala Thr Val Thr Asp Leu Ala Leu
                85                  90                  95

Gly Ile Arg Thr Gly Val Thr Ala Gly Thr Ala Leu Pro Glu Asp Leu
            100                 105                 110

Ala Ala Arg Val Ala Ala Val Val Tyr Gly Asn Pro Leu Gly Leu
        115                 120                 125

Thr Arg Arg Thr Ile Ala Gln Ala Ala Pro Ala Phe Ala Thr Arg Thr
    130                 135                 140

Val Glu Tyr Cys Asn Ala Gly Asp Pro Val Cys Glu Pro Gly Gly Gly
145                 150                 155                 160

Arg Phe Thr Ala His Ile Thr Tyr Ala Thr Asn Gly Thr Val Leu Glu
                165                 170                 175

Gly Ala Arg Phe Ala Ala Ala Arg Val Thr Ala Ala Gly Thr Pro Thr
            180                 185                 190

Thr Pro Thr Pro Thr Pro Thr Pro Thr Pro Val Pro Thr Thr Cys Val
        195                 200                 205

Thr Ala Ser Ser Leu Gln His Val Arg Asp Gly Arg Ala Tyr Pro Leu
    210                 215                 220

Trp Met Arg Thr Tyr Ala Arg Gly Ser Gly Asp Pro Leu Gly Val Leu
225                 230                 235                 240

Ser Ser Arg Thr Val Val Ser Leu Gln Ala Asp Gly Thr Asp Thr Trp
                245                 250                 255

Arg Lys Val Ala Ala Cys
```

<210> SEQ ID NO 22
<211> LENGTH: 1152
<212> TYPE: DNA
<213> ORGANISM: Artificial Sequence
<220> FEATURE:
<223> OTHER INFORMATION: CfKr coding sequence

<400> SEQUENCE: 22

```
atggagaaaa acatgaaaaa agaggggcg tttttagggc tgttgttggt ttctgcctgc      60
gcatcagttt tcgctgccaa taatgaaacc agcaagtcgg tcactttccc aaagtgtgaa    120
gatctggatg ctgccggaat tgccgcgagc gtaaaacgtg attatcaaca aaatcgcgtg    180
gcgcgttggg cagatgatca aaaaattgtc ggtcaggccg atcccgtggc ttgggtcagt    240
ttgcaggaca ttcagggtaa agatgataaa tggtcagtac cgctaaccgt gcgtggtaaa    300
agtgccgata ttcattacca ggtcagcgtg gactgcaaag cgggaatggc ggaatatcag    360
cggcgtgcgc ccgcctgccc cgacgtcgag ctcgtgttcg cccgcggcac cggggaggcc    420
gcaggcctcg gcatcgtcgg gcgccccctc gagcgcgcgc tcgccgccga gctgcccggc    480
cgcacggtcg tggccaccgc cgtcgactac gccgcgagct cgtcgcaggc cagcgccggc    540
ccggggtcgg gcgacatggt cgcgaaggtc cggtcccgcg cggccgcgtg ccccgggacg    600
cagttcgtgc tcggcggcta ctcgcaggcc gccaccgtca ccgacctggc cctgggcatc    660
cgcaccggcg tcacggccgg caccgcgctc ccggaggacc tggcggctcg ggtcgccgcc    720
gtcgtcgtgt acggcaaccc gctggggctg acgcgacgca ccatcgcgca ggccgcgccg    780
gcgttcgcga cgcggaccgt cgagtactgc aacgccggcg accccgtctg cgagcccggc    840
ggcggccgct tcaccgcaca catcacctac gccaccaacg ggaccgtgct cgagggcgca    900
cggttcgcgg cggcgcgcgt gacggcaggt acgcctacca ccccgacccc gacgccgacc    960
cctacgccgg ttcctaccac atgcgtcacc gccagctcgc tgcagcacgt gcgcgacgga   1020
cgcgcgtacc ccctgtggat gcggacctac gcgcgcggct cgggcgaccc gctcggcgtc   1080
ctgagcagcc gcacggtcgt ctccctccag gcggacggca ccgacacgtg gcgcaaggtc   1140
gccgcctgct ga                                                       1152
```

<210> SEQ ID NO 23
<211> LENGTH: 262
<212> TYPE: PRT
<213> ORGANISM: Artificial Sequence
<220> FEATURE:
<223> OTHER INFORMATION: KrCf fusion protein

<400> SEQUENCE: 23

```
Ala Thr Cys Ser Asp Val Asp Val Val Phe Ala Arg Gly Thr Gly Glu
1               5                   10                  15

Thr Pro Gly Leu Gly Val Val Gly Gly Pro Phe Val Arg Ser Leu Thr
            20                  25                  30

Gly Glu Leu Ser Asp Arg Thr Val Thr Ser His Ala Val Asp Tyr Ala
        35                  40                  45

Ala Ser Ser Ser Gln Ala Ser Ala Gly Pro Gly Ala Thr Ala Met Ser
    50                  55                  60

Ala His Val Arg Glu Val Ala Ala Ala Cys Pro Ser Thr Arg Phe Val
65                  70                  75                  80

Leu Gly Gly Tyr Ser Gln Gly Ala Thr Val Thr Asp Ile Ala Leu Gly
                85                  90                  95
```

```
Ile Arg Thr Gly Thr Thr Gly Thr Pro Val Pro Ala Glu Leu Ala
            100                 105                 110
Gly Arg Val Ala Ala Val Val Phe Gly Asn Pro Leu Gly Leu Ser
        115                 120                 125
Gly Arg Thr Ile Ala Thr Ala Ser Ser Thr Tyr Gly Pro Lys Ser Lys
    130                 135                 140
Asp Tyr Cys Asn Ser Ser Asp Ser Val Cys Gly Ser Ala Pro Lys Thr
145                 150                 155                 160
Gly Thr Gly Gly His Leu Ser Tyr Ala Ser Asn Gly Ser Thr Thr Asp
                165                 170                 175
Gly Ala Arg Phe Ala Ala Gly Leu Val Arg Ala Ala Gly Thr Pro Thr
            180                 185                 190
Thr Pro Thr Pro Thr Pro Thr Pro Thr Pro Val Pro Thr Thr Cys Val
        195                 200                 205
Thr Ala Ser Ser Leu Gln His Val Arg Asp Gly Arg Ala Tyr Pro Leu
    210                 215                 220
Trp Met Arg Thr Tyr Ala Arg Gly Ser Gly Asp Pro Leu Gly Val Leu
225                 230                 235                 240
Ser Ser Arg Thr Val Val Ser Leu Gln Ala Asp Gly Thr Asp Thr Trp
                245                 250                 255
Arg Lys Val Ala Ala Cys
            260
```

<210> SEQ ID NO 24
<211> LENGTH: 1155
<212> TYPE: DNA
<213> ORGANISM: Artificial Sequence
<220> FEATURE:
<223> OTHER INFORMATION: KrCf fusion protein coding sequence

<400> SEQUENCE: 24

```
atggagaaaa acatgaaaaa aagaggggcg ttttagggc tgttgttggt ttctgcctgc     60
gcatcagttt cgctgccaa taatgaaacc agcaagtcgg tcactttccc aaagtgtgaa   120
gatctggatg ctgccggaat tgccgcgagc gtaaaacgtg attatcaaca aaatcgcgtg   180
gcgcgttggg cagatgatca aaaaattgtc ggtcaggccg atcccgtggc ttgggtcagt   240
ttgcaggaca ttcagggtaa agatgataaa tggtcagtac cgctaaccgt gcgtggtaaa   300
agtgccgata ttcattacca ggtcagcgtg gactgcaaag cgggaatggc ggaatatcag   360
cggcgtgcga cttgcagtga cgtcgatgtg gttttcgcgc gtggcactgg tgaaacgccg   420
ggcctgggcg ttgtgggagg accgtttgtg cgttctttaa ccggcgaatt aagcgatcgt   480
accgtgacaa gccatgcggt tgactatgca gccagtagtt cccaggctag cgctggtccg   540
ggtgcaacgg caatgtctgc ccacgtccgc gaagtagctg ccgcctgccc gtcgacccgt   600
tttgttctgg gtggttattc gcaaggtgca acggttacag acatcgcctt agggatacgt   660
accggtacca ccaccggtac tcctgtaccg gccgaactgg cgggccgcgt tgcagctgtt   720
gtggtctttg gaaatccgct gggtctgtca ggacgtacta ttgctaccgc gtcatctacg   780
tatggtccga atccaaagga ttactgtaat tcttcagatt cagtgtgcgg ctccgccccg   840
aaaaccggca caggcggtca tctgtcatac gcgagtaatg gttctaccac tgatggtgct   900
cgttttgcag cgggacttgt ccgtgcagcc ggtacgccta ccaccccgac ccgacgccg    960
accctacgc cggttcctac acatgccgtc accgccagct cgctgcagca cgtgcgcgac  1020
ggacgcgcgt acccctgtg gatgcggacc tacgcgcgcg gctcgggcga cccgctcggc  1080
```

```
gtcctgagca gccgcacggt cgtctccctc caggcggacg gcaccgacac gtggcgcaag    1140
gtcgccgcct gctga                                                    1155
```

<210> SEQ ID NO 25
<211> LENGTH: 313
<212> TYPE: PRT
<213> ORGANISM: Cellulomonas bogoriensis 69B4 (KGM14008.1)

<400> SEQUENCE: 25

```
Met Ser Thr Ser Pro Val Arg Arg Thr Leu Thr Ala Ala Leu Leu Ala
1               5                   10                  15

Ala Gly Leu Ala Ala Thr Ser Val Ala Leu Ser Pro Ala Ala Ser Ala
            20                  25                  30

Thr Ser Leu Pro Ala Ala Ala Pro Leu Ser Ala Gly Ser Cys Pro Asp
        35                  40                  45

Val Gln Val Val Phe Ala Arg Gly Thr Gly Glu Arg Ala Gly Leu Gly
    50                  55                  60

Ile Ile Gly Arg Pro Phe Ala Arg Ala Leu Ala Asp Glu Leu Pro Gly
65                  70                  75                  80

Met Thr Val Thr Ser His Ala Val Asp Tyr Ala Ala Ala Ser Gln
                85                  90                  95

Arg Ser Ala Gly Pro Gly Ala Thr Ala Met Thr Asp His Val Thr Ala
            100                 105                 110

Met Ala Ala Arg Cys Pro Gly Thr Gln Phe Val Leu Gly Gly Tyr Ser
        115                 120                 125

Gln Gly Ala Thr Val Thr Ser Ile Ala Leu Gly Ile Arg Ala Gly Thr
    130                 135                 140

Thr Thr Gly Arg Ala Ile Pro Asp Glu Leu Ser Asp Arg Val Ala Ala
145                 150                 155                 160

Val Val Val Phe Gly Asn Pro Leu Gly Met Arg Gly Gln Thr Ile Ala
                165                 170                 175

Ser Ala Ser Arg Thr Tyr Ala Asp Arg Ala Lys Asp Tyr Cys Asn Ser
            180                 185                 190

Gly Asp Ser Ile Cys Gly Arg Gln Pro Ser Thr Gly Arg Gly Thr His
        195                 200                 205

Thr Gly Tyr Ala Thr Asn Gly Ser Thr Thr Asp Gly Ala Arg Phe Ala
    210                 215                 220

Ala Gly Leu Val Thr Ala Asn Pro Pro Glu Ala Ala Pro Pro Thr Ala
225                 230                 235                 240

Pro Pro Thr Thr Pro Thr Thr Pro Ala Pro Pro Ser Asp Gln Val
                245                 250                 255

Thr Cys Val Thr Ala Gln Val Ser Glu His Val Glu Ala Arg Arg Ala
            260                 265                 270

Ile Arg Gly Leu Thr Arg Ala Tyr Ala Arg Gly Thr Leu Glu Asp Ile
        275                 280                 285

Gly Arg Leu Arg Ser Thr Glu Glu Val Ser Leu Arg Arg Ser Gly Thr
    290                 295                 300

Phe Ser Trp Thr Pro Thr Ala Ser Cys
305                 310
```

<210> SEQ ID NO 26
<211> LENGTH: 187
<212> TYPE: PRT
<213> ORGANISM: Amycolatopsis sp.

```
<400> SEQUENCE: 26

Ala Cys Ser Asp Leu Glu Ile Val Phe Ala Arg Gly Ser Gly Glu Ala
1               5                   10                  15

Pro Gly Leu Gly Ile Thr Gly Thr Pro Leu Val Ser Asp Val Lys Ser
            20                  25                  30

Ala Leu Ser Ser Ala Ser Val Ser Ser Tyr Ala Val Asp Tyr Ala Ala
        35                  40                  45

Ser Tyr Asp Gln Thr Ser Ala Gly Pro Gly Ala Thr Asp Met Ser Asn
    50                  55                  60

His Ile Lys Ser Thr Ala Ala Cys Pro Asp Thr Lys Phe Ala Ile
65                  70                  75                  80

Gly Gly Tyr Ser Gln Gly Ala Ser Val Thr Asp Ile Ala Ile Gly Ile
                85                  90                  95

Arg Thr Tyr Leu Gly Thr Gly Gln Thr Ile Pro Thr Glu Leu Ala Pro
                100                 105                 110

Arg Val Val Ala Val Ile Ala Phe Gly Asn Pro Leu Gly Leu Tyr Gly
            115                 120                 125

Gln Thr Ile Lys Thr Ala Ser Pro Thr Tyr Gly Pro Lys Ser Leu Glu
        130                 135                 140

Phe Cys Asn Arg Gly Asp Asn Val Cys Gly Gly Thr Gly Thr Gly Pro
145                 150                 155                 160

Gly Tyr Gly His Leu Ser Tyr Ala Arg Asp Gly Ser Val Asp Gln Ala
                165                 170                 175

Ala Ala Phe Ile Ala Lys Gln Tyr Asn Ala Ser
                180                 185

<210> SEQ ID NO 27
<211> LENGTH: 261
<212> TYPE: PRT
<213> ORGANISM: Artificial Sequence
<220> FEATURE:
<223> OTHER INFORMATION: Am-Kr variant

<400> SEQUENCE: 27

Ala Cys Ser Asp Leu Glu Ile Val Phe Ala Arg Gly Ser Gly Glu Ala
1               5                   10                  15

Pro Gly Leu Gly Ile Thr Gly Thr Pro Leu Val Ser Asp Val Lys Ser
            20                  25                  30

Ala Leu Ser Ser Ala Ser Val Ser Ser Tyr Ala Val Asp Tyr Ala Ala
        35                  40                  45

Ser Tyr Asp Gln Thr Ser Ala Gly Pro Gly Ala Thr Asp Met Ser Asn
    50                  55                  60

His Ile Lys Ser Thr Ala Ala Cys Pro Asp Thr Lys Phe Ala Ile
65                  70                  75                  80

Gly Gly Tyr Ser Gln Gly Ala Ser Val Thr Asp Ile Ala Ile Gly Ile
                85                  90                  95

Arg Thr Tyr Leu Gly Thr Gly Gln Thr Ile Pro Thr Glu Leu Ala Pro
                100                 105                 110

Arg Val Val Ala Val Ile Ala Phe Gly Asn Pro Leu Gly Leu Tyr Gly
            115                 120                 125

Gln Thr Ile Lys Thr Ala Ser Pro Thr Tyr Gly Pro Lys Ser Leu Glu
        130                 135                 140

Phe Cys Asn Arg Gly Asp Asn Val Cys Gly Gly Thr Gly Thr Gly Pro
145                 150                 155                 160

Gly Tyr Gly His Leu Ser Tyr Ala Arg Asp Gly Ser Val Asp Gln Ala
```

```
                            165                 170                 175
        Ala Ala Phe Ile Ala Lys Gln Tyr Asn Ala Ser Ala Gly Thr Pro Thr
                        180                 185                 190

Thr Pro Thr Pro Thr Pro Thr Pro Thr Pro Val Pro Thr Thr Cys Val
                        195                 200                 205

Arg Asp Ser Thr Arg Asp His Val Ala Ala Asp Arg Ala Val Ser Leu
                        210                 215                 220

Tyr Gly Arg Ala Tyr Ala Arg Gly Ser Arg Asp Ser Leu Gly Ala Thr
        225                 230                 235                 240

Ser Ser Tyr Asn Val Val Ser Leu Gln Gln Val Glu Gly Gly Trp Arg
                        245                 250                 255

Leu Val Thr Ala Cys
                        260

<210> SEQ ID NO 28
<211> LENGTH: 271
<212> TYPE: PRT
<213> ORGANISM: Cellulomonas flavigena

<400> SEQUENCE: 28

Ala Pro Ala Cys Pro Asp Val Glu Leu Val Phe Ala Arg Gly Thr Gly
1               5                   10                  15

Glu Ala Ala Gly Leu Gly Ile Val Gly Arg Pro Leu Glu Arg Ala Leu
                20                  25                  30

Ala Ala Glu Leu Pro Gly Arg Thr Val Val Thr Ala Val Asp Tyr
                35                  40                  45

Ala Ala Ser Ser Ser Gln Ala Ser Ala Gly Pro Gly Ser Gly Asp Met
            50                  55                  60

Val Ala Lys Val Arg Ser Arg Ala Ala Cys Pro Gly Thr Gln Phe
65                  70                  75                  80

Val Leu Gly Gly Tyr Ser Gln Gly Ala Thr Val Thr Asp Leu Ala Leu
                85                  90                  95

Gly Ile Arg Thr Gly Val Thr Ala Gly Thr Ala Leu Pro Glu Asp Leu
            100                 105                 110

Ala Ala Arg Val Ala Ala Val Val Tyr Gly Asn Pro Leu Gly Leu
            115                 120                 125

Thr Arg Arg Thr Ile Ala Gln Ala Ala Pro Ala Phe Ala Thr Arg Thr
130                 135                 140

Val Glu Tyr Cys Asn Ala Gly Asp Pro Val Cys Glu Pro Gly Gly Gly
145                 150                 155                 160

Arg Phe Thr Ala His Ile Thr Tyr Ala Thr Asn Gly Thr Val Leu Glu
                165                 170                 175

Gly Ala Arg Phe Ala Ala Arg Val Thr Ala Pro Ala Pro Thr Pro
                180                 185                 190

Thr Pro Gly Pro Thr Gly Thr Pro Ala Pro Val Pro Ser Ala Glu Pro
            195                 200                 205

Thr Pro Ala Pro Gly Asp Thr Cys Val Thr Ala Ser Ser Leu Gln His
            210                 215                 220

Val Arg Asp Gly Arg Ala Tyr Pro Leu Trp Met Arg Thr Tyr Ala Arg
225                 230                 235                 240

Gly Ser Gly Asp Pro Leu Gly Val Leu Ser Ser Arg Thr Val Val Ser
                245                 250                 255

Leu Gln Ala Asp Gly Thr Asp Thr Trp Arg Lys Val Ala Ala Cys
                260                 265                 270
```

<210> SEQ ID NO 29
<211> LENGTH: 262
<212> TYPE: PRT
<213> ORGANISM: Artificial Sequence
<220> FEATURE:
<223> OTHER INFORMATION: Cf-TP variant

<400> SEQUENCE: 29

```
Ala Pro Ala Cys Pro Asp Val Glu Leu Val Phe Ala Arg Gly Thr Gly
1               5                   10                  15

Glu Ala Ala Gly Leu Gly Ile Val Gly Arg Pro Leu Glu Arg Ala Leu
            20                  25                  30

Ala Ala Glu Leu Pro Gly Arg Thr Val Val Ala Thr Ala Val Asp Tyr
        35                  40                  45

Ala Ala Ser Ser Gln Ala Ser Ala Gly Pro Gly Ser Gly Asp Met
    50                  55                  60

Val Ala Lys Val Arg Ser Arg Ala Ala Cys Pro Gly Thr Gln Phe
65                  70                  75                  80

Val Leu Gly Gly Tyr Ser Gln Gly Ala Thr Val Thr Asp Leu Ala Leu
                85                  90                  95

Gly Ile Arg Thr Gly Val Thr Ala Gly Thr Ala Leu Pro Glu Asp Leu
            100                 105                 110

Ala Ala Arg Val Ala Ala Val Val Tyr Gly Asn Pro Leu Gly Leu
        115                 120                 125

Thr Arg Arg Thr Ile Ala Gln Ala Ala Pro Ala Phe Ala Thr Arg Thr
    130                 135                 140

Val Glu Tyr Cys Asn Ala Gly Asp Pro Val Cys Glu Pro Gly Gly Gly
145                 150                 155                 160

Arg Phe Thr Ala His Ile Thr Tyr Ala Thr Asn Gly Thr Val Leu Glu
                165                 170                 175

Gly Ala Arg Phe Ala Ala Ala Arg Val Thr Ala Gly Thr Pro Thr
            180                 185                 190

Thr Pro Thr Pro Thr Pro Thr Pro Val Pro Thr Thr Cys Val
        195                 200                 205

Thr Ala Ser Ser Leu Gln His Val Arg Asp Gly Arg Ala Tyr Pro Leu
    210                 215                 220

Trp Met Arg Thr Tyr Ala Arg Gly Ser Gly Asp Pro Leu Gly Val Leu
225                 230                 235                 240

Ser Ser Arg Thr Val Val Ser Leu Gln Ala Asp Gly Thr Asp Thr Trp
                245                 250                 255

Arg Lys Val Ala Ala Cys
            260
```

<210> SEQ ID NO 30
<211> LENGTH: 187
<212> TYPE: PRT
<213> ORGANISM: Artificial Sequence
<220> FEATURE:
<223> OTHER INFORMATION: cutinase catalytic domain of CfCUT

<400> SEQUENCE: 30

```
Ala Pro Ala Cys Pro Asp Val Glu Leu Val Phe Ala Arg Gly Thr Gly
1               5                   10                  15

Glu Ala Ala Gly Leu Gly Ile Val Gly Arg Pro Leu Glu Arg Ala Leu
            20                  25                  30

Ala Ala Glu Leu Pro Gly Arg Thr Val Val Ala Thr Ala Val Asp Tyr
        35                  40                  45
```

```
Ala Ala Ser Ser Ser Gln Ala Ser Ala Gly Pro Gly Ser Gly Asp Met
        50                  55                  60

Val Ala Lys Val Arg Ser Arg Ala Ala Cys Pro Gly Thr Gln Phe
 65                  70                  75                  80

Val Leu Gly Gly Tyr Ser Gln Gly Ala Thr Val Thr Asp Leu Ala Leu
                 85                  90                  95

Gly Ile Arg Thr Gly Val Thr Ala Gly Thr Ala Leu Pro Glu Asp Leu
            100                 105                 110

Ala Ala Arg Val Ala Ala Val Val Tyr Gly Asn Pro Leu Gly Leu
            115                 120                 125

Thr Arg Arg Thr Ile Ala Gln Ala Ala Pro Ala Phe Ala Thr Arg Thr
            130                 135                 140

Val Glu Tyr Cys Asn Ala Gly Asp Pro Val Cys Glu Pro Gly Gly Gly
145                 150                 155                 160

Arg Phe Thr Ala His Ile Thr Tyr Ala Thr Asn Gly Thr Val Leu Glu
                165                 170                 175

Gly Ala Arg Phe Ala Ala Ala Arg Val Thr Ala
            180                 185
```

<210> SEQ ID NO 31
<211> LENGTH: 28
<212> TYPE: PRT
<213> ORGANISM: Artificial Sequence
<220> FEATURE:
<223> OTHER INFORMATION: T/P-rich linker domain of CfCUT

<400> SEQUENCE: 31

```
Pro Ala Pro Thr Pro Thr Pro Gly Pro Thr Gly Thr Pro Ala Pro Val
 1                   5                  10                  15

Pro Ser Ala Glu Pro Thr Pro Ala Pro Gly Asp Thr
                20                  25
```

<210> SEQ ID NO 32
<211> LENGTH: 56
<212> TYPE: PRT
<213> ORGANISM: Artificial Sequence
<220> FEATURE:
<223> OTHER INFORMATION: polymer binding domain of CfCUT

<400> SEQUENCE: 32

```
Cys Val Thr Ala Ser Ser Leu Gln His Val Arg Asp Gly Arg Ala Tyr
 1                   5                  10                  15

Pro Leu Trp Met Arg Thr Tyr Ala Arg Gly Ser Gly Asp Pro Leu Gly
                20                  25                  30

Val Leu Ser Ser Arg Thr Val Val Ser Leu Gln Ala Asp Gly Thr Asp
            35                  40                  45

Thr Trp Arg Lys Val Ala Ala Cys
        50                  55
```

<210> SEQ ID NO 33
<211> LENGTH: 182
<212> TYPE: PRT
<213> ORGANISM: Artificial Sequence
<220> FEATURE:
<223> OTHER INFORMATION: cutinase catalytic domain of CbCUT1
       (KGM14009.1)

<400> SEQUENCE: 33

```
Thr Gly Asp Cys Pro Asp Val His Val Val Phe Ala Arg Gly Thr Gly
 1                   5                  10                  15
```

```
Glu Pro Arg Gly Leu Gly Ile Val Gly Arg Pro Phe Val Ser Asp Leu
            20                  25                  30

Gly Asp Ala Leu Pro Thr Met Thr Val Thr Ser Tyr Ala Val Asn Tyr
        35                  40                  45

Ser Ala Asn Ala Ser Gln Thr Ser Ala Gly Pro Gly Ala Gly Asp Met
 50                  55                  60

Thr Ser His Val Thr Ser Met Ala Ala Arg Cys Pro Gly Thr Gln Phe
 65                  70                  75                  80

Val Leu Gly Gly Tyr Ser Gln Gly Ala Thr Val Thr Ser Ile Ala Val
                85                  90                  95

Gly Ala Arg Ser Thr Ser Ile Arg Ser Arg Val Leu Pro Ala Asn Leu
            100                 105                 110

Glu Pro Arg Val Ala Ala Val Val Phe Gly Asn Pro Leu Gly Leu
            115                 120                 125

Thr Arg Arg Thr Ile Ala Ser Glu Ala Pro Ala Tyr Ala Ala Lys Ser
        130                 135                 140

Arg Asp Tyr Cys Asn Arg Ser Asp Thr Val Cys Gly Gly Arg Gly Asp
145                 150                 155                 160

Ala Arg Gly Gly His Leu Ala Tyr Val Ser Asn Gly Ser Val Ala Asp
                165                 170                 175

Gly Ala Ala Phe Ala Ala
            180
```

<210> SEQ ID NO 34
<211> LENGTH: 11
<212> TYPE: PRT
<213> ORGANISM: Artificial Sequence
<220> FEATURE:
<223> OTHER INFORMATION: linker of CbCUT1 (KGM14009.1)

<400> SEQUENCE: 34

```
Ser Leu Val Gly Val Ala Pro Gly Asp Pro Ala
 1               5                  10
```

<210> SEQ ID NO 35
<211> LENGTH: 57
<212> TYPE: PRT
<213> ORGANISM: Artificial Sequence
<220> FEATURE:
<223> OTHER INFORMATION: polymer binding domain of CbCUT1 (KGM14009.1)

<400> SEQUENCE: 35

```
Ser Cys Val Thr Ala Arg Ala Val Asp His Val Glu Ala Asp Arg Ala
 1               5                  10                  15

Phe Arg Ser Val Leu Arg Ala Tyr Ala Arg Gly Ser Arg Asp Pro Leu
            20                  25                  30

Gly Arg Leu Thr Ser Ser Asp Leu Val Ser Leu Gln Arg Thr Gly Gln
        35                  40                  45

Asp Ser Trp Ser Val Val Pro Ala Cys
 50                  55
```

<210> SEQ ID NO 36
<211> LENGTH: 188
<212> TYPE: PRT
<213> ORGANISM: Artificial Sequence
<220> FEATURE:
<223> OTHER INFORMATION: cutinase catalytic domain of CbCUT2
      (KGM14008.1)

<400> SEQUENCE: 36

```
Ala Gly Ser Cys Pro Asp Val Gln Val Val Phe Ala Arg Gly Thr Gly
1               5                   10                  15

Glu Arg Ala Gly Leu Gly Ile Ile Gly Arg Pro Phe Ala Arg Ala Leu
            20                  25                  30

Ala Asp Glu Leu Pro Gly Met Thr Val Thr Ser His Ala Val Asp Tyr
        35                  40                  45

Ala Ala Ala Ala Ser Gln Arg Ser Ala Gly Pro Gly Ala Thr Ala Met
    50                  55                  60

Thr Asp His Val Thr Ala Met Ala Ala Arg Cys Pro Gly Thr Gln Phe
65                  70                  75                  80

Val Leu Gly Gly Tyr Ser Gln Gly Ala Thr Val Thr Ser Ile Ala Leu
                85                  90                  95

Gly Ile Arg Ala Gly Thr Thr Thr Gly Arg Ala Ile Pro Asp Glu Leu
            100                 105                 110

Ser Asp Arg Val Ala Ala Val Val Phe Gly Asn Pro Leu Gly Met
        115                 120                 125

Arg Gly Gln Thr Ile Ala Ser Ala Ser Arg Thr Tyr Ala Asp Arg Ala
            130                 135                 140

Lys Asp Tyr Cys Asn Ser Gly Asp Ser Ile Cys Gly Arg Gln Pro Ser
145                 150                 155                 160

Thr Gly Arg Gly Thr His Thr Gly Tyr Ala Thr Asn Gly Ser Thr Thr
                165                 170                 175

Asp Gly Ala Arg Phe Ala Ala Gly Leu Val Thr Ala
            180                 185

<210> SEQ ID NO 37
<211> LENGTH: 22
<212> TYPE: PRT
<213> ORGANISM: Artificial Sequence
<220> FEATURE:
<223> OTHER INFORMATION: T/P-rich linker of CbCUT2 (KGM14008.1)

<400> SEQUENCE: 37

Asn Pro Pro Glu Ala Ala Pro Pro Thr Ala Pro Pro Thr Thr Pro Pro
1               5                   10                  15

Thr Thr Pro Ala Pro Pro
            20

<210> SEQ ID NO 38
<211> LENGTH: 61
<212> TYPE: PRT
<213> ORGANISM: Artificial Sequence
<220> FEATURE:
<223> OTHER INFORMATION: polymer binding domain of CbCUT2 (KGM14008.1)

<400> SEQUENCE: 38

Ser Asp Gln Val Thr Cys Val Thr Ala Gln Val Ser Glu His Val Glu
1               5                   10                  15

Ala Arg Arg Ala Ile Arg Gly Leu Thr Arg Ala Tyr Ala Arg Gly Thr
            20                  25                  30

Leu Glu Asp Ile Gly Arg Leu Arg Ser Thr Glu Glu Val Ser Leu Arg
        35                  40                  45

Arg Ser Gly Thr Phe Ser Trp Thr Pro Thr Ala Ser Cys
    50                  55                  60

<210> SEQ ID NO 39
<211> LENGTH: 181
<212> TYPE: PRT
```

<213> ORGANISM: Artificial Sequence
<220> FEATURE:
<223> OTHER INFORMATION: cutinase catalytic domain of CcCUT (DSM 20118)

<400> SEQUENCE: 39

Ala Pro Ala Cys Ala Asp Val Glu Val Leu Phe Ala Arg Gly Thr Gly
1               5                   10                  15

Glu Ala Pro Gly Leu Gly Val Leu Gly Thr Pro Phe Val Arg Ser Val
            20                  25                  30

Thr Ser Ala Leu Ser Asp Arg Thr Val Thr Ser Tyr Ala Val Asn Tyr
        35                  40                  45

Ala Ala Glu Ser Ser Gln Arg Ser Ala Gly Pro Gly Ala Thr Asp Leu
    50                  55                  60

Thr Asn His Leu Thr Ala Thr Ala Ala Cys Pro Gly Thr Arg Phe
65                  70                  75                  80

Val Leu Gly Gly Tyr Ser Gln Gly Ala Thr Val Val Asp Leu Ala Leu
                85                  90                  95

Gly Ile Arg Thr Gly Thr Thr Thr Gly Thr Ala Ile Pro Ala Ala Leu
            100                 105                 110

Glu Pro Arg Val Ala Ala Ile Val Val Phe Gly Asn Pro Leu Gly Ile
        115                 120                 125

Ser Gly Arg Thr Ile Ala Thr Ala Ser Pro Thr Tyr Ala Ala Arg Ala
    130                 135                 140

Arg Asp Phe Cys Ala Thr Gly Asp Pro Val Cys Gly Gly Gly Ser Ser
145                 150                 155                 160

Phe Ala Ala His Leu Ala Tyr Arg Thr Asn Gly Asp Val Thr Ala Gly
                165                 170                 175

Ala Asp Phe Ala Ala
            180

<210> SEQ ID NO 40
<211> LENGTH: 49
<212> TYPE: PRT
<213> ORGANISM: Artificial Sequence
<220> FEATURE:
<223> OTHER INFORMATION: T/P-rich linker of CcCUT (DSM 20118)

<400> SEQUENCE: 40

Gly Leu Ala Arg Ala Thr Thr Val Pro Val Pro Thr Pro Thr Val Pro
1               5                   10                  15

Gly Thr Pro Thr Pro Ser Pro Thr Ala Pro Gly Thr Pro Thr Pro Val
            20                  25                  30

Pro Thr Thr Ser Pro Thr Pro Ala Pro Ser Pro Thr Ala Pro Gly Ala
        35                  40                  45

Ala

<210> SEQ ID NO 41
<211> LENGTH: 55
<212> TYPE: PRT
<213> ORGANISM: Artificial Sequence
<220> FEATURE:
<223> OTHER INFORMATION: polymer binding domain of CcCUT (DSM 20118)

<400> SEQUENCE: 41

Cys Val Arg Ala Ser Thr Arg Ala His Val Glu Ala Gly Arg Ala Glu
1               5                   10                  15

Arg Arg His Gly Ile Ala Tyr Ala Thr Gly Ser Gly Asp Arg Ile Gly
            20                  25                  30

Trp Val Ser Ser Phe Val Arg Val Ser Val Gln Gln Thr Ala Asp Gly
            35                  40                  45

Trp Glu Arg Val Leu Ser Cys
    50                  55

<210> SEQ ID NO 42
<211> LENGTH: 186
<212> TYPE: PRT
<213> ORGANISM: Artificial Sequence
<220> FEATURE:
<223> OTHER INFORMATION: cutinase catalytic domain of FrCUT (BMG5.12)

<400> SEQUENCE: 42

Ala Ala Thr Cys Ser Asp Val Asp Val Val Phe Ala Arg Gly Ser Gly
1               5                   10                  15

Glu Leu Pro Gly Leu Gly Ile Thr Gly Thr Pro Phe Val Asn Ser Val
            20                  25                  30

Lys Gln Gly Leu Thr Gly Lys Thr Val Ser Ser Tyr Ala Val Asn Tyr
        35                  40                  45

Ala Ala Asp Ile Ala Gln Thr Ser Asp Gly Ala Gly Ala Thr Asp Met
    50                  55                  60

Thr Arg His Val Arg Ser Val Ala Ala Ser Cys Pro Asn Thr Lys Phe
65                  70                  75                  80

Val Leu Gly Gly Tyr Ser Gln Gly Ala Ser Val Thr Asp Ile Ser Ile
                85                  90                  95

Gly Ile Arg Thr Phe Leu Gly Ser Gly Glu Thr Ile Pro Thr Glu Leu
            100                 105                 110

Ala Pro Arg Val Ala Ala Val Val Phe Gly Asn Pro Leu Ala Leu
        115                 120                 125

Phe Gly Gln Lys Ile Thr Thr Ala Ser Pro Leu Tyr Gly Pro Lys Ala
    130                 135                 140

Lys Glu Phe Cys Asn Leu Gly Asp Pro Val Cys Ala Gly Gly Phe Asn
145                 150                 155                 160

Val Phe Ala His Leu Thr Tyr Gly Phe Asp Gly Ser Thr Ala Asn Gly
                165                 170                 175

Ala Ser Phe Ala Val Ser Lys Val Arg Ala
            180                 185

<210> SEQ ID NO 43
<211> LENGTH: 186
<212> TYPE: PRT
<213> ORGANISM: Artificial Sequence
<220> FEATURE:
<223> OTHER INFORMATION: cutinase catalytic domain of AcCUT (431)

<400> SEQUENCE: 43

Ala Gly Asp Cys Ser Asp Val Glu Leu Val Phe Ala Arg Gly Thr Gly
1               5                   10                  15

Glu Pro Gln Gly Leu Gly Ile Val Gly Arg Pro Leu Ala Arg Glu Leu
            20                  25                  30

Ala Ala Ala Leu Pro Asp Leu Ala Val Gly Ser Phe Ala Val Val Tyr
        35                  40                  45

Ala Ala Ala Gly Asn Gln Arg Ser Ala Gly Pro Gly Ala Thr Asn Met
    50                  55                  60

Ser Arg His Ile Thr Glu Val Ala Gly Glu Cys Pro Asp Thr Arg Phe
65                  70                  75                  80

Val Ile Gly Gly Tyr Ser Gln Gly Ala Ser Val Thr Asp Ile Ala Ile
                85                  90                  95

```
Gly Ile Arg Gly Ala Gly Thr Ala Gly Glu Ala Ile Pro Glu Arg Leu
            100                 105                 110

Ala Asp Arg Val Ala Ala Val Val Phe Gly Asn Pro Leu Gly Leu
            115                 120                 125

Gln Arg Arg Thr Ile Ala Gly Ser Ser Ala Val Phe Gly Pro Lys Ala
            130                 135                 140

Lys Glu Phe Cys Asn Thr Gly Asp Pro Val Cys Gly Gly Gly Asn
145                 150                 155                 160

Phe Ala Ala His Leu Ala Tyr Pro Arg Asn Gly Ser Val Gln Gln Ala
                165                 170                 175

Ala Ala Phe Ala Ala Ser Lys Ile Ala Gly
            180                 185

<210> SEQ ID NO 44
<211> LENGTH: 187
<212> TYPE: PRT
<213> ORGANISM: Artificial Sequence
<220> FEATURE:
<223> OTHER INFORMATION: cutinase catalytic domain of CaCUT (DSM 44712)

<400> SEQUENCE: 44

Thr Ala Ala Cys Ser Asp Val Gln Val Val Phe Ala Arg Gly Ser Thr
1               5                   10                  15

Glu Ala Pro Gly Leu Gly Ile Leu Gly Arg Pro Leu Val Ser Ala Val
            20                  25                  30

Gln Gln Gln Leu Pro Gly Leu Thr Val Asp Ser Tyr Ala Val Asp Tyr
        35                  40                  45

Ala Ala Asn Val Ser Gln Thr Ser Ala Gly Pro Gly Ala Thr Asp Met
    50                  55                  60

Ser Asp His Ile Thr Glu Val Ala Ala Arg Cys Pro Asp Thr Glu Phe
65                  70                  75                  80

Val Ile Gly Gly Tyr Ser Gln Gly Ala Ser Val Thr Asp Ile Ala Ile
                85                  90                  95

Gly Ile Arg Thr Thr Leu Gly Arg Gly Gly Thr Ile Pro Glu Asn Leu
            100                 105                 110

Ala Pro Arg Ile Lys Ala Val Thr Val Phe Gly Asn Pro Leu Arg Leu
            115                 120                 125

Ser Arg Gln Thr Ile Asn Ser Ala Ser Gln Leu Tyr Gly Arg Lys Ala
            130                 135                 140

Ile Asp Ile Cys Ala Thr Gly Asp Pro Val Cys Gly Asn Gly Ala Asn
145                 150                 155                 160

Ala Ala Ala His Leu Arg Tyr Ala Phe Asp Gly Ser Val Thr Arg Ala
                165                 170                 175

Ala Gln Phe Ala Ala Asn Leu Val Arg Thr Thr
            180                 185

<210> SEQ ID NO 45
<211> LENGTH: 188
<212> TYPE: PRT
<213> ORGANISM: Artificial Sequence
<220> FEATURE:
<223> OTHER INFORMATION: cutinase catalytic domain of RhCUT

<400> SEQUENCE: 45

Ala Ala Pro Cys Ser Asp Val Asp Val Ser Phe Ala Arg Gly Thr Gly
1               5                   10                  15

Glu Leu Pro Gly Leu Gly Ile Thr Gly Thr Pro Phe Val Asn Ser Val
```

```
              20                  25                  30
Lys Ser Gln Leu Ser Asp Arg Ser Val Ser Thr Tyr Ala Val Asn Tyr
         35                  40                  45
Ala Ala Asp Phe Thr Gln Ala Ser Ala Gly Pro Gly Ser Arg Asp Leu
     50                  55                  60
Val Ala His Leu Asn Ser Val Ala Ala Ser Cys Pro Ser Thr Lys Phe
 65                  70                  75                  80
Val Ile Gly Gly Tyr Ser Gln Gly Ala Thr Val Thr Asn Ala Val
                 85                  90                  95
Gly Leu Arg Thr Pro Ser Ser Phe Thr Gly Ala Val Ile Pro Ala Ala
                100                 105                 110
Ile Ala Asp Arg Ile Glu Ala Val Val Phe Gly Asn Pro Phe Gly
                115                 120                 125
Leu Thr Gly Arg Lys Ile Glu Thr Ala Ser Ser Thr Tyr Gly Ser Arg
                130                 135                 140
Thr Asn Ser Phe Cys Asn Phe Gly Asp Pro Val Cys Gln Ile Gly Gly
145                 150                 155                 160
Phe Asn Thr Phe Ala His Leu Thr Tyr Gly Thr Asn Gly Ser Thr Thr
                165                 170                 175
Gln Gly Ala Ser Phe Ala Ala Ala Gln Val Arg Ser
                180                 185

<210> SEQ ID NO 46
<211> LENGTH: 271
<212> TYPE: PRT
<213> ORGANISM: Artificial Sequence
<220> FEATURE:
<223> OTHER INFORMATION: CbCUT2 - cutinase from CbCUT2 (KGM14008.1)

<400> SEQUENCE: 46

Ala Gly Ser Cys Pro Asp Val Gln Val Val Phe Ala Arg Gly Thr Gly
 1               5                  10                  15
Glu Arg Ala Gly Leu Gly Ile Ile Gly Arg Pro Phe Ala Arg Ala Leu
                 20                  25                  30
Ala Asp Glu Leu Pro Gly Met Thr Val Thr Ser His Ala Val Asp Tyr
         35                  40                  45
Ala Ala Ala Ala Ser Gln Arg Ser Ala Gly Pro Gly Ala Thr Ala Met
     50                  55                  60
Thr Asp His Val Thr Ala Met Ala Ala Arg Cys Pro Gly Thr Gln Phe
 65                  70                  75                  80
Val Leu Gly Gly Tyr Ser Gln Gly Ala Thr Val Thr Ser Ile Ala Leu
                 85                  90                  95
Gly Ile Arg Ala Gly Thr Thr Thr Gly Arg Ala Ile Pro Asp Glu Leu
                100                 105                 110
Ser Asp Arg Val Ala Ala Val Val Phe Gly Asn Pro Leu Gly Met
                115                 120                 125
Arg Gly Gln Thr Ile Ala Ser Ala Ser Arg Thr Tyr Ala Asp Arg Ala
                130                 135                 140
Lys Asp Tyr Cys Asn Ser Gly Asp Ser Ile Cys Gly Arg Gln Pro Ser
145                 150                 155                 160
Thr Gly Arg Gly Thr His Thr Gly Tyr Ala Thr Asn Gly Ser Thr Thr
                165                 170                 175
Asp Gly Ala Arg Phe Ala Ala Gly Leu Val Thr Ala Asn Pro Pro Glu
                180                 185                 190
Ala Ala Pro Pro Thr Ala Pro Pro Thr Thr Pro Pro Thr Thr Pro Ala
```

```
            195                 200                 205

Pro Pro Ser Asp Gln Val Thr Cys Val Thr Ala Gln Val Ser Glu His
    210                 215                 220

Val Glu Ala Arg Arg Ala Ile Arg Gly Leu Thr Arg Ala Tyr Ala Arg
225                 230                 235                 240

Gly Thr Leu Glu Asp Ile Gly Arg Leu Arg Ser Thr Glu Glu Val Ser
                245                 250                 255

Leu Arg Arg Ser Gly Thr Phe Ser Trp Thr Pro Thr Ala Ser Cys
                260                 265                 270

<210> SEQ ID NO 47
<211> LENGTH: 285
<212> TYPE: PRT
<213> ORGANISM: Artificial Sequence
<220> FEATURE:
<223> OTHER INFORMATION: CcCUT - cutinase from CcCUT (DSM 20118)

<400> SEQUENCE: 47

Ala Pro Ala Cys Ala Asp Val Glu Val Leu Phe Ala Arg Gly Thr Gly
1               5                   10                  15

Glu Ala Pro Gly Leu Gly Val Leu Gly Thr Pro Phe Val Arg Ser Val
                20                  25                  30

Thr Ser Ala Leu Ser Asp Arg Thr Val Thr Ser Tyr Ala Val Asn Tyr
            35                  40                  45

Ala Ala Glu Ser Ser Gln Arg Ser Ala Gly Pro Gly Ala Thr Asp Leu
        50                  55                  60

Thr Asn His Leu Thr Ala Thr Ala Ala Cys Pro Gly Thr Arg Phe
65                  70                  75                  80

Val Leu Gly Gly Tyr Ser Gln Gly Ala Thr Val Val Asp Leu Ala Leu
                85                  90                  95

Gly Ile Arg Thr Gly Thr Thr Gly Thr Ala Ile Pro Ala Ala Leu
                100                 105                 110

Glu Pro Arg Val Ala Ala Ile Val Val Phe Gly Asn Pro Leu Gly Ile
            115                 120                 125

Ser Gly Arg Thr Ile Ala Thr Ala Ser Pro Thr Tyr Ala Ala Arg Ala
        130                 135                 140

Arg Asp Phe Cys Ala Thr Gly Asp Pro Val Cys Gly Gly Ser Ser
145                 150                 155                 160

Phe Ala Ala His Leu Ala Tyr Arg Thr Asn Gly Asp Val Thr Ala Gly
                165                 170                 175

Ala Asp Phe Ala Ala Gly Leu Ala Arg Ala Thr Thr Val Pro Val Pro
            180                 185                 190

Thr Pro Thr Val Pro Gly Thr Pro Thr Pro Ser Pro Thr Ala Pro Gly
        195                 200                 205

Thr Pro Thr Pro Val Pro Thr Thr Ser Pro Thr Pro Ala Pro Ser Pro
    210                 215                 220

Thr Ala Pro Gly Ala Ala Cys Val Arg Ala Ser Thr Arg Ala His Val
225                 230                 235                 240

Glu Ala Gly Arg Ala Glu Arg Arg His Gly Ile Ala Tyr Ala Thr Gly
                245                 250                 255

Ser Gly Asp Arg Ile Gly Trp Val Ser Ser Phe Val Arg Val Ser Val
                260                 265                 270

Gln Gln Thr Ala Asp Gly Trp Glu Arg Val Leu Ser Cys
            275                 280                 285
```

-continued

```
<210> SEQ ID NO 48
<211> LENGTH: 250
<212> TYPE: PRT
<213> ORGANISM: Artificial Sequence
<220> FEATURE:
<223> OTHER INFORMATION: CbCUT1 - cutinase from CbCUT1 (KGM14009.1)

<400> SEQUENCE: 48

Thr Gly Asp Cys Pro Asp Val His Val Phe Ala Arg Gly Thr Gly
1               5                   10                  15

Glu Pro Arg Gly Leu Gly Ile Val Gly Arg Pro Phe Val Ser Asp Leu
            20                  25                  30

Gly Asp Ala Leu Pro Thr Met Thr Val Thr Ser Tyr Ala Val Asn Tyr
        35                  40                  45

Ser Ala Asn Ala Ser Gln Thr Ser Ala Gly Pro Gly Ala Gly Asp Met
    50                  55                  60

Thr Ser His Val Thr Ser Met Ala Ala Arg Cys Pro Gly Thr Gln Phe
65                  70                  75                  80

Val Leu Gly Gly Tyr Ser Gln Gly Ala Thr Val Thr Ser Ile Ala Val
                85                  90                  95

Gly Ala Arg Ser Thr Ser Ile Arg Ser Arg Val Leu Pro Ala Asn Leu
            100                 105                 110

Glu Pro Arg Val Ala Ala Val Val Phe Gly Asn Pro Leu Gly Leu
        115                 120                 125

Thr Arg Arg Thr Ile Ala Ser Glu Ala Pro Ala Tyr Ala Ala Lys Ser
    130                 135                 140

Arg Asp Tyr Cys Asn Arg Ser Asp Thr Val Cys Gly Gly Arg Gly Asp
145                 150                 155                 160

Ala Arg Gly Gly His Leu Ala Tyr Val Ser Asn Gly Ser Val Ala Asp
                165                 170                 175

Gly Ala Ala Phe Ala Ala Ser Leu Val Gly Val Ala Pro Gly Asp Pro
            180                 185                 190

Ala Ser Cys Val Thr Ala Arg Ala Val Asp His Val Glu Ala Asp Arg
        195                 200                 205

Ala Phe Arg Ser Val Leu Arg Ala Tyr Ala Arg Gly Ser Arg Asp Pro
    210                 215                 220

Leu Gly Arg Leu Thr Ser Ser Asp Leu Val Ser Leu Gln Arg Thr Gly
225                 230                 235                 240

Gln Asp Ser Trp Ser Val Val Pro Ala Cys
                245                 250

<210> SEQ ID NO 49
<211> LENGTH: 26
<212> TYPE: PRT
<213> ORGANISM: Artificial Sequence
<220> FEATURE:
<223> OTHER INFORMATION: Cutinase motif from Kineococcus radiotolerans
      (YP_001363838)

<400> SEQUENCE: 49

His Val Arg Glu Val Ala Ala Ala Cys Pro Ser Thr Arg Phe Val Leu
1               5                   10                  15

Gly Gly Tyr Ser Gln Gly Ala Thr Val Thr
            20                  25

<210> SEQ ID NO 50
<211> LENGTH: 29
<212> TYPE: PRT
<213> ORGANISM: Artificial Sequence
```

-continued

```
<220> FEATURE:
<223> OTHER INFORMATION: Cutinase motif from Kineococcus radiotolerans
      (YP_001363838)

<400> SEQUENCE: 50

Tyr Cys Asn Ser Ser Asp Ser Val Cys Gly Ser Ala Pro Lys Thr Gly
1               5                   10                  15

Thr Gly Gly His Leu Ser Tyr Ala Ser Asn Gly Ser Thr
            20                  25

<210> SEQ ID NO 51
<211> LENGTH: 26
<212> TYPE: PRT
<213> ORGANISM: Artificial Sequence
<220> FEATURE:
<223> OTHER INFORMATION: Cutinase motif from Cellulomonas flavigena DSM
      20109 (ZP_04367703)

<400> SEQUENCE: 51

Lys Val Arg Ser Arg Ala Ala Ala Cys Pro Gly Thr Gln Phe Val Leu
1               5                   10                  15

Gly Gly Tyr Ser Gln Gly Ala Thr Val Thr
            20                  25

<210> SEQ ID NO 52
<211> LENGTH: 28
<212> TYPE: PRT
<213> ORGANISM: Artificial Sequence
<220> FEATURE:
<223> OTHER INFORMATION: Cutinase motif from Cellulomonas flavigena DSM
      20109 (ZP_04367703)

<400> SEQUENCE: 52

Tyr Cys Asn Ala Gly Asp Pro Val Cys Glu Pro Gly Gly Gly Arg Phe
1               5                   10                  15

Thr Ala His Ile Thr Tyr Ala Thr Asn Gly Thr Val
            20                  25

<210> SEQ ID NO 53
<211> LENGTH: 26
<212> TYPE: PRT
<213> ORGANISM: Artificial Sequence
<220> FEATURE:
<223> OTHER INFORMATION: Cutinase motif  from Fusarium solani (P00590)

<400> SEQUENCE: 53

Leu Phe Gln Gln Ala Asn Thr Lys Cys Pro Asp Ala Thr Leu Ile Ala
1               5                   10                  15

Gly Gly Tyr Ser Gln Gly Ala Ala Leu Ala
            20                  25

<210> SEQ ID NO 54
<211> LENGTH: 28
<212> TYPE: PRT
<213> ORGANISM: Artificial Sequence
<220> FEATURE:
<223> OTHER INFORMATION: Cutinase motif from Fusarium solani (P00590)

<400> SEQUENCE: 54

Phe Cys Asn Thr Gly Asp Leu Val Cys Thr Gly Ser Leu Ile Val Ala
1               5                   10                  15

Ala Pro His Leu Ala Tyr Gly Pro Asp Ala Arg Gly
            20                  25
```

-continued

<210> SEQ ID NO 55
<211> LENGTH: 26
<212> TYPE: PRT
<213> ORGANISM: Artificial Sequence
<220> FEATURE:
<223> OTHER INFORMATION: Cutinase motif from Phytophthora infestans (AAY43367)

<400> SEQUENCE: 55

```
His Val Val Ser Ile Ala Gln Glu Cys Pro Asn Thr Val Phe Val Leu
1               5                   10                  15

Gly Gly Tyr Ser Gln Gly Ala Ser Val Thr
            20                  25
```

<210> SEQ ID NO 56
<211> LENGTH: 26
<212> TYPE: PRT
<213> ORGANISM: Artificial Sequence
<220> FEATURE:
<223> OTHER INFORMATION: Cutinase motif from Phytophthora infestans (AAY43367)

<400> SEQUENCE: 56

```
Phe Cys Asn Met Gly Asp Pro Val Cys Gly Asn Gly Phe Asn Thr Met
1               5                   10                  15

Ala His Met Thr Tyr Pro Met Asp Ser Val
            20                  25
```

<210> SEQ ID NO 57
<211> LENGTH: 26
<212> TYPE: PRT
<213> ORGANISM: Artificial Sequence
<220> FEATURE:
<223> OTHER INFORMATION: Cutinase motif from Rhodococcus (jostii) RHA1 (YP_700622)

<400> SEQUENCE: 57

```
Arg Ile Gln Phe Met Ala Thr Ser Cys Pro Asn Thr Arg Met Val Val
1               5                   10                  15

Gly Gly Tyr Ser Gln Gly Ala Ala Val Ala
            20                  25
```

<210> SEQ ID NO 58
<211> LENGTH: 30
<212> TYPE: PRT
<213> ORGANISM: Artificial Sequence
<220> FEATURE:
<223> OTHER INFORMATION: Cutinase motif from Rhodococcus (jostii) RHA1 (YP_700622)

<400> SEQUENCE: 58

```
Leu Cys Ala Pro Gly Asp Asn Ile Cys Asp Gly Ala Pro Leu Gly Arg
1               5                   10                  15

Pro Asn Val Ala His Ala Leu Tyr Pro Ala Asn Gly Met Thr
            20                  25                  30
```

<210> SEQ ID NO 59
<211> LENGTH: 26
<212> TYPE: PRT
<213> ORGANISM: Artificial Sequence
<220> FEATURE:
<223> OTHER INFORMATION: Cutinase motif from Magnaporthe grisae (CAA43717)

<400> SEQUENCE: 59

```
Met Phe Thr Leu Ala Asn Thr Lys Cys Pro Asn Ala Ala Val Val Ala
```

```
1               5                   10                  15
Gly Gly Tyr Ser Gln Gly Thr Ala Val Met
            20                  25
```

<210> SEQ ID NO 60
<211> LENGTH: 28
<212> TYPE: PRT
<213> ORGANISM: Artificial Sequence
<220> FEATURE:
<223> OTHER INFORMATION: Cutinase motif from Magnaporthe grisae
      (CAA43717)

<400> SEQUENCE: 60

```
Tyr Cys Asn Ala Ser Asp Ala Val Cys Phe Gly Thr Leu Phe Leu Leu
1               5                   10                  15

Pro Ala His Phe Leu Tyr Thr Thr Glu Ser Ser Ile
            20                  25
```

<210> SEQ ID NO 61
<211> LENGTH: 26
<212> TYPE: PRT
<213> ORGANISM: Artificial Sequence
<220> FEATURE:
<223> OTHER INFORMATION: Cutinase motif from Monilinia fructicola
      (AAZ95012)

<400> SEQUENCE: 61

```
Met Val Ser Ser Ala Leu Ser Ser Cys Pro Asn Thr Lys Leu Val Ile
1               5                   10                  15

Ser Gly Tyr Ser Gln Gly Gly Gln Leu Val
            20                  25
```

<210> SEQ ID NO 62
<211> LENGTH: 28
<212> TYPE: PRT
<213> ORGANISM: Artificial Sequence
<220> FEATURE:
<223> OTHER INFORMATION: Cutinase motif from Monilinia fructicola
      (AAZ95012)

<400> SEQUENCE: 62

```
Ile Cys His Ala Gly Asp Asn Ile Cys Gln His Gly Ser Met Ile Leu
1               5                   10                  15

Met Pro His Leu Thr Tyr Gly Met Asp Ala Thr Ala
            20                  25
```

<210> SEQ ID NO 63
<211> LENGTH: 55
<212> TYPE: PRT
<213> ORGANISM: Artificial Sequence
<220> FEATURE:
<223> OTHER INFORMATION: Polymer-binding domain from Kineococcus
      radiotolerans

<400> SEQUENCE: 63

```
Cys Val Arg Asp Ser Thr Arg Asp His Val Ala Ala Asp Arg Ala Val
1               5                   10                  15

Ser Leu Tyr Gly Arg Ala Tyr Ala Arg Gly Ser Arg Asp Ser Leu Gly
            20                  25                  30

Ala Thr Ser Ser Tyr Asn Val Val Ser Leu Gln Gln Val Glu Gly Gly
        35                  40                  45

Trp Arg Leu Val Thr Ala Cys
    50                  55
```

<210> SEQ ID NO 64
<211> LENGTH: 56
<212> TYPE: PRT
<213> ORGANISM: Artificial Sequence
<220> FEATURE:
<223> OTHER INFORMATION: Polymer-binding domain from Cellulomonas
      flavigena DSM 20109

<400> SEQUENCE: 64

Cys Val Thr Ala Ser Ser Leu Gln His Val Arg Asp Gly Arg Ala Tyr
1               5                   10                  15

Pro Leu Trp Met Arg Thr Tyr Ala Arg Gly Ser Gly Asp Pro Leu Gly
            20                  25                  30

Val Leu Ser Ser Arg Thr Val Val Ser Leu Gln Ala Asp Gly Thr Asp
        35                  40                  45

Thr Trp Arg Lys Val Ala Cys Cys
    50                  55

<210> SEQ ID NO 65
<211> LENGTH: 56
<212> TYPE: PRT
<213> ORGANISM: Artificial Sequence
<220> FEATURE:
<223> OTHER INFORMATION: Polymer-binding domain from Paucimonas
      lemoignei (AAB48166)

<400> SEQUENCE: 65

Cys Tyr Asn Ala Ser Asn Tyr Ala His Val Thr Ala Gly Arg Ala Val
1               5                   10                  15

Asn Ser Met Gly Tyr Ala Lys Ala Lys Gly Ser Asn Gln Asn Met Gly
            20                  25                  30

Leu Tyr Asn Thr Phe Thr Thr Ser Lys Leu Arg Glu Ala Pro Ala Gly
        35                  40                  45

Tyr Phe Thr Ile Asp Ser Thr Cys
    50                  55

<210> SEQ ID NO 66
<211> LENGTH: 56
<212> TYPE: PRT
<213> ORGANISM: Artificial Sequence
<220> FEATURE:
<223> OTHER INFORMATION: Polymer-binding domain from Thermobifida sp.
      BCC23166 PHB depolymerase

<400> SEQUENCE: 66

Cys Val Thr Ala Asn Asn Tyr Gln His Val Ala Glu Gly Arg Ala Tyr
1               5                   10                  15

Val Ser Tyr Gly Tyr Ala Tyr Ser Val Gly Gly Asn Asp Leu Leu Gly
            20                  25                  30

Leu Trp Asn Ile Tyr Val Ile Thr Ser Val Gln Glu Thr Ser Pro Gly
        35                  40                  45

Tyr Trp Glu Arg Val Ser Gly Cys
    50                  55

<210> SEQ ID NO 67
<211> LENGTH: 55
<212> TYPE: PRT
<213> ORGANISM: Artificial Sequence
<220> FEATURE:
<223> OTHER INFORMATION: Polymer-binding domain from Comamonas
      testosteroni (BAA22882)

<400> SEQUENCE: 67

```
<210> SEQ ID NO 68
<211> LENGTH: 56
<212> TYPE: PRT
<213> ORGANISM: Artificial Sequence
<220> FEATURE:
<223> OTHER INFORMATION: Polymer-binding domain from Thermobifida fusca
      YX PHB depolymerase

<400> SEQUENCE: 68

Cys Thr Thr Ala Ser Asn Tyr Ala His Val Gln Ala Asn Arg Ala Tyr
1               5                   10                  15

Gln Gln Gly Gly Tyr Ala Tyr Ala Asn Gly Ser Gly Gln Asn Met Gly
            20                  25                  30

Leu Trp Asn Val Phe Tyr Thr Thr Thr Leu Lys Gln Thr Gly Ser Asn
        35                  40                  45

Tyr Tyr Val Ile Gly Thr Cys
    50                  55

<210> SEQ ID NO 68
<211> LENGTH: 56
<212> TYPE: PRT
<213> ORGANISM: Artificial Sequence
<220> FEATURE:
<223> OTHER INFORMATION: Polymer-binding domain from Thermobifida fusca
      YX PHB depolymerase

<400> SEQUENCE: 68

Cys Val Thr Ala Asn Asn Tyr Gln His Val Ala Glu Gly Arg Ala Tyr
1               5                   10                  15

Val Ser Tyr Gly Tyr Ala Tyr Ser Val Gly Gly Asn Asp Leu Leu Gly
            20                  25                  30

Leu Trp Asn Ile Tyr Val Ile Thr Ser Val Gln Glu Thr Ser Pro Gly
        35                  40                  45

Tyr Trp Glu Arg Val Ser Gly Cys
    50                  55

<210> SEQ ID NO 69
<211> LENGTH: 57
<212> TYPE: PRT
<213> ORGANISM: Artificial Sequence
<220> FEATURE:
<223> OTHER INFORMATION: Polymer-binding domain from Nocardiopsis
      dassonvillei subsp PHB depolymerase

<400> SEQUENCE: 69

Cys Val Arg Asp Ser Asn Tyr Asp His Val Ser Ala Gly Arg Ala Val
1               5                   10                  15

Gln Arg Ser Gly Leu Val Tyr Ala Val Gly Ser Gly Asp Ala Leu Gly
            20                  25                  30

Leu Trp Asn Val Phe Val Thr Thr Ser Leu Thr Glu Thr Ser Pro Gly
        35                  40                  45

His Trp Glu His Thr Pro Gly Gly Cys
    50                  55
```

MULTI-DOMAIN ENZYMES HAVING CUTINASE ACTIVITY, COMPOSITIONS COMPRISING SAME AND USES THEREOF

CROSS-REFERENCE TO RELATED APPLICATION(S)

This application is a continuation of U.S. application Ser. No. 15/044,715, filed Feb. 16, 2016, which claims the benefit of U.S. Provisional Application No. U.S. 62/116,761 filed Feb. 16, 2015. The complete disclosures of these prior applications are incorporated by reference in their entirety.

REFERENCE TO SEQUENCE LISTING

The present application incorporates by reference the Sequence Listing submitted as an ASCII text filed via EFS-Web. The Sequence Listing is provided as a file entitled Sequence Listing_RBCA088.001C1.txt, created on Jul. 28, 2017, which is 91 Kb in size.

FIELD

The present invention relates to enzymes with cutinase activity and methods for transgenic expression thereof, and various uses thereof. More specifically, the present invention is concerned with enzymes with cutinase activity having a modular organization, methods relating to their transgenic expression, compositions comprising same, and uses thereof.

BACKGROUND

Cutinases (EC 3.1.1.74) are hydrolytic enzymes, i.e. hydrolases, that degrade cutin, a component of the plant cuticle that, in addition to waxes, constitute the outermost continuous membrane or "skin" of the primary parts of higher plants. Cutin is a polyester, largely composed of saturated $C_{16}$ (palmitic) acids and unsaturated $C_{18}$ fatty acids cross-linked by ester bonds; the actual composition of which depends on the plant species. The cuticle primarily protects plants from water loss or other environmental stresses, thereby acting as a formidable barrier.

Cutinases have been found predominantly in phytopathogenic fungi as secreted enzymes to facilitate their entry into the host plant. The prototypical cutinase is the FsCUT derived from *Fusarium solani* f sp. *pisi* (aka *Nectria haematococca*) that infects peas. This enzyme plays a role in plant pathogenesis as a virulence factor, but not exclusively since hydrophobic surface binding proteins, called hydrophobins, are also involved. FsCUT is a 230-amino acid enzyme synthesized with a 31 amino-acid signal peptide, with the mature, secreted portion having a molecular mass of 21,600 Da (Soliday et al., 1984). Its structure belongs to the α/β class of hydrolases containing the classical Ser-His-Asp triad (S120, H188 and D175) for catalysis (Martinez et al., 1992).

Owing to the hydrolytic, esterification or transesterification activities, both naturally-occurring or genetically-modified cutinases of *Fusarium* and other organisms, have been produced and applied to varying extent in industries such as food, laundry and detergent, textiles, recycling, and polymer manufacturing.

SUMMARY

The present description stems from the surprising discovery that members of a family of multi-domain enzymes having cutinase activity may have advantageous properties for various industrial applications. In some implementations, these advantageous properties may include improved stability in the presence of an oxidizing agent, improved stability in the presence of an organic solvent, and/or improved enzymatic activity at a broader range of temperatures, relative to prototypical single-domain cutinases.

This family of multi-domain enzymes having cutinase activity includes an endogenous enzyme (KrCUT) from the actinobacterium *Kineococcus radiotolerans*, a highly radiation-resistant actinobacterium isolated from nuclear waste at the Savannah River Site in Aiken, S.C., as well as enzymes from *Cellulomonas bogoriensis, Cellulomonas cellasea*, and *Cellulomonas flavigena*. This family of enzymes differs from prototypical cutinases such as those from the filamentous fungus *Fusarium solani*, in that they have a multi-domain modular organization in the form of a cutinase catalytic domain that has an extra C-terminal segment containing a threnonine/proline-rich (T/P-rich) linker domain, and polymer binding domain. Recombinant proteins having cutinase activity having different improved properties and substrate preferences can thus be engineered using cutinase catalytic domains, linker domains, and polymer binding domains present in cutinases from different organisms.

In some implementations, the present description relates to one or more of the following items.

1. An isolated recombinant protein having cutinase activity, said protein comprising: (a) a cutinase catalytic domain; (b) a proline/threonine-rich linker domain positioned C-terminal of domain (a); and (c) a polymer binding domain positioned C-terminal of domain (b).

2. The isolated recombinant protein of item 1, wherein said protein, as compared to a corresponding native protein comprising domain (a):
   (i) has improved stability to a bleaching agent which is:
      (1) an oxidizing agent which is at least one of: hydrogen peroxide, a peroxide other than hydrogen peroxide, a non-peroxide oxidizing agent, ozone, sodium percarbonate, sodium perborate, or any combination thereof; and/or
      (2) a reducing agent which is at least one of: sodium dithionite, sodium dithionite, sulfur dioxide, a sulfite, a bisulfite, a sodium borohydride, or any combination thereof;
   (ii) has improved stability to an organic solvent which is at least one of: methanol, 2-propanol, or another alcohol, dimethyl sulfoxide (DMSO), dimethylformamide (DMF), acetone, or another organic solvent, or any combination thereof;
   (iii) has a broader temperature activity range; or
   (iv) any combination of (i) to (iii).

3. The isolated recombinant protein of item 1 or 2 which is a chimeric recombinant protein, wherein at least one of domains (a), (b) and (c) is from a cutinase belonging to a different species.

4. The isolated recombinant protein of any one of items 1 to 3, wherein domain (a), (b), and/or (c) is from a multi-domain cutinase belonging to *Kineococcus radiotolerans, Cellulomonas flavigena, Cellulomonas bogoriensis*, or *Cellulomonas cellasea*.

5. The isolated recombinant protein of any one of claims 1 to 4, wherein:
   (i) domain (a) is:
      (1) a cutinase catalytic domain having at least 50%, at least 55%, at least 60%, at least 65%, at least 70%, at least 75%, at least 80%, at least 85%, at least 90%, or at least 95% sequence identity to amino acid sequence of SEQ ID NOs: 2, 30, 33, 36, 39, or 42-45, or to the cutinase catalytic domain of SEQ ID NO: 1, 13-20, or 25;
    (2) a cutinase catalytic domain comprising or consisting of the amino acid sequence of SEQ ID NOs: 2, 30, 33, 36, 39, or 42-45, or the cutinase catalytic domain of SEQ ID NO: 1, 13-20, or 25; or
    (3) both (1) and (2);
  (ii) domain (b) is:
    (1) a threonine/proline-rich linker domain having at least 50%, at least 55%, at least 60%, at least 65%, at least 70%, at least 75%, at least 80%, at least 85%, at least 90%, or at least 95% sequence identity to SEQ ID NO: 3, 31, 34, 37, or 40, or to the threonine/proline-rich linker domain of SEQ ID NO: 1 or 13-15;
    (2) a threonine/proline-rich linker domain comprising or consisting of the amino acid sequence of SEQ ID NO: 3, 31, 34, 37, or 40, or to the threonine/proline-rich linker domain of SEQ ID NO: 1 or 13-15;
    (3) a threonine/proline-rich linker domain having at threonine/proline content of at least 50%, at least 55%, at least 60%, at least 65%, at least 70%, at least 75%, at least 80%, at least 85%, at least 90%, or at least 95% over a stretch of 15 to 55 consecutive amino acids; or
    (4) any combination of (1) to (3);
  (iii) domain (c) is:
    (1) a polymer binding domain having at least 50%, at least 55%, at least 60%, at least 65%, at least 70%, at least 75%, at least 80%, at least 85%, at least 90%, or at least 95% sequence identity to SEQ ID NO: 4, 32, 35, 38, or 41;
    (2) a polymer binding domain comprising or consisting of the amino acid sequence of SEQ ID NO: 4, 32, 35, 38, or 41, or to the polymer binding domain of SEQ ID NO: 1 or 13-15; or
    (3) both (1) and (2); or
  (iv) any combination of (i) to (iii).

6. The isolated recombinant protein of any one of items 1 to 5, wherein said recombinant protein:
  (i) is produced fused to a heterologous carrier protein or heterologous tag that enables secretion of said recombinant protein, and/or facilitates purification or detection of said recombinant protein;
  (ii) is truncated from a native N terminal signal sequence found on a corresponding native cutinase; or
  (iii) both (i) and (ii).

7. The isolated recombinant protein of item 6, wherein said carrier protein is YebF as defined by SEQ ID NO: 8.

8. A polynucleotide molecule comprising a nucleic acid sequence encoding the recombinant protein as defined in any one of items 1 to 7, operably linked to a heterologous promoter.

9. The polynucleotide of item 8, wherein the recombinant protein encoded by said polynucleotide: (i) lacks an N terminal signal sequence of a native cutinase; (ii) is fused to a heterologous carrier protein; or (iii) both (i) and (ii).

10. A vector comprising the polynucleotide molecule as defined in item 8 or 9.

11. A cell comprising the isolated recombinant protein as defined in any one of items 1 to 7, the polynucleotide molecule as defined in item 8 or 9, or the vector as defined in item 9.

12. The cell of item 11, which is a bacterial cell, a yeast cell, a non-yeast fungal cell, an insect cell, a plant cell, an animal cell, or a mammalian cell.

13. The cell of item 12, wherein said cell is from *E. coli*, *Bacillus subtilis*, or *Streptomyces* spp.

14. A composition comprising: (i) the isolated recombinant protein as defined in any one of items 1 to 7; and (ii) a bleaching agent and/or an organic solvent, wherein said recombinant protein retains said cutinase activity when present in said composition.

15. The composition of item 14, wherein:
  (i) said bleaching agent is:
    (1) an oxidizing agent which is or comprises: hydrogen peroxide, a peroxide other than hydrogen peroxide, a non-peroxide oxidizing agent, ozone, sodium percarbonate, sodium perborate, or any combination thereof; and/or
    (2) a reducing agent which is or comprises: sodium dithionite, sodium dithionite, sulfur dioxide, a sulfite, a bisulfite, a sodium borohydride, or any combination thereof;
  (ii) said organic solvent which is or comprises: methanol, 2-propanol, or another alcohol, dimethyl sulfoxide (DMSO), dimethylformamide (DMF), or acetone; or
  (iii) both (i) and (ii).

16. The composition of item 14 or 15, wherein:
  (i) said bleaching agent is present at a concentration of:
    (1) at least 100 ppm, 150 ppm, 200 ppm, 250 ppm, 300 ppm, 350 ppm, 400 ppm, 450 ppm, 500 ppm, 550 ppm, 600 ppm, 650 ppm, 700 ppm, 750 ppm, 800 ppm, 850 ppm, 900 ppm, 950 ppm, 1000 ppm, 1500 ppm, 2000 ppm, 2500 ppm, 3000 ppm, 3500 ppm, 4000 ppm, 4500 ppm, 5000 ppm, 5500 ppm, 6000 ppm, 6500 ppm, or 7000 ppm; or
    (2) between 100 ppm, 150 ppm, 200 ppm, 250 ppm, 300 ppm, 350 ppm, 400 ppm, 450 ppm, 500 ppm, 550 ppm, 600 ppm, 650 ppm, 700 ppm, 750 ppm, 800 ppm, 850 ppm, 900 ppm, 950 ppm, or 1000 ppm, and 1500 ppm, 2000 ppm, 2500 ppm, 3000 ppm, 3500 ppm, 4000 ppm, 4500 ppm, 5000 ppm, 5500 ppm, 6000 ppm, 6500 ppm, or 7000 ppm;
  (ii) said organic solvent is present as a concentration of:
    (1) at least 1%, 2%, 3%, 4%, 5%, 6%, 7%, 8%, 9%, 10%, 15%, 20%, 25%, 30%, 35%, 40%, 45%, or 50% v/v; or
    (2) between 1%, 2%, 3%, 4%, 5%, 6%, 7%, 8%, 9%, 10%, 15%, 20%, or 25%, and 30%, 35%, 40%, 45%, or 50% v/v; or
  (iii) both (i) and (ii).

17. The composition of any one of items 14 to 16, further comprising: (i) an additional recombinant enzyme which is: a lipase, an esterase, a pectate lyase, a pectinase, a cutinase, a cellulase, a hemicellulose, an amylase, or any combination thereof, or another recombinant enzyme; (ii) a detergent; (iii) a surfactant; (iv) a buffer; (v) a chelator; or (vi) any combination of (i) to (v).

18. The composition of any one of items 14 to 17, which is: (i) a cleaning product, a degreaser, a disinfectant, a bleaching product, or any combination thereof; or (ii) feed or a feed additive.

19. Use of the isolated recombinant protein as defined in any one of items 1 to 7, or the composition as defined in any one of items 14 to 17, for: (i) cleaning, degreasing, disinfecting, bleaching product, biofilm control, or any combination thereof; (ii) for inactivating mycotoxin; (iii) bioscouring or other treatment of fabrics or textiles; (iv) catalyzing transesterification reactions; (v) vegetable oil extraction; or (vi) enhanced oil recovery.

20. The use of item 18 for inactivating ochratoxin.
21. A method for producing the recombinant protein as defined in any one of items 1 to 7, said method comprising: (i) culturing a suitable host cell expressing a polynucleotide encoding said recombinant protein, wherein said polynucleotide encodes a truncated recombinant protein lacking an N terminal signal sequence; and (ii) isolating said recombinant protein.
22. The method of item 21, wherein said polynucleotide is operably linked to a heterologous promoter.
23. The method of item 21 or 22, wherein said polynucleotide encodes said recombinant protein fused to a heterologous carrier protein.

In other implementations, the present description relates to one or more of the following items.

1. A recombinant protein having cutinase activity, said protein comprising a cutinase catalytic domain that inactivates mycotoxin.
2. The protein of item 1, wherein said cutinase catalytic domain inactivates ochratoxin.
3. The protein of item 1 or 2, wherein said cutinase catalytic domain inactivates aflatoxin.
4. The protein of any one of items 1 to 3, wherein said cutinase catalytic domain inactivates ochratoxin and aflatoxin.
5. The protein of any one of items 1 to 4, wherein said cutinase catalytic domain shares at least 50%, at least 55%, at least 60%, at least 65%, at least 70%, at least 75%, at least 80%, at least 85%, at least 90%, or at least 95% sequence identity to the cutinase catalytic domain of any one of SEQ ID NOs: 2 and 13-20.
6. A recombinant protein having cutinase activity, said protein comprising a cutinase catalytic domain having at least 50%, at least 55%, at least 60%, at least 65%, at least 70%, at least 75%, at least 80%, at least 85%, at least 90%, or at least 95% sequence identity to the cutinase catalytic domain of SEQ ID NO: 2.
7. The protein of any one of items 1 to 6, wherein said cutinase catalytic domain shares at least 70%, at least 75%, at least 80%, at least 85%, at least 90%, or at least 95% sequence identity to the cutinase catalytic domain of SEQ ID NO: 2.
8. The protein of any one of items 1 to 6, wherein the cutinase catalytic domain comprises the amino acid sequence of SEQ ID NO: 2 or the cutinase catalytic domain of any one of SEQ ID NOs: 13-20.
9. The protein of any one of items 1 to 8, further comprising a polymer binding domain operably linked to said cutinase catalytic domain.
10. The protein of item 9, wherein said polymer binding domain binds to poly(hydroxybutyrate), triacin, tributyrin, trimiristin, tripalmitin, polyvinyl acetate (PVA), polyethylene terephthalate (PET), or polytrimethylene terephthalate (PTT).
11. The protein of item 9 or 10, wherein said polymer binding domain comprises an amino acid sequence sharing at least 50%, at least 55%, at least 60%, at least 65%, at least 70%, at least 75%, at least 80%, at least 85%, at least 90%, or at least 95% sequence identity to the polymer binding domain of any one of SEQ ID NOs: 4 and 13-15.
12. The protein of item 11, wherein said polymer binding domain comprises the amino acid sequence of any one of SEQ ID NOs: 4 and 13-15.
13. The protein of any one of items 1 to 12, wherein said cutinase domain and said polymer binding domain are operably linked by a linker domain.
14. The protein of item 11, wherein said linker domain is a proline/threonine-rich linker domain.
15. The protein of item 13 or 14, wherein said linker domain comprises an amino acid sequence sharing at least 50%, at least 55%, at least 60%, at least 65%, at least 70%, at least 75%, at least 80%, at least 85%, at least 90%, or at least 95% sequence identity to: SEQ ID NO: 3; residues 220-247 of SEQ ID NO: 13; residues 226-236 of SEQ ID NO: 14; or residues 228-276 of SEQ ID NO: 15.
16. A polynucleotide encoding the protein of any one of items 1 to 15.
17. A vector comprising the polynucleotide of item 16 operably linked to a heterologous promoter.
18. A cell comprising the vector of item 17.
19. Use of the protein as defined in any one of items 1 to 15 for inactivating mycotoxin.
20. The use of item 19, wherein said mycotoxin comprises ochratoxin.
21. The use of item 19, wherein said mycotoxin comprises aflatoxin.
22. The use of item 20, wherein said mycotoxin comprises ochratoxin and aflatoxin.
23. Use of the protein of any one of items 1 to 15 for degrading a polymer.
24. The use of item 23, wherein said polymer is a polyester.
25. The use of item 23, wherein said polymer is: cutin; polycaprolactone (PCL); polylactic acid (PLA); poly(1,3-propylen adipate (PPA); poly(hydroxybutyrate); triacin; tributyrin; trimiristin; tripalmitin; polyvinyl acetate (PVA); polyethylene terephthalate (PET); or polytrimethylene terephthalate (PTT).
26. Use of the protein as defined in any one of items 1 to 15 for the manufacture of: a cleaner and/or degreaser; animal feed; a surface treatment product in the pulp and paper industries; or a product for the degradation and/or control of biofilm.
27. A kit for inactivating mycotoxins, said kit comprising the protein as defined in any one of items 1 to 15; and a suitable container.
28. A method for expressing a transgenic KrCUT protein in a cell, said method comprising expression of a YebF-KrCUT nucleotide in the cell.

Other objects, advantages and features of the present invention will become more apparent upon reading of the following non-restrictive description of specific embodiments thereof, given by way of example only with reference to the accompanying drawings.

DEFINITIONS

In the present description, a number of terms are extensively utilized and they should be given the meaning of the person of skill in the art with a mind willing to understand. Furthermore, in order to provide a clear and consistent understanding of the specification and claims, including the scope to be given to such terms, the following definitions are provided.

The term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about".

As used herein, "polynucleotide" or "nucleic acid molecule" refers to a polymer of nucleotides and includes DNA (e.g., genomic DNA, cDNA), RNA molecules (e.g., mRNA), and chimeras thereof. The nucleic acid molecule can be obtained by cloning techniques or synthesized. DNA can be double-stranded or single-stranded (coding strand or non-coding strand [antisense]). Conventional deoxyribonucleic acid (DNA) and ribonucleic acid (RNA) are included in the terms "nucleic acid molecule" and "polynucleotide" as are analogs thereof (e.g., generated using nucleotide analogs, e.g., inosine or phosphorothioate nucleotides). Such nucleotide analogs can be used, for example, to prepare polynucleotides that have altered base-pairing abilities or increased resistance to nucleases. A nucleic acid may comprise only conventional sugars, bases and linkages, as found in RNA and DNA, or may include both conventional components and substitutions.

As used herein, the term "gene" refers to nucleic acid molecules which may be isolated from chromosomal DNA, and very often include an open reading frame encoding a protein, e.g., polypeptides of the present invention. A gene may include coding sequences, non-coding sequences, introns and/or regulatory sequences, as well known.

As used herein, "recombinant protein" refers to a protein produced using cells that do not have, in their native state, an endogenous copy of the DNA able to express the protein. The cells produce the recombinant protein because they have been genetically altered by the introduction of the appropriate isolated nucleic acid sequence. The term "recombinant" also includes reference to a cell, or nucleic acid, or vector, that has been modified by the introduction of a heterologous (exogenous or foreign) nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, under-expressed or not expressed at all.

As used herein, the terms "hybridizing" and "hybridizes" are intended to describe conditions for hybridization and washing under which nucleotide sequences at least about 60%, at least about 70%, at least about 80%, more preferably at least about 85%, even more preferably at least about 90%, more preferably at least 95%, more preferably at least 98% or more preferably at least 99% homologous to each other typically remain hybridized to each other. A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., preferably at 60° C. and even more preferably at 65° C. Highly stringent conditions include, for example, hybridizing at 68° C. in 5×SSC/5×Denhardt's solution/1.0% SDS and washing in 0.2×SSC/0.1% SDS at room temperature. Alternatively, washing may be performed at 42° C. The skilled artisan will know which conditions to apply for stringent and highly stringent hybridization conditions.

The terms "identity" and "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). Preferably, the two sequences are the same length. Thus, In accordance with the present invention, the term "identical" or "percent identity" in the context of two or more nucleic acid or amino acid sequences, refers to two or more sequences or subsequences that are the same, or that have a specified percentage of amino acid residues or nucleotides that are the same (e.g., 60% or 65% identity, preferably, 70-95% identity, more preferably at least 95% identity), when compared and aligned for maximum correspondence over a window of comparison, or over a designated region as measured using a sequence comparison algorithm as known in the art, or by manual alignment and visual inspection. Sequences having, for example, 60% to 95% or greater sequence identity are considered to be substantially identical over their full lengths.

In a related manner, the terms "homology" or "percent homology", refer to a similarity between two polypeptide sequences, but take into account changes between amino acids (whether conservative or not). As well known in the art, amino acids can be classified by charge, hydrophobicity, size, etc. It is also well known in the art that amino acid changes can be conservative (e.g., they do not significantly affect, or not at all, the function of the protein). A multitude of conservative changes are known in the art, Serine for threonine, isoleucine for leucine, arginine for lysine etc., Thus the term homology introduces evolutionistic notions (e.g., pressure from evolution to a retain function of essential or important regions of a sequence, while enabling a certain drift of less important regions).

An "isolated polynucleotide" or "isolated nucleic acid molecule" is a nucleic acid molecule (DNA or RNA) that is not immediately contiguous with both of the coding sequences with which it is immediately contiguous (one on the 5' end and one on the 3' end) in the naturally occurring genome of the organism from which it is derived.

As used herein, an "isolated polypeptide" or "isolated protein" is intended to include a polypeptide or protein removed from its native environment.

The term "variant" refers herein to a polypeptide, which is substantially similar in structure (e.g., amino acid sequence) to a polypeptide disclosed herein or encoded by a nucleic acid sequence disclosed herein without being identical thereto. Thus, two molecules can be considered as variants even though their primary, secondary, tertiary or quaternary structures are not identical. A variant can comprise an insertion, substitution, or deletion of one or more amino acids as compared to its corresponding native protein. A variant can comprise additional modifications (e.g., post-translational modifications).

As used herein, the term "mycotoxin" refers to any toxic product formed in a mold, fungus, and/or yeast that exhibits significant toxicity to a human or animal when ingested or otherwise contacted (e.g., on the skin, in the lungs (inhaled), in the eyes, etc.). Thus, specifically contemplated mycotoxins include aflatoxins (and particularly B1, B2, G1, and G2), fumonisins (and particularly B1, B2, and B3), ochratoxin, deoxynivalenol (DON, vomitoxin), T-2 toxin, and zearalenone.

As used herein the expressions "inactivates", "inactivating", detoxifies", or "detoxifying", in the context of mycotoxins, refers to the processing of a mycotoxin in accordance with the present invention such that an undesirable effect of the mycotoxin is reduced or eliminated. In some embodiments, such undesirable effects may include reduction or elimination of toxicity to a human or animal when the processed mycotoxin is ingested or otherwise contacted (e.g., on the skin, in the lungs (inhaled), in the eyes, etc.).

Other definitions may be provided throughout the description.

Kr SEQ ID NO: 49 and SEQ ID NO: 50;
Cf SEQ ID NO: 51 and SEQ ID NO: 52;
Fs SEQ ID NO: 53 and SEQ ID NO: 54;
Pi SEQ ID NO: 55 and SEQ ID NO: 56;
Rh SEQ ID NO: 57 and SEQ ID NO:58;
Mg SEQ ID NO: 59 and SEQ ID NO: 60;
Mf SEQ ID NO: 61 and SEQ ID NO: 62.

Inset (b): Homology to substrate-binding domains of PH8 depolymerases. The sequences shown in panel (b) are represented in the Sequence Listing as follows:

Kr SEQ ID NO: 63;
Cf SEQ ID NO: 64;
Pl SEQ ID NO: 65;
Ts SEQ ID NO: 66;
Ct SEQ ID NO: 67;
Tf SEQ ID NO: 68;
Nd SEQ ID NO: 69.

Abbreviations of bacterial source: Cf, *Cellulomonas flavigena* DSM 20109 (ZP_04367703); Ct, *Comamonas testosteroni* (BAA22882); Fs, *Fusarium solani* (P00590); Kr, *Kineococcus radiotolerans* cutinase (YP_001363838); Mf, *Monilinia fructicola* (AAZ95012); Mg, *Magnaporthe grisae* (CAA43717); Nd, *Nocardiopsis dassonvillei* subsp PHB depolymerase (ZP_04334644); Pi, *Phytophthora infestans* (AAY43367); Pl, *Paucimonas lemoignei* (AAB48166); Rh, *Rhodococcus* (*jostii*) RHA1 (YP_700622). Tf, *Thermobifida fusca* YX PHB depolymerase (YP_288143, re-annotated as WP_011290529.1); and Ts, *Thermobifida* sp. BCC23166 PHB depolymerase (ACF17837).

Figure 2:
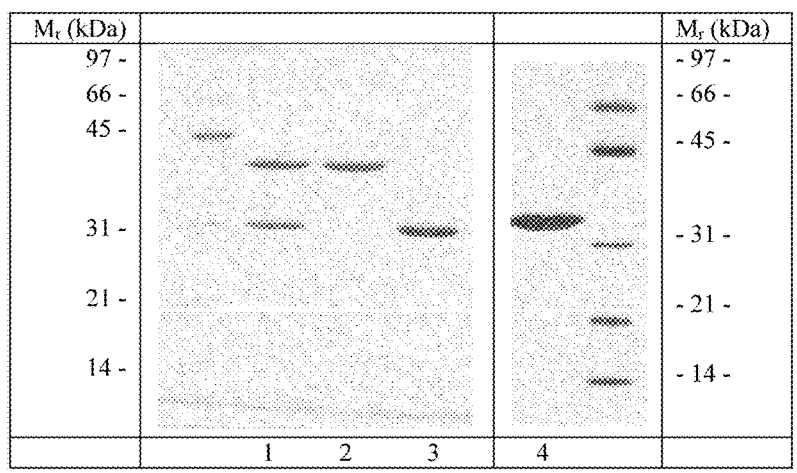

FIG. 2 shows purification of recombinant *K. radiotolerans* cutinase and truncated derivatives. Proteins were analyzed by 10% SDS PAGE, and silver stained. The molecular weight markers are indicated alongside; (a) lane 1, fraction from SP-Sepharose™ showing YebF-KrCUT fusion protein (39 kDa) and mature KrCUT (31 kDa); lanes 2 and 3 from HiLoad™ Superdex™ 75 showing the separated protein bands; (b) lane 4, YebF-KrCUT189 (33 kDa) from HiLoad™ Superdex™ 75.

Figure 3:
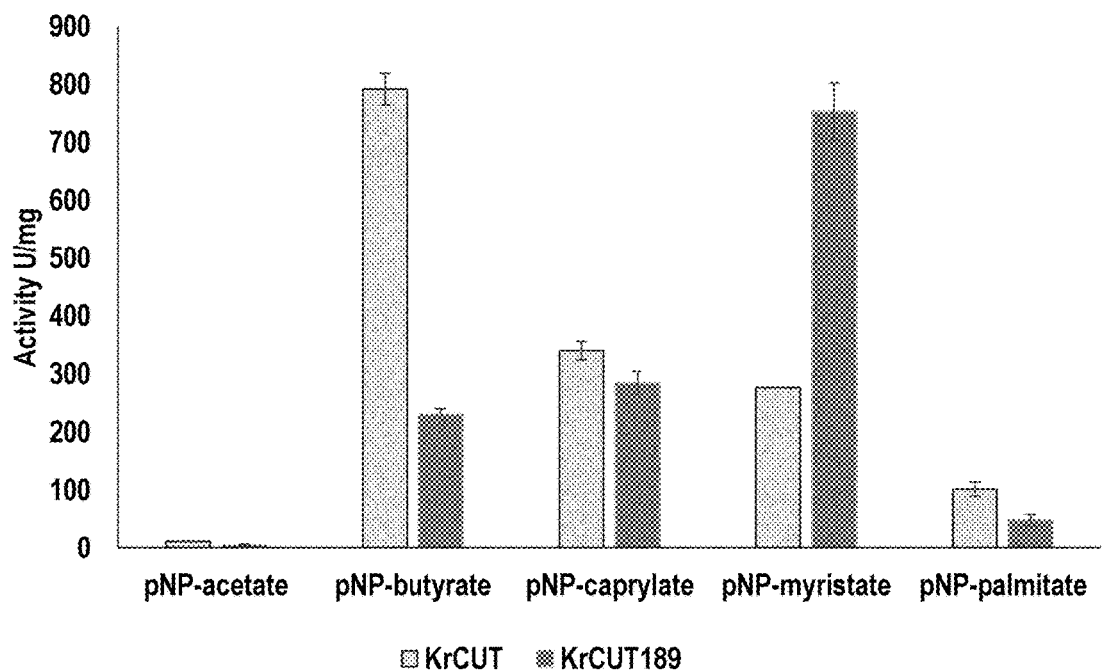

FIG. 3 shows substrate specificity of full-length KrCUT and KrCUT189. Activity (U/mg) towards selected p-nitrophenol esters are compared.

Figure 4:
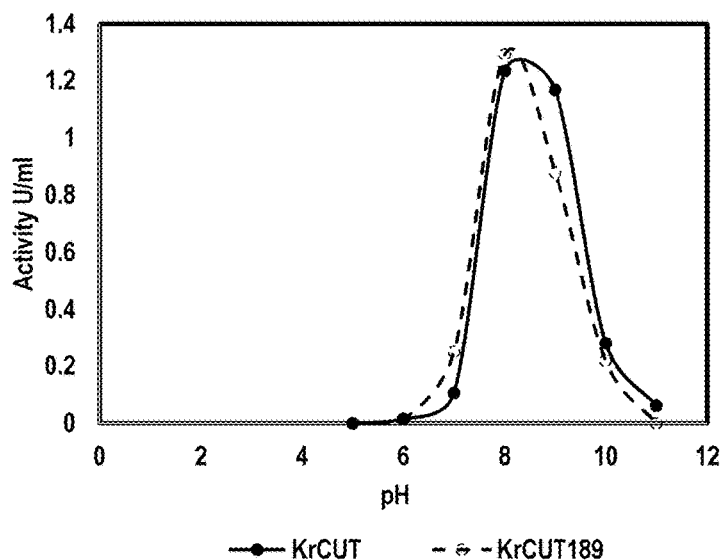

FIG. 4 shows pH optima curves for activity of KrCUT and KrCUT189.

Figure 5:
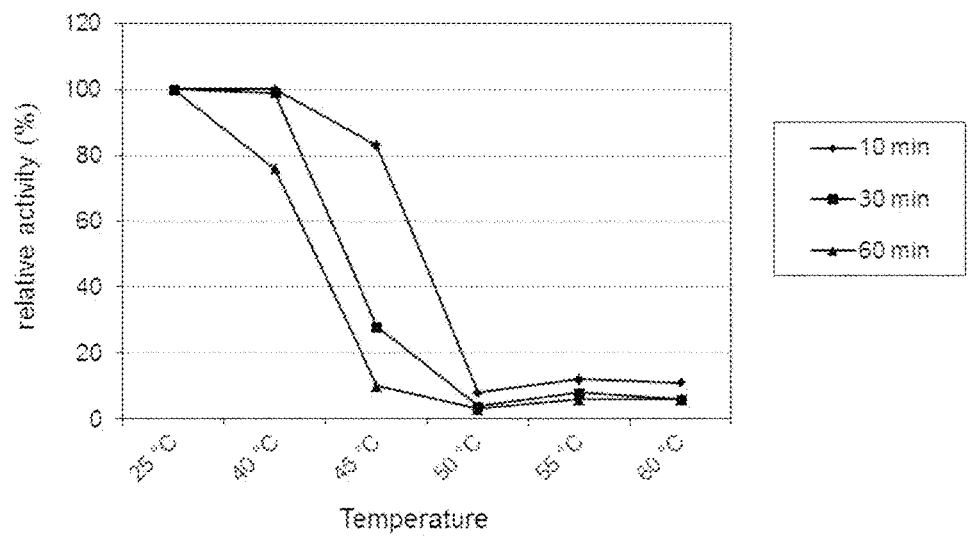

FIG. 5 shows thermostability curves for KrCUT. Activity of the enzyme after incubation at the defined temperatures and for the selected time periods was measured.

Figure 6:
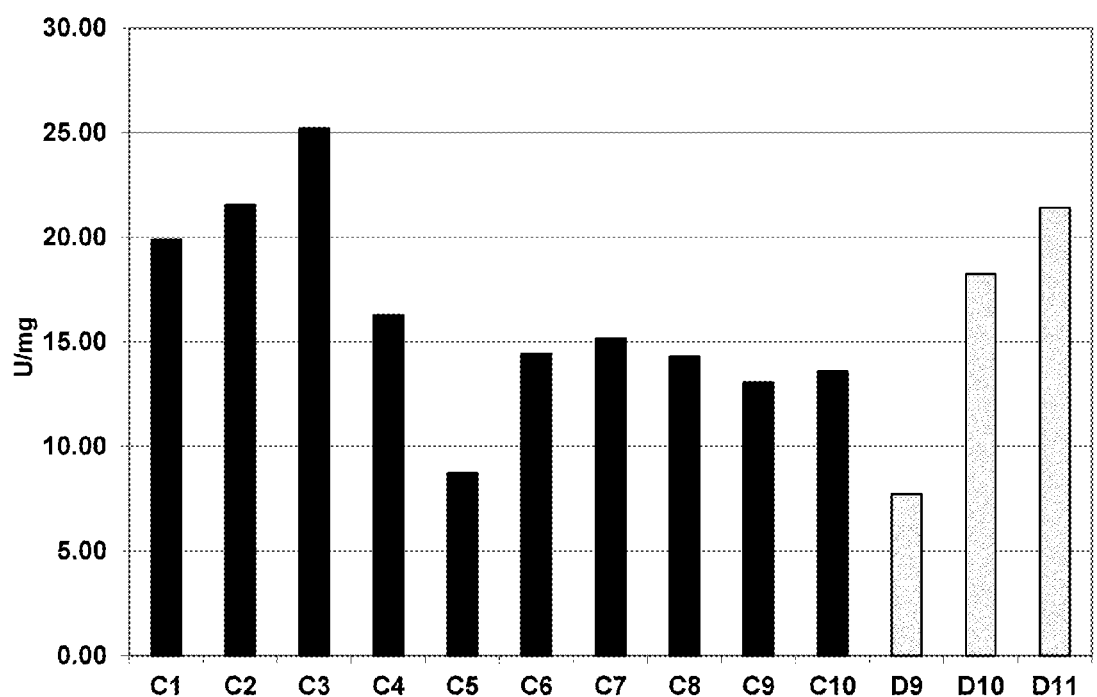

FIG. 6 shows the enzymatic activity of protein purification elution fractions corresponding to KrCUT (fractions C1-C10) and YebF-KrCUT (fractions D9-D11).

Figure 7:
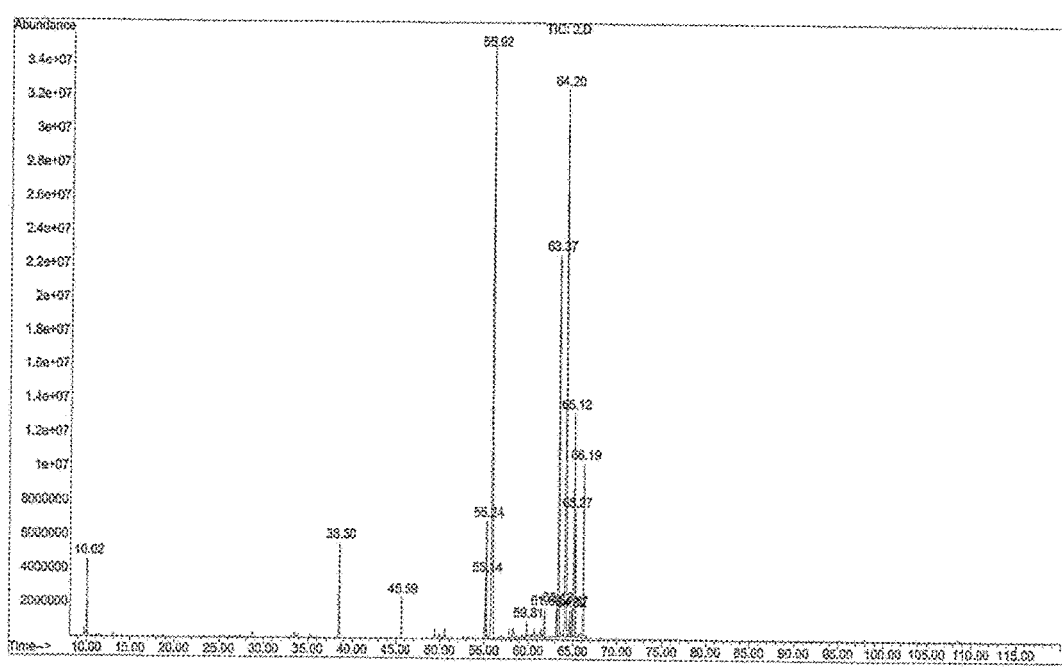

FIG. 7 shows GC analysis of cutin monomers released by KrCUT. The numbers on the peaks correspond to the retention times of the released products as described in the text.

Figure 8:
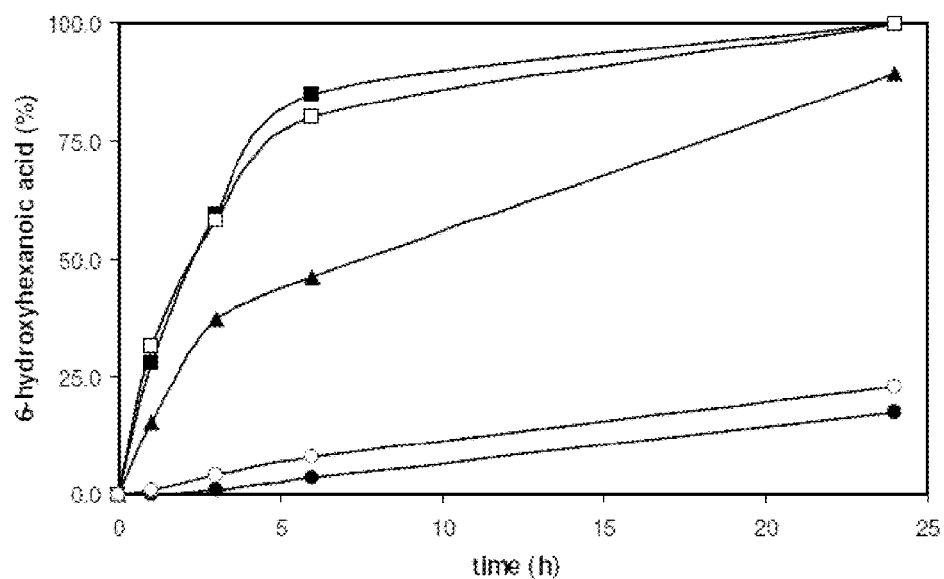
Figure 8:
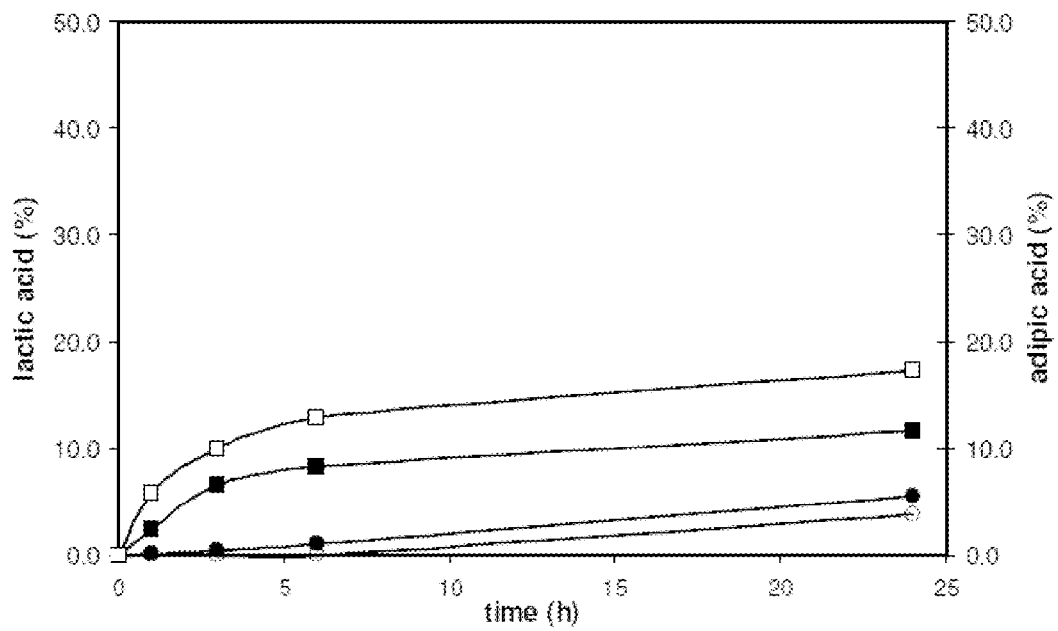

FIG. 8 shows degradation of synthetic polyesters by YebF-KrCUT and KrCUT189. Enzyme concentration is 2.5 µM, unless otherwise stated. (A) Degradation of PCL films (■, YebF-KrCUT; ▲, YebF-KrCUT, 1.25 µM; and □, KrCUT189), and PCL pellets (●, YebF-KrCUT; and ○, KrCUT189). The curve of PCL film degradation by 5 µM YebF-KrCUT approximated that of 2.5 µM enzyme concentration (not shown). (B) Degradation of PLA (●, YebF-KrCUT; and ○, KrCUT189) and polypropylene adipate (■, YebF-KrCUT; and □, KrCUT189).

Figure 9:
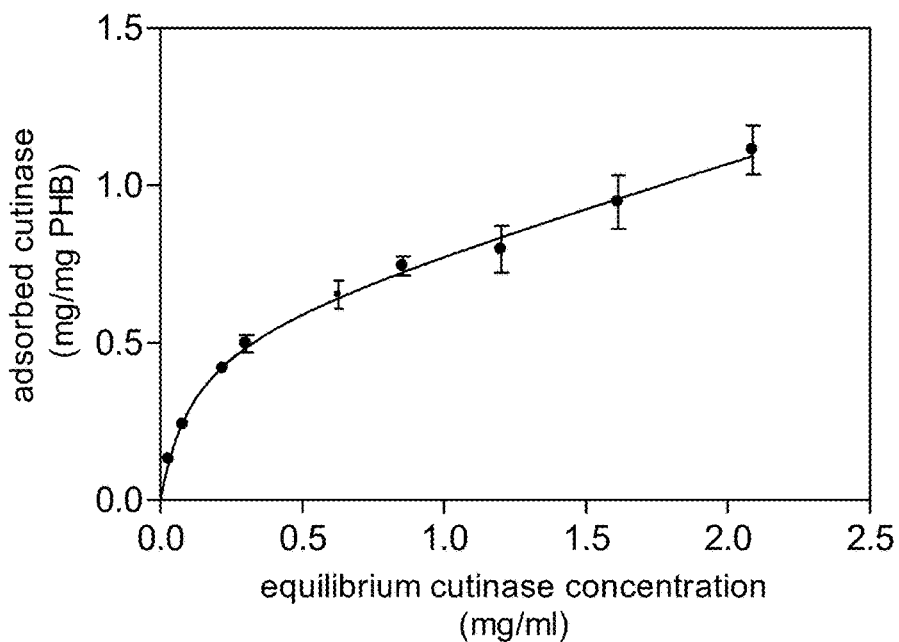

FIG. 9 shows adsorption isotherm of cutinase and PHB granules at 25° C. Purified KrCUT of concentrations ranging from 0.16 to 3.2 mg/mL were mixed with 25 mg PHB in 50 mM sodium phosphate (pH 8.0) in a total volume of 1 mL and mixed by gently shaking for 3 h. The PHB polymer was removed by centrifugation and the concentration of protein in the supernatant was determined by the BCA method. The concentration of bound protein at a particular concentration of cutinase was calculated as the difference between a control without added PHB and free cutinase after incubation with PHB.

Figure 10:
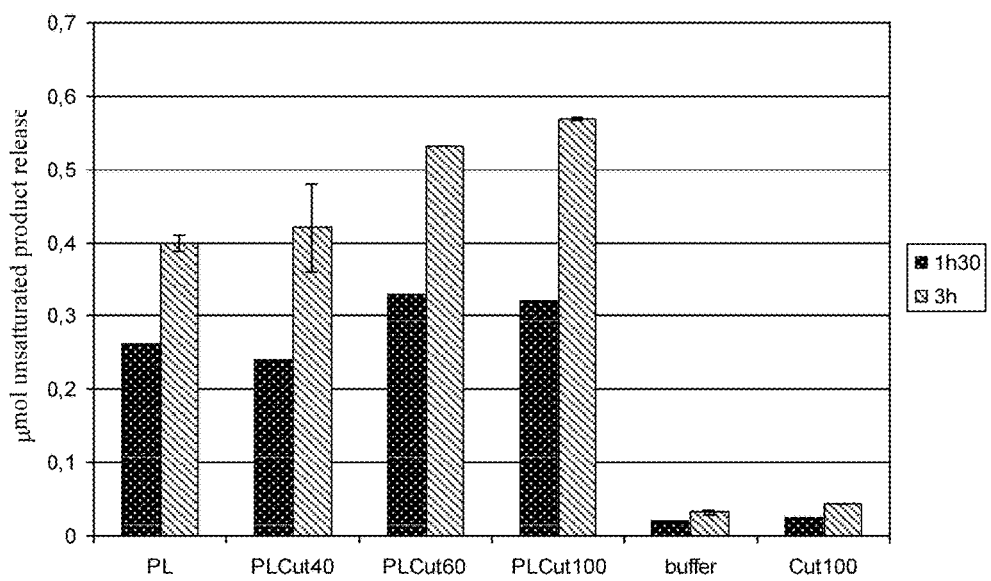

FIG. 10 shows amounts of pectin released from natural hemp fibres by pectate lyase (PL) or in combination with cutinase (Cut) at different concentrations. The shaded bars indicate the two different incubation periods (1.5 h and 3 h).

Figure 11:
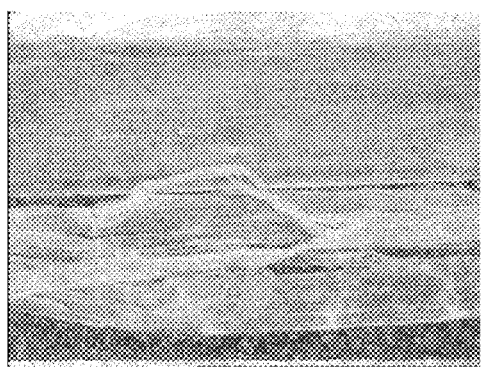
Figure 11:
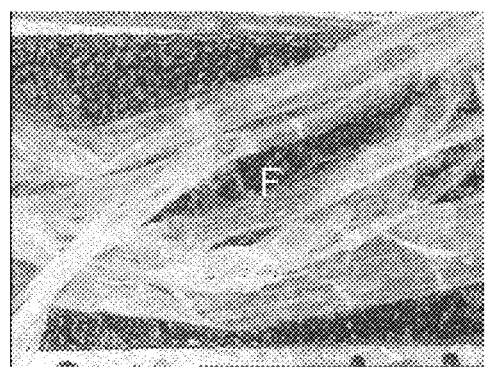
Figure 11:
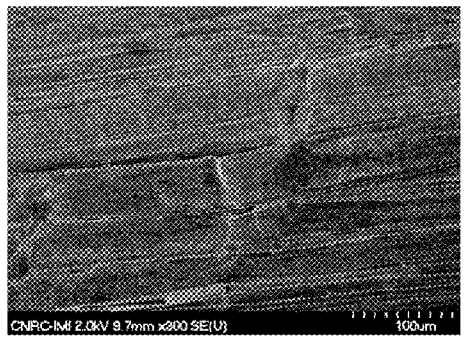
Figure 11:
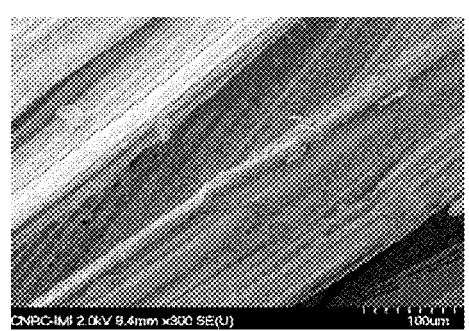

FIGS. 11 (A) and (B) show light microscopic analysis of hemp fibre obtained by enzymatic retting. (A) pectate lyase treatment, fibers are embedded into pectin and wax material; (B) pectate lyase and cutinase treatment, fiber, F cell in bundles. (C) and (D) represents images from scanning electron microscopy (SEM): (C) pectate lyase; (D) pectate lyase and cutinase.

Figure 12:
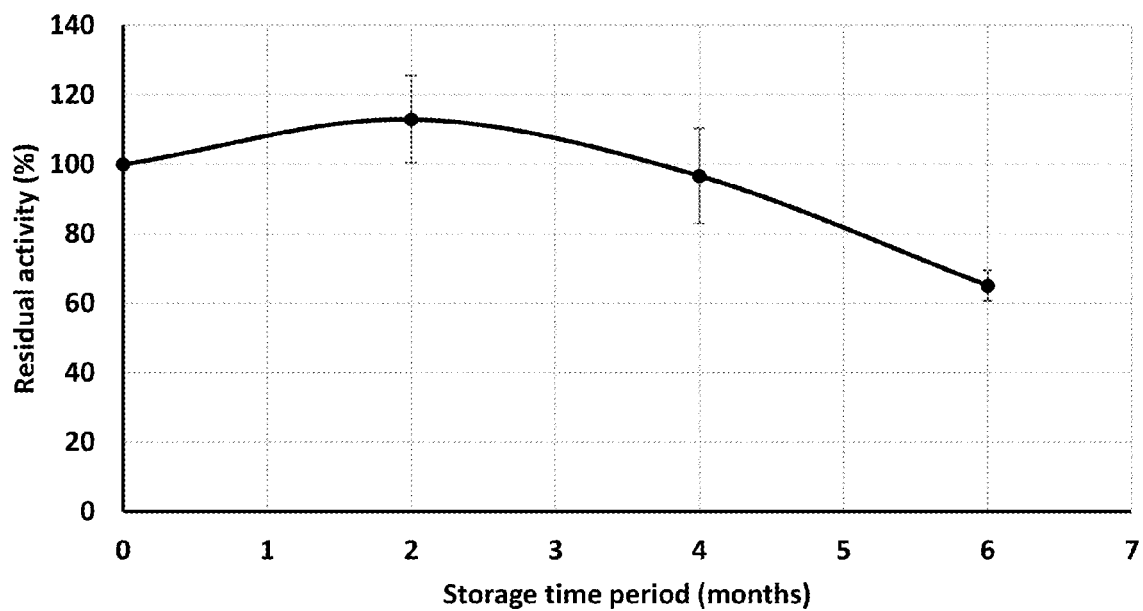

FIG. 12 shows the long term stability of recombinant KrCUT in stabilisation buffer.

Figure 13:
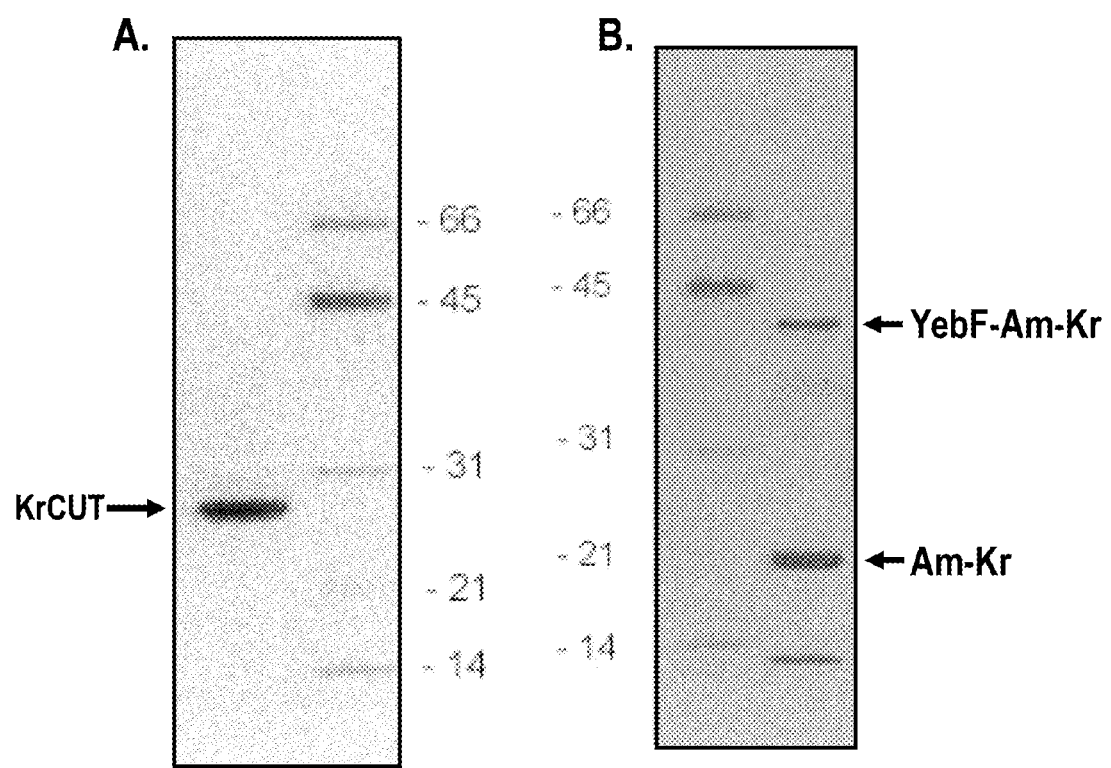

FIG. 13 shows examples of purified recombinant proteins separated by SDS-PAGE. Panel (A) shows the enzyme KrCUT, while panel (B) shows the variant "Am—Kr" alone or fused to the heterologous carrier protein, YebF ("YebF—Am—Kr").

Figure 14:
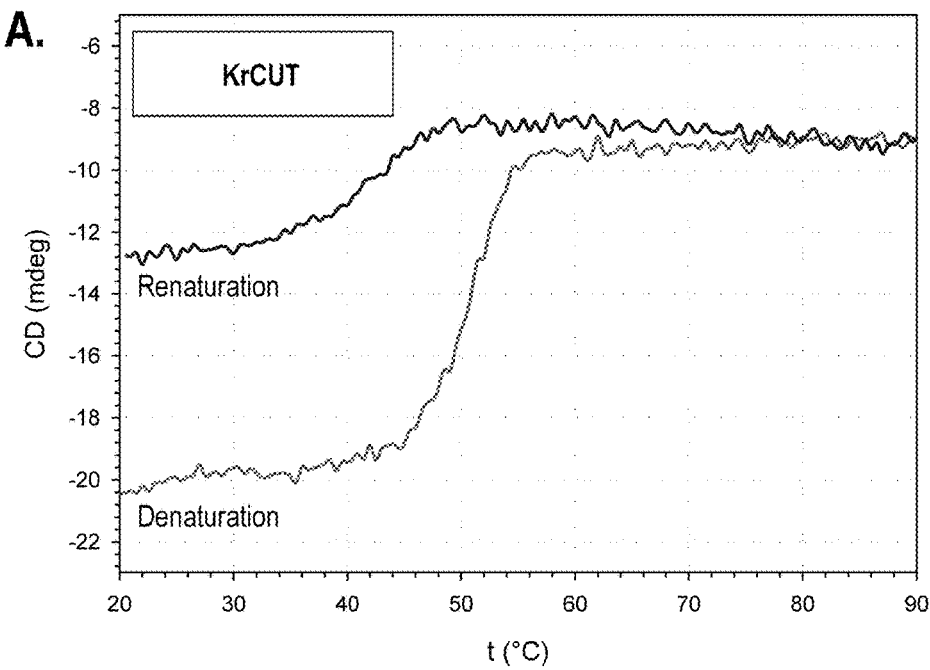
Figure 14:
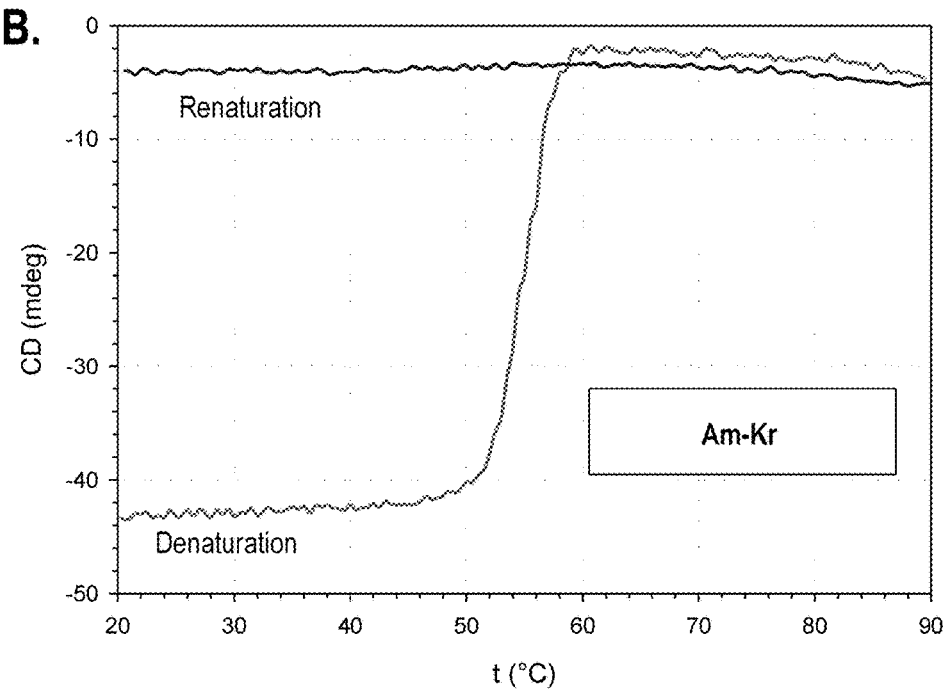
Figure 14:
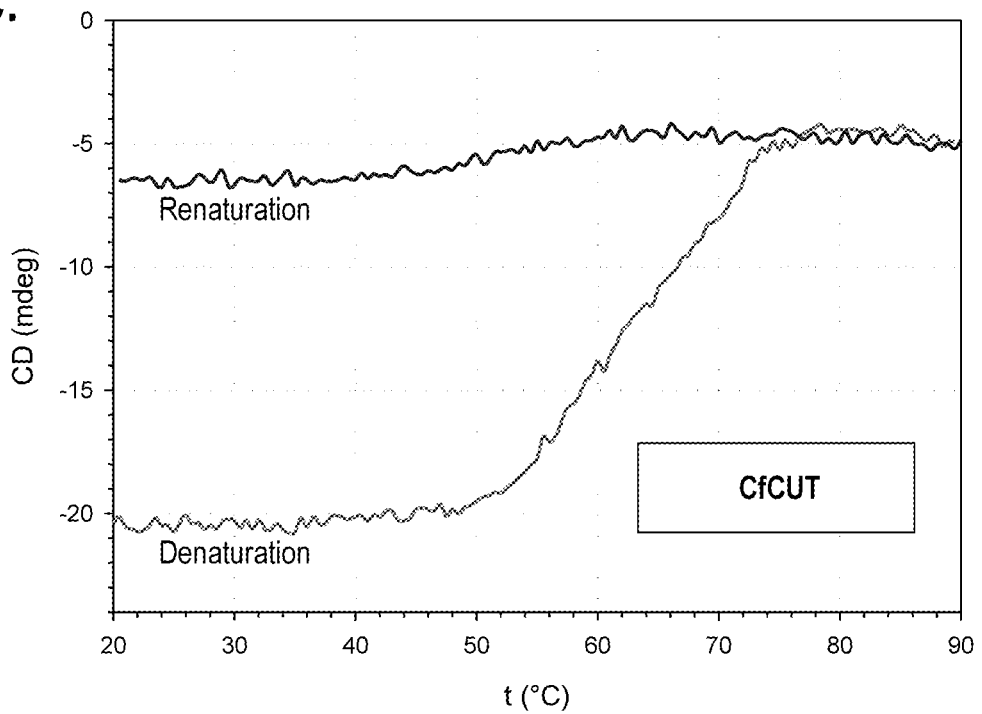
Figure 14:
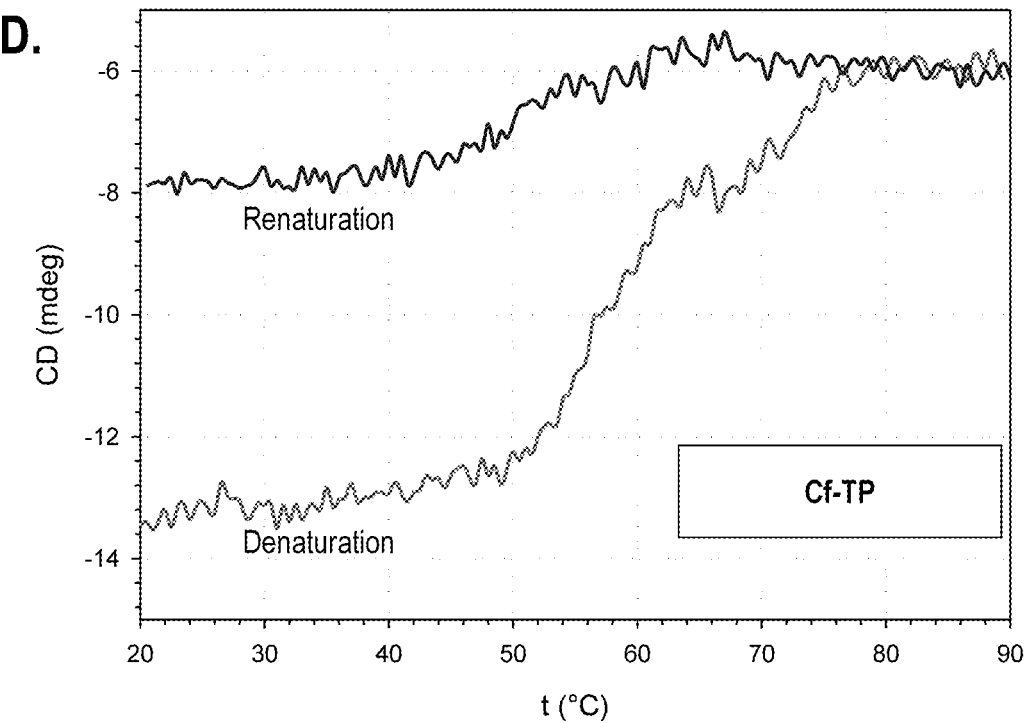

FIG. 14 shows CD spectroscopy measurements in order to monitor the unfolding/refolding of various recombinant proteins: (A) KrCUT; (B) Am—Kr; (C); CfCUT; and (D) Cf-TP.

FIG. 15 shows a multiple sequence alignment (A) and a phylogenic tree (B) of native multi-domain cutinases from *Kineococcus radiotolerans, Cellulomonas bogoriensis, Cellulomonas cellasea*, and *Cellulomonas flavigena*.

SEQUENCE LISTING

This application contains a Sequence Listing in computer readable form entitled Sequence_Listing.txt, created Jan. 28, 2016 having a size of 84 kb. The computer readable form is incorporated herein by reference.

| SEQ ID NO: | Description |
|---|---|
| SEQ ID NO: 1 | ssKrCUT amino acid sequence |
| SEQ ID NO: 2 | KrCUT189 amino acid sequence (cutinase catalytic domain of KrCUT) |
| SEQ ID NO: 3 | T/P-rich linker of KrCUT amino acid sequence |
| SEQ ID NO: 4 | Polymer binding domain of KrCUT amino acid sequence |
| SEQ ID NO: 5 | DNA encoding KrCUT optimized for expression in *E. coli* |
| SEQ ID NO: 6 | KrCUT amino acid sequence, lacking residues 1-33 of ssKrCUT |
| SEQ ID NO: 7 | DNA encoding YebF |
| SEQ ID NO: 8 | YebF amino acid sequence |
| SEQ ID NO: 9 | DNA encoding YebF-KrCUT |
| SEQ ID NO: 10 | YebF-KrCUT amino acid sequence |
| SEQ ID NO: 11 | DNA encoding YebF-KrCUT189 |
| SEQ ID NO: 12 | YebF-KrCUT189 amino acid sequence |
| SEQ ID NO: 13 | ssCfCUT: cutinase from Cf amino acid sequence |
| SEQ ID NO: 14 | ssCbCUT1: cutinase from Cb amino acid sequence |
| SEQ ID NO: 15 | ssCcCUT: cutinase from Cc amino acid sequence |
| SEQ ID NO: 16 | ssAmCUT: cutinase from Am ATCC 39116 amino acid sequence |
| SEQ ID NO: 17 | ssFrCUT: cutinase from Fr amino acid sequence |
| SEQ ID NO: 18 | ssAcCUT: cutinase from Ac 431 amino acid sequence |
| SEQ ID NO: 19 | ssCaCUT: cutinase from Ca amino acid sequence |
| SEQ ID NO: 20 | ssRhCUT: cutinase from Rh amino acid sequence |
| SEQ ID NO: 21 | CfKr fusion protein amino acid sequence |
| SEQ ID NO: 22 | DNA encoding CfKr fusion protein |
| SEQ ID NO: 23 | KrCf fusion protein amino acid sequence |
| SEQ ID NO: 24 | DNA encoding KrCf fusion protein |
| SEQ ID NO: 25 | ssCbCUT2: cutinase from Cb 69B4 (KGM14008.1) amino acid sequence |
| SEQ ID NO: 26 | AmCUT: cutinase from Am ATCC 39116 amino acid sequence |
| SEQ ID NO: 27 | Am-Kr: variant amino acid sequence |
| SEQ ID NO: 28 | CfCUT: cutinase from Cf amino acid sequence |
| SEQ ID NO: 29 | Cf-TP: variant amino acid sequence |
| SEQ ID NO: 30 | cutinase catalytic domain of CfCUT amino acid sequence |
| SEQ ID NO: 31 | T/P-rich linker domain of CfCUT amino acid sequence |
| SEQ ID NO: 32 | polymer binding domain of CfCUT amino acid sequence |
| SEQ ID NO: 33 | cutinase catalytic domain of CbCUT1 (KGM14009.1) amino acid sequence |
| SEQ ID NO: 34 | linker of CbCUT1 (KGM14009.1) amino acid sequence |
| SEQ ID NO: 35 | polymer binding domain of CbCUT1 (KGM14009.1) amino acid sequence |
| SEQ ID NO: 36 | cutinase catalytic domain of CbCUT2 (KGM14008.1) amino acid sequence |
| SEQ ID NO: 37 | T/P-rich linker of CbCUT2 (KGM14008.1) amino acid sequence |
| SEQ ID NO: 38 | polymer binding domain of CbCUT2 (KGM14008.1) amino acid sequence |
| SEQ ID NO: 39 | cutinase catalytic domain of CcCUT (DSM 20118) amino acid sequence |
| SEQ ID NO: 40 | T/P-rich linker of CcCUT (DSM 20118) amino acid sequence |
| SEQ ID NO: 41 | polymer binding domain of CcCUT (DSM 20118) amino acid sequence |
| SEQ ID NO: 42 | cutinase catalytic domain of FrCUT (BMG5.12) amino acid sequence |
| SEQ ID NO: 43 | cutinase catalytic domain of AcCUT (431) amino acid sequence |
| SEQ ID NO: 44 | cutinase catalytic domain of CaCUT (DSM 44712) amino acid sequence |
| SEQ ID NO: 45 | cutinase catalytic domain of RhCUT amino acid sequence |
| SEQ ID NO: 46 | CbCUT2: cutinase from Cb (KGM14008.1) amino acid sequence |
| SEQ ID NO: 47 | CcCUT: cutinase from CcCUT (DSM 20118) amino acid sequence |
| SEQ ID NO: 48 | CbCUT1: cutinase from CbCUT1 (KGM14009.1) amino acid sequence | ss = native N-terminal signal sequence
Kr = *Kineococcus radiotolerans*
Cf = *Cellulomonas flavigena*
Cb = *Cellulomonas bogoriensis*
Cc = *Cellulomonas cellasea*
Am = *Amycolatopsis* sp.
Fr = *Frankia* sp. BMG5.12
Ac = *Actinoplanes missouriensis*
Ca = *Cryptosporangium arvum*
Rh = *Rhodococcus*
TP = threonine/proline-rich linker domain from Kr

DESCRIPTION OF ILLUSTRATIVE EMBODIMENTS

Recombinant Proteins

In one aspect, the present description relates to an isolated multi-domain recombinant protein having cutinase activity. The multi-domain recombinant protein may comprise: (a) a cutinase catalytic domain; (b) a proline/threonine-rich linker domain positioned C-terminal of domain (a); and (c) a polymer binding domain positioned C-terminal of domain (b).

As used herein, the expression "cutinase catalytic domain" refers to a polypeptide domain that has the ability to hydrolyze cutin (and/or another polymer substrate of interest hydrolyzable by the cutinase catalytic domain) in a modular fashion (i.e., when present within a larger recombinant polypeptide of the present invention).

In some embodiments, the cutinase catalytic domain may be: (1) a cutinase catalytic domain having at least 50%, at least 55%, at least 60%, at least 65%, at least 70%, at least 75%, at least 80%, at least 85%, at least 90%, or at least 95% sequence identity of SEQ ID NOs: 2, 30, 33, 36, 39, or 42-45; (2) a cutinase catalytic domain comprising the amino acid sequence of SEQ ID NOs: 2, 30, 33, 36, 39, or 42-45; or (3) both (1) and (2).

In some embodiments, the cutinase catalytic domain may share at least 50%, at least 55%, at least 60%, at least 65%, at least 70%, at least 75%, at least 80%, at least 85%, at least 90%, or at least 95% sequence identity to the cutinase catalytic domain of any one of SEQ ID NOs: 2 and 13-21.

As used herein, the expression "threonine/proline-rich linker domain" or "proline/threonine-rich linker domain" (T/P-rich linker domain) refers to a polypeptide domain that shares functional and/or structural similarity to T/P-rich linker domains found in native multi-domain cutinases, such as those described herein from *Kineococcus radiotolerans* (e.g., accession ABS05574.1), *Cellulomonas flavigena* (e.g., accession ADG75999.1), *Cellulomonas bogoriensis* (e.g., accessions KGM14008.1), and *Cellulomonas cellasea* (e.g., accession KGM03336.1).

In some embodiments, the T/P-rich linker domain may be a threonine/proline-rich linker domain having at least 50%, at least 55%, at least 60%, at least 65%, at least 70%, at least 75%, at least 80%, at least 85%, at least 90%, or at least 95% sequence identity to SEQ ID NO: 3, 31, 34, 37, or 40. In some embodiments, the T/P-rich linker domain may be a T/P-rich linker domain comprising the amino acid sequence of SEQ ID NO: 3, 31, 34, 37, or 40.

In some embodiments, the T/P-rich linker domain may be a polypeptide domain which has at least 20%, at least 25%, at least 30%, at least 35%, at least 40%, at least 50%, at least 55%, at least 60%, or at least 65% of its residues being a proline or a threonine, over a stretch of 15 to 55 consecutive amino acids.

In some embodiments, the linker domain may comprise an amino acid sequence sharing at least 50%, at least 55%, at least 60%, at least 65%, at least 70%, at least 75%, at least 80%, at least 85%, at least 90%, or at least 95% sequence identity to: SEQ ID NO: 3; residues 220-247 of SEQ ID NO: 13; residues 226-236 of SEQ ID NO: 14; or residues 228-276 of SEQ ID NO: 15.

As used herein, the expression "polymer binding domain" refers to a protein domain that may have the ability to bind in a modular fashion (i.e., when present within a larger recombinant polypeptide of the present description) to a given polymer of interest (e.g., a polyester hydrolyzable by a cutinase catalytic domain of the present description).

In some embodiments, the polymer binding domain may have at least 50%, at least 55%, at least 60%, at least 65%, at least 70%, at least 75%, at least 80%, at least 85%, at least 90%, or at least 95% sequence identity to SEQ ID NO: 4, 32, 35, 38, or 41. In some embodiments, the polymer binding domain may comprise the amino acid sequence of SEQ ID NO: 4, 32, 35, 38, or 41.

In some embodiments, the polymer binding domain of a polypeptide of the present description may bind to poly (hydroxybutyrate), triacin, tributyrin, trimiristin, tripalmitin, polyvinyl acetate (PVA), polyethylene terephthalate (PET), or polytrimethylene terephthalate (PTT). In some embodiments, the polymer binding domain may comprise an amino acid sequence sharing at least 50%, at least 55%, at least 60%, at least 65%, at least 70%, at least 75%, at least 80%, at least 85%, at least 90%, or at least 95% sequence identity to the polymer binding domain of any one of SEQ ID NOs: 4 and 13-15. In some embodiments, the polymer binding domain comprises the amino acid sequence of any one of SEQ ID NOs: 4 and 13-15.

In some embodiments, an isolated recombinant protein of the present description may be a chimeric recombinant protein, wherein at least one of domains (a), (b) and (c) is from a cutinase belonging to a different species. Native multi-domain cutinases can be found in species such as *Kineococcus radiotolerans* (e.g., accession ABS05574.1), *Cellulomonas flavigena* (e.g., accession ADG75999.1), *Cel-lulomonas bogoriensis* (e.g., accessions KGM14008.1 and KGM14009.1), or *Cellulomonas cellasea* (e.g., accession KGM03336.1).

In some embodiments, the above mentioned protein further comprises a polymer binding domain operably linked to the cutinase catalytic domain. As used herein, the expression "operably linked" refers to the covalent linkage of two or more modular protein domains (e.g., a cutinase catalytic domain and a polymer binding domain) such that each of the modular protein domains at least substantially retains its enzymatic activity. Two or more protein domains that cooperate synergistically when covalently linked is also within the meaning of "operably linked" as used herein.

In some embodiments, the above mentioned cutinase domain and the above mentioned polymer binding domain are operably linked by a linker domain. In some embodiments, the linker domain is 5 to 60, 5 to 50, 5 to 40, 5 to 30, 5 to 20, 10 to 60, 10 to 50, or 10 to 40 amino acids in length. In some embodiments, the linker domain is a proline/threonine-rich linker domain. As used herein, the expression "proline/threonine-rich" refers to a polypeptide domain which has at least 20%, at least 25%, at least 30%, at least 35%, at least 40%, at least 50%, at least 55%, at least 60%, or at least 65% of its residues being a proline or a threonine. In some embodiments, the linker domain comprises an amino acid sequence sharing at least 50%, at least 55%, at least 60%, at least 65%, at least 70%, at least 75%, at least 80%, at least 85%, at least 90%, or at least 95% sequence identity to: SEQ ID NO: 3; residues 220-247 of SEQ ID NO: 13; residues 226-236 of SEQ ID NO: 14; or residues 228-276 of SEQ ID NO: 15.

In another aspect, the present invention relates to isolated recombinant proteins sharing a minimum threshold of amino acid sequence identity with any one of the polypeptides as described herein. In specific embodiments, the present invention relates to isolated polypeptides having at least 60%, 65%, 70%, 71%, 72, 73%, 74%, 75%, 76%, 77%, 78%, 79, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to any one of the above-mentioned polypeptides. Other specific percentage units that have not been specifically recited here for brevity are nevertheless considered within the scope of the present invention.

In some embodiments, the isolated recombinant protein of the present description may have improved stability to a bleaching agent, as compared to a native cutinase enzyme that comprises the corresponding cutinase catalytic domain. As used herein, a "bleaching agent" refers to an agent that lightens or whitens a substrate through chemical reaction. Bleaching reactions usually involve oxidative or reductive processes that degrade color. As used in the present context, "increased stability" refers to an enzyme that generally retains a higher relative level of enzymatic activity, or exhibits a lower relative loss of enzymatic activity, after being exposed to increasing concentrations of a given bleaching agent, as compared to a suitable control enzyme (e.g., native enzyme).

In some embodiments, the bleaching agent may be an oxidizing agent or a reducing agent. The oxidizing agent may include hydrogen peroxide, a peroxide other than hydrogen peroxide, a non-peroxide oxidizing agent, ozone, sodium percarbonate, sodium perborate, or any combination thereof. The reducing agent may include sodium dithionite, sodium dithionite, sulfur dioxide, a sulfite, a bisulfite, a sodium borohydride, or any combination thereof.

In some embodiments, the isolated recombinant protein of the present description retains activity in the presence of a chelator (e.g., EDTA or GLDA). In some embodiments, the isolated recombinant protein of the present description retains activity in the presence of EDTA at a concentration of between 0.5%, 1%, 2%, 3%, 4%, 5%, 6%, 7%, 8%, or 9%, and 10% w/v). In some embodiments, the isolated recombinant protein of the present description retains activity in the presence of GLDA at a concentration between 0.5%, 1%, 2%, 3%, or 4%, and 5% w/v).

In some embodiments, the isolated recombinant protein of the present description may have improved stability to an organic solvent (e.g., methanol, 2-propanol, or another alcohol, dimethyl sulfoxide (DMSO), dimethylformamide (DMF), acetone, or any combination thereof), as compared to a native cutinase enzyme that comprises the corresponding cutinase catalytic domain. As used in the present context, "increased stability" refers to an enzyme that generally retains a higher relative level of enzymatic activity, or exhibits a lower relative loss of enzymatic activity, after being exposed to increasing concentrations of a given organic solvent, as compared to a suitable control enzyme (e.g., native enzyme).

In some embodiments, the isolated recombinant protein of the present description may exhibit a broader temperature activity range, as compared to a native cutinase enzyme that comprises the corresponding cutinase catalytic domain. Such properties may increase the versatility of an enzyme for industrial applications. As used in the present context, "broader temperature activity range" refers to an enzyme that generally retains a higher relative level of enzymatic activity, or exhibits a lower relative loss of enzymatic activity, when incubated across a broader range of reaction temperatures, as compared to a suitable control enzyme (e.g., native enzyme). This is in contrast to an enzyme that, for example, shows a maximal level of activity at a given optimal temperature, but exhibits a relatively sharp decrease in activity when the reaction temperature is progressively shifted away from that optimal temperature.

It will be appreciated that this disclosure embraces the degeneracy of codon usage as would be understood by one of ordinary skill in the art and as illustrated in the table below.

| Codon Degeneracies | |
| --- | --- |
| Amino | Codons |
| Ala/A | GCT, GCC, GCA, GCG |
| Arg/R | CGT, CGC, CGA, CGG, |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

Conservative substitutions: Furthermore, it will be understood by one skilled in the art that conservative substitutions may be made in the amino acid sequence of a polypeptide without disrupting the structure or function of the polypeptide. Conservative substitutions are accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins. The table below provides an exemplary list of conservative substitutions.

| Conservative Substitutions | |
| --- | --- |
| Type of Amino Acid | Substitutable Amino Acids |
| Hydrophilic | Ala, Pro, Gly, Glu, Asp, Gln, Asn, Ser |
| Sulphydryl | Cys |
| Aliphatic | Val, Ile, Leu, Met |
| Basic | Lys, Arg, His |
| Aromatic | Phe, Tyr, Trp |

In another embodiment, the present invention relates to functional variants of the recombinant proteins as described herein. "Functional variants" refers to recombinant proteins differing from their parent recombinant protein by one or more amino acid substitutions, deletions, and/or insertions, yet which at least retain or provide higher biological activity as compared to their parent recombinant protein. Functional variants include functional fragments (i.e., biologically active fragments) of any one of the recombinant polypeptides of e present invention. Such fragments include fewer amino acids than the full length protein from which they are derived, but exhibit at least one biological activity of the corresponding full-length protein.

In another aspect, the present invention includes fusion proteins comprising a polypeptide of the present invention or a functional variant thereof, which is operatively linked to one or more unrelated polypeptide (e.g., heterologous amino acid sequences). "Unrelated polypeptides" or "heterologous polypeptides" or "heterologous sequences" refer to polypeptides or sequences which are usually not present close to or fused to one of the polypeptides of the present invention. Such "unrelated polypeptides" or "heterologous polypeptides" having amino acid sequences corresponding to proteins which are not substantially homologous to the polypeptide sequences disclosed herein. Such "unrelated polypeptides" can be derived from the same or a different organism. In one embodiment, a fusion protein of the present invention comprises at least two biologically active portions or domains of polypeptide sequences disclosed herein.

In another embodiment, a recombinant protein of the present invention can be fused to a protein which enables or facilitates recombinant protein purification and/or detection. For example, a polypeptide of the present invention can be fused to a protein such as glutathione S-transferase (GST), and the resulting fusion protein can then be purified/detected through the high affinity of GST for glutathione. In another embodiment, a recombinant protein of the present invention can be fused or otherwise operably linked to a carrier protein (e.g., YebF) which enables its extracellular secretion. Such a linkage can be made such the carrier protein is cleavable upon secretion of the recombinant protein of the present invention.

Recovery and Purification

In another aspect, polypeptides of the present invention may be present alone (e.g., in an isolated or purified form), within a composition including a carrier (e.g., an enzymatic composition for carrying out an industrial process), or in an appropriate host. In one embodiment, polypeptides of the present invention can be recovered and purified from cell cultures (e.g., recombinant cell cultures) by methods known in the art. In another embodiment, high performance liquid chromatography ("HPLC") can be employed for the purification.

In another aspect, polypeptides of the present invention include naturally purified products, products of chemical synthetic procedures, and products produced by recombinant techniques from a prokaryotic or eukaryotic host, including, for example, bacterial, yeast, fungal, plant, insect, animal and mammalian cells. Depending on the host employed in a recombinant production procedure, the polypeptides of the present invention may be glycosylated or may be non-glycosylated. In addition, polypeptides of the invention may also include an initial modified methionine residue, in some cases as a result of host-mediated processes.

Polynucleotides

In some aspects, the present description relates to polynucleotides encoding the recombinant proteins described herein. In some embodiments, the recombinant protein encoded by said polynucleotide may lack an N terminal signal sequence often found on native cutinases. The recombinant truncation of such native N terminal signal sequences may increase the enzymatic activity, and thus the utility of the recombinant enzyme.

In some embodiments, the polynucleotides of the present description may encode a recombinant protein described herein which is fused to a heterologous carrier protein (e.g., YebF) and/or a heterologous tag (e.g., a purification or detection tag). Such fusions may not only enable the proper expression and/or secretion of the recombination protein from a host production cell, but also may facilitate the autolysis of recombination proteins over time, which may result in truncated enzyme having higher activity and/or increased structural stability.

In some embodiments, the polynucleotides described here may be fused to a heterologous promoter to improve their expression in a host production cell.

In some aspects, the present invention relates to a polynucleotide encoding a recombinant protein as described herein. In some embodiments, the polynucleotide may be RNA or DNA (e.g., cDNA).

In another aspect, the present invention relates to isolated polynucleotides sharing a minimum threshold of nucleic acid sequence identity with any one of the polynucleotides as described herein. In specific embodiments, the present invention relates to isolated polynucleotides having at least 60%, 65%, 70%, 71%, 72, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% nucleic acid sequence identity to any one of the polynucleotides as described herein. Other specific percentage units that have not been specifically recited here for brevity are nevertheless considered within the scope of the present invention. Polynucleotides having the aforementioned thresholds of nucleic acid sequence identity can be created by introducing one or more nucleotide substitutions, additions or deletions into the coding nucleotide sequences of the present invention such that one or more amino acid substitutions, deletions or insertions are introduced into the encoded polypeptide. Such mutations may be introduced by standard techniques, such as site-directed mutagenesis and PCR-mediated mutagenesis.

In some aspects, the present invention relates to a vector comprising a polynucleotide as described herein operably linked to a heterologous promoter. As used herein in the context of polynucleotides, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e., that transcribable polynucleotide molecule is not naturally occurring operably linked in combination with that promoter molecule. In some embodiments, the promoter may be a constitutively active promoter, or may be an inducible promoter. In some embodiments, the promoter may be a viral promoter, bacterial cell promoter, a yeast cell promoter, a fungal cell promoter, an insect cell promoter, an animal cell promoter, or a mammalian cell promoter. A heterologous promoter may be a synthetic promoter that differs from an endogenous promoter by the addition, deletion or substitution of one or more nucleotides.

Vectors

Another aspect of the invention pertains to vectors (e.g., expression vectors), containing a polynucleotide encoding a polypeptide of the present invention. As used herein, the term "vector" includes a nucleic acid molecule capable of transporting another nucleic acid molecule to which it has been linked.

Cells

In another aspect, the present description features cells, e.g., transformed host cells or recombinant host cells that contain a polynucleotide or vector described herein. A "transformed cell" or "recombinant cell" is a cell into which (or into an ancestor of which) has been introduced a polynucleotide or vector of the present description by means of recombinant DNA techniques. Both prokaryotic and eukaryotic cells may be included, e.g., a bacterial cell, a yeast cell, a non-yeast fungal cell (e.g., a filamentous fungus), an insect cell, a plant cell, an animal cell, or a mammalian cell. In some embodiments, the cells may be from *E. coli, Bacillus subtilis*, or *Streptomyces* spp.

Expression of Transgenic Proteins

Several experiments were conducted trying to express KrCUT as well as other recombinant proteins in *E. coli*. Various vectors were tested with the codon-optimized gene of krCUT including and excluding the enzyme's natural signal sequence to express the protein intracellular. Extensive growth and induction conditions were tested but all experiments yielded very low or no expression of the protein.

However, it has presently been found that expression of the KrCUT protein could be achieved by the fusion of KrCUT to the YebF protein. This strategy yielded reproducible protein expression and secretion.

The active proteins (confirmed by N-terminal sequencing) have an insertion of two amino acids (leucine and glutamine) that have been introduced as linkers between YebF and the natural occurring KrCUT and KrCUT206 sequence, respectively. In the mature expressed protein, those two amino acids are not cleaved off through the autocatalytic action of the enzyme but remain on the protein's N-terminus.

Monitoring the protein after production reveals a cleavage of the N-terminal fused YebF protein which also results in an increase in enzyme activity (about 5 times). At the same time this N-terminal protein cleavage appears to be a slow process which is not related to protease activity but rather to autocatalytic protein hydrolysis as it occurs also in a purified protein solution.

Protein fractions after purification on SP-Sepharose™ contain KrCUT or other recombinant enzymes described herein with and without intact YebF-N-terminal fusion, which can be separated using size exclusion chromatography. Over time, the proteins undergo a change in the protein patterns by completely losing the fusion protein YebF. After storage for several weeks at 4° C. The only protein band left is KrCUT (or other recombinant proteins lacking the YebF carrier protein) showing a single protein band which consists now exclusively of the truncated recombinant protein.

Uses & Compositions

In some aspects, the present description relates to a composition comprising (i) the isolated recombinant protein as defined herein; and (ii) an additive. As used herein, an "additive" refers to an agent that, when added to a composition of the present description, increases performance, stability, and/or shelf-life, as compared to a composition comprising the recombinant protein alone.

In some aspects, the present description relates to a composition comprising (i) the isolated recombinant protein as defined herein; and (ii) a bleaching agent and/or an organic solvent, wherein said recombinant protein retains said cutinase activity when present in said composition.

In some embodiments, the composition may be a "ready to use" formulation wherein the bleaching agent may be present at a concentration of at least 100 ppm, 150 ppm, 200 ppm, 250 ppm, 300 ppm, 350 ppm, 400 ppm, 450 ppm, 500 ppm, 550 ppm, 600 ppm, 650 ppm, 700 ppm, 750 ppm, 800 ppm, 850 ppm, 900 ppm, 950 ppm, 1000 ppm, 1500 ppm, 2000 ppm, 2500 ppm, 3000 ppm, 3500 ppm, 4000 ppm, 4500 ppm, 5000 ppm, 5500 ppm, 6000 ppm, 6500 ppm, or 7000 ppm. In some embodiments, the bleaching agent may be present at a concentration of between 100 ppm, 150 ppm, 200 ppm, 250 ppm, 300 ppm, 350 ppm, 400 ppm, 450 ppm, 500 ppm, 550 ppm, 600 ppm, 650 ppm, 700 ppm, 750 ppm, 800 ppm, 850 ppm, 900 ppm, 950 ppm, or 1000 ppm, and 1500 ppm, 2000 ppm, 2500 ppm, 3000 ppm, 3500 ppm, 4000 ppm, 4500 ppm, 5000 ppm, 5500 ppm, 6000 ppm, 6500 ppm, or 7000 ppm.

In some embodiments, the composition may be a dilutable "concentrate" wherein the bleaching agent may be present at a concentration of at least 3%, 4%, 5%, or 6% v/v.

In some embodiments, the bleaching agent may be an oxidizing agent or a reducing agent. The oxidizing agent may include hydrogen peroxide, a peroxide other than hydrogen peroxide, a non-peroxide oxidizing agent, ozone, sodium percarbonate, sodium perborate, or any combination thereof. The reducing agent may include sodium dithionite, sodium dithionite, sulfur dioxide, a sulfite, a bisulfite, a sodium borohydride, or any combination thereof.

In some embodiments, the organic solvent may be: methanol, 2-propanol, or another alcohol, dimethyl sulfoxide (DMSO), dimethylformamide (DMF), or acetone. In some embodiments, the organic solvent may be present at a concentration of at least 1%, 2%, 3%, 4%, 5%, 6%, 7%, 8%, 9%, 10%, 15%, 20%, 25%, 30%, 35%, 40%, 45%, or 50% v/v. In some embodiments, the organic solvent may be present at a concentration of between 1%, 2%, 3%, 4%, 5%, 6%, 7%, 8%, 9%, 10%, 15%, 20%, or 25%, and 30%, 35%, 40%, 45%, or 50% v/v. In some embodiments, the organic solvent is DMSO and is present at a maximum concentration of 50% v/v. In some embodiments, the organic solvent is acetone and is present at a maximum concentration of 30% v/v.

In some embodiments, the compositions of the present description may comprise one or more an additional recombinant enzyme(s). Examples of such additional recombinant enzymes may include: a lipase, an esterase, a pectate lyase, a pectinase, a cutinase, a cellulase, a hemicellulose, an amylase, or any combination thereof. In some embodiments, the composition does not comprise a protease that degrades or inactivates a recombinant protein as defined herein. In some embodiments, the composition comprises a protease and a stabilizer (e.g., a polyol and/or boric acid).

In some embodiments, the compositions of the present description may comprise one or more additives such as a detergent; a surfactant; a buffer; a chelator (e.g., EDTA or GLDA); a stabilizer; or any combination thereof. In some embodiments, the composition comprises EDTA (ethylenediaminetetraacetic acid) at a concentration of between 0.5%, 1%, 2%, 3%, 4%, 5%, 6%, 7%, 8%, or 9%, and 10% w/v. In some embodiments, the composition comprises GLDA (L-Glutamic acid N,N-Diacetic acid Tetra sodium) at a concentration between 0.5%, 1%, 2%, 3%, or 4%, and 5% w/v). In some embodiments, the composition comprises GLDA at a concentration of at least 0.5%, 1%, 2%, 3%, 4%, 5%, 6%, 7%, 8%, 9%, or 10% w/v). In some embodiments, the composition comprises GLDA at a concentration of at least 0.5%, 1%, 2%, 3%, 4%, 5%, 6%, 7%, 8%, 9%, or 10% w/v).

In some embodiments, the compositions may comprise an additive which is a stabilization buffer comprising one or more of sodium gluconate (e.g., 1-5% v/v), sodium carbonate (e.g., 1-5% v/v), sodium citrate (e.g., 1-5% v/v), and propylene glycol (e.g., 1-5% v/v). In some embodiments, the compositions may comprise a stabilization buffer comprising one or more of a polyol such as propylene glycol and glycerol, boric acid and boron derivatives, and sodium formate. In some embodiments, the composition comprises a polyol and/or boric acid. In some embodiments, the compositions of the present description may be: a cleaning product, a degreaser, a disinfectant, a bleaching product, or any combination thereof; or feed or a feed additive.

In some embodiments, the present description relates to the use of the isolated recombinant protein as defined herein, or the composition as defined herein, for: (i) cleaning, degreasing, disinfecting, bleaching, biofilm control, or any combination thereof; (ii) for inactivating mycotoxin (e.g., ochratoxin and/or aflatoxin); (iii) bioscouring or other treatment of fabrics or textiles; (iv) catalyzing trans-esterification reactions; (v) vegetable oil extraction; or (vi) enhanced oil recovery.

In some embodiments, the present description relates to the isolated recombinant protein as defined herein, or the composition as defined herein, for use in: (i) cleaning, degreasing, disinfecting, bleaching, biofilm control, or any combination thereof; (ii) for inactivating mycotoxin; (iii) bioscouring or other treatment of fabrics or textiles; (iv) catalyzing trans-esterification reactions; (v) vegetable oil extraction; or (vi) enhanced oil recovery.

In some embodiments, the present description relates to the use of the isolated recombinant protein as defined herein, or the composition as defined herein, for the manufacture of an industrial product for: (i) cleaning, degreasing, disinfecting, bleaching, biofilm control, or any combination thereof; (ii) for inactivating mycotoxin; (iii) bioscouring or other treatment of fabrics or textiles; (iv) catalyzing trans-esterification reactions; (v) vegetable oil extraction; or (vi) enhanced oil recovery.

In some embodiments, the present description relates to a kit comprising a recombinant protein as defined herein and a suitable container. In some embodiments, the kit may be for one or more of the above mentioned uses.

In some aspects, the present invention relates to the use of a recombinant protein as described herein for inactivating mycotoxin.

In some aspects, polypeptides of the present invention may be useful for mycotoxin detoxification (mycotoxin inactivation). Advantageously, and unlike some other fungal cutinases that may have been used for mycotoxin detoxification, polypeptides of the present invention may be useful for inactivating more than one mycotoxin. In some embodiments, polypeptides of the present invention may be useful for inactivating Ochratoxin. In some embodiments, polypeptides of the present invention may be useful for inactivating Aflatoxin. In some embodiments, polypeptides of the present invention may be useful for inactivating both Ochratoxin and Aflatoxin (e.g., from the fungi strains *Aspergillus flavus* and/or *Aspergillus niger*).

In some aspects, the present invention relates to a kit for inactivating mycotoxins, said kit comprising a recombinant protein of the present invention as defined herein; and a suitable container.

In some aspects, the present invention relates to the use of a recombinant protein as described herein for degrading a polymer. In some embodiments the polymer is a homopolymer or a heteropolymer. In some embodiments, the polymer is a polyester. In some embodiments, the polymer is: cutin; polycaprolactone (PCL); polylactic acid (PLA); poly(1,3-propylen adipate) (PPA); poly(hydroxybutyrate); triacin; tributyrin; trimiristin; tripalmitin; polyvinyl acetate (PVA); polyethylene terephthalate (PET); or polytrimethylene terephthalate (PTT).

In other embodiments, polypeptides of the present invention may be employed with one or more other enzymes (e.g., pectate lyase) for the degradation/hydrolysis of a polymer of interest.

Applications of the recombinant proteins of the present invention in industries such as food, laundry/detergent, textiles, recycling, and/or polymer manufacturing are also envisioned. In some aspects, the present invention may relate to the use of a recombinant protein as described herein in cleaners/degreasers (industrial and/or domestic); animal feed; the treatment of surface in the pulp and paper industries; and/or in the degradation/control of biofilm.

The present invention is illustrated in further details by the following non-limiting examples.

Example 1

Material and Methods 1.1 Reagents and Chemicals.

p-Nitrophenyl (pNP)-esters were purchased from Fluka (Steinheim, Germany) or from Sigma-Aldrich (USA). Lactic acid, 6-hydroxyhexanoic acid, adipic acid, polycaprolactone (PCL; $M_n$=42500; $M_w$=65000), polylactic acid (PLA; $M_n$=30000; $M_w$=60000), poly(1,3-propylen adipate) (PPA; $M_n$=42500; $M_w$=4800), and poly(R)-3-hydroxybutyrate (PHB) were purchased from Sigma-Aldrich, Fluka or Alfa Aesar (Ward Hill, USA). Restriction endonucleases were from New England Biolabs (Pickering, ON, Canada), T4 DNA ligase was from Roche (Mannheim, Germany) and Titanium DNA polymerase from Clontech (Takara Bio company, USA).

1.2 Protein Expression (Small Scale).

A single colony of *E. coli* JM109 cells harboring either YebF-KrCUT or YebF-KrCUT189 was grown at 30° C. on a rotary shaker at 200 rpm in 10 mL Terrific Broth (TB) medium supplemented with 100 µg/ml ampicillin. The overnight culture was used to inoculate 1 L fresh TB medium, then grown to $OD_{600}$ 0.4-0.5 under the same culture conditions and induced with 0.1 mM IPTG for 16 h. The cells were collected by centrifugation at 6000 rpm for 30 min (Beckman centrifuge, Model J2-21M) and the supernatant was used as a source of cutinase. Protein concentration was determined using the bicinchoninic acid (BCA) method (Smith et al., 1985).

1.3 Fermentation in DASGIP System (Large Scale Protein Expression).

A single colony of *E. coli* JM109 cells harboring either YebF-KrCUT or YebF-KrCUT189 were cultured in LB-media containing ampicillin (0.1 g/L) and incubated at 30° C. in a rotary shaker at 200 rpm overnight. The preculture (5% v/v of the total fermentation volume) was added to TB media (1 L) in a 2 L fermenter (DASGIP, Germany). The temperature was set to 30° C. and the pH was controlled at 7.0 by the addition of concentrated ammonium hydroxide. The cell broth was aerated at 1.0 wm and stirred at 400-900 rpm to maintain 30% dissolved oxygen. If necessary, the airflow was supplemented with oxygen. At an $OD_{600}$ of 9 (~7 h), cutinase expression was induced by the addition of IPTG (final concentration 1 mM); the temperature was set to 25° C., and glucose (33% w/w aqueous solution) was fed at an initial rate of 3 mL/h and gradually increased to 6 mL/h. The cells were harvested after 16 h and centrifugation of the cell broth (6000 rpm, 4° C., 20 min) yielded 0.82 to 0.87 L of supernatant that was used to purify the corresponding cutinase.

1.4 Protein Purification.

All purification procedures were performed at 4° C. on an ÄKTAexplorer™ 100 Air chromatography system (GE Healthcare). Culture supernatant containing active enzyme was concentrated and dialyzed against sodium phosphate buffer (20 mM, pH 7.0) by cross flow filtration using the QuixStand™ system (GE Healthcare) equipped with a hollow fibre cartridge (3 kDa cut-off). The enzyme solution was loaded on a SP-Sepharose™ FF column (XK 50/12) previously equilibrated with 20 mM sodium phosphate buffer (pH 6.0). The flow rate was 4.0 mL/min. The column was washed with the same buffer until no protein could be detected in the flow through, and the enzyme subsequently eluted with a linear gradient of 0-0.6 M NaCl. Active fractions were pooled and concentrated by ultrafiltration (membrane exclusion size 10 kDa, in a 100 mL stirring cell (Amicon, USA) and then applied to a HiLoad™ Superdex 75 prep grade (16/60) column previously equilibrated with 20 mM sodium phosphate buffer (pH 7.0) containing 150 mM NaCl. Protein was eluted with the same buffer at a flow rate of 1.5 mL/min and collected in 2 mL fractions. The protein profile was monitored by its absorbance at 280 nm.

1.5 Protein Sequencing.

Purified enzymes were separated by SDS-PAGE and transferred onto a polyvinylidene difluoride membrane (Bio-RAD, USA). N-terminal sequencing was carried out by the Sheldon Biotechnology Centre (McGill University, Montreal, Canada). Phenylthiohydantoin amino acids were analyzed by HPLC using a reversed-phase column.

1.6 Esterase Assay.

Esterase activity was determined by monitoring the formation of pNP at 410 nm from various pNP-esters using a Beckman UV spectrophotometer (model DU 640) (21). Substrates were dissolved in isopropanol and were added to 50 mM sodium phosphate buffer pH 8.0 to give 10% (v/v) total isopropanol concentration in a 1 mL reaction volume. pNP-butyrate was used at a final concentration of 1.2 mM. For pNP-caprylate, myristate and palmitate, the final concentration ranged from 0.1 to 0.5 mM. The reaction (1 mL) was started by adding an appropriate amount of enzyme. One enzyme unit (U) is defined as the amount of enzyme that produced 1 µmol of product (pNP) per min; specific activity is expressed as U/mg protein. A molar extinction coefficient of 15 $mM^{-1}$ $cm^{-1}$ for pNP is used for calculating enzyme activity.

1.7 Determination of Cutinolytic Activity.

Apple (Golden Delicious) cutin was used as substrate. The outer layer of the fruit was peeled by hand and cutin preparation carried out as described by Gerard et al. (1993) with minor modifications. Discs of apple peels were incubated at 50° C. in oxalate buffer [(oxalic acid (4 g/L)/ammonium oxalate (16 g/L)] for 16 h and then collected and washed several times with deionized water. The sample was treated with 0.5% Novozymes *Aspergillus niger* pectinase (Sigma P2736) in 100 mM phosphate citrate buffer pH 5.8 for 16 h. The cutin sheets were washed with ethanol, followed by several washes with chloroform, and then incubated in chloroform at 45° C. for 16 h, and finally dried to constant weight. The cutin was ground in a Cyclone sample Mill (UDY Corporation, Fort Collings, Colo., USA).

A typical reaction mixture (2 mL) contained 20 mg cutin and an appropriate amount of cutinase in 25 mM sodium phosphate buffer, pH 8.0. The mixture was incubated in a water bath at 37° C. with gentle shaking for 16 h. Assays were conducted in duplicate. At the end of the reaction, the remaining cutin was removed by centrifugation (10 min, 5000 rpm). The resulting solution was acidified with hydrochloric acid and cutin monomers extracted with chloroform/methanol, according to Bligh and Dyer (1959). The organic phase was removed by evaporation under an air stream and the dried residue dissolved in 1 mL chloroform/methanol (85:15) and used for further derivatization. Trimethylsilylation of cutin monomers was performed with BSTFA [N,O-bis(trimethylsilyl) trifluoroactamide] and TMCS (trimethylchlorosilane) provided by the supplier in the ratio 99:1 (Supelco, Bellefonte, USA) at 70° C. for 3 h, and the composition of the mixture determined by GC-MS.

1.8 Analysis of Cutin Monomers by GC-MS.

Cutin monomers were identified by GC-MS on an Agilent 6890 gas chromatography system coupled to a 5973 quadrupole mass spectrometer. 1 µL was injected under splitless condition on a 50 m×0.20 mm×0.33 µm DB-5MS capillary column (Agilent). The oven temperature program was 70° C. (for 1.39 min) to 136° C. at 64° C./min and to 290° C. at 2.5° C./min (for 55 min). Helium was used as carrier gas. The temperature at the injection port was 250° C. The detector was run in EI mode at 70 eV. Masses were scanned between 50 and 650 amu.

Components were identified by comparison of the MS spectra of their trimethylsilyl (TMSi) derivatives, as methyl ester TMSi ether or as TMSi ester TMSi ether, with published spectra (Kallio et al., 2006; Philipps et al., 2002).

1.9 HPLC-Analysis of Monomers after Polymer Degradation.

HPLC analysis was carried out on a Waters system consisting of a model 600 pump and 717 Plus autosampler, equipped with a refractive index detector (Waters, model 2414) or PDA detector (model 2996). Organic acids were analyzed with a Transgenomic ICSep IC—ION-300 (300 mm×7.8 mm OD) column using 0.01N $H_2SO_4$ as mobile phase at a flow rate of 0.4 mL/min at 35° C. Retention times are as follows: lactic acid, 23.2 min; 6-hydroyhexanoic acid, 45.2 min; and adipic acid, 33.4 min.

1.10 Determination of Polymer Degradation by Size Exclusion Chromatography.

Size exclusion chromatography (SEC) was performed using a multi-detection system from Viscotek (Houston, Tex.) consisting of a Model 302 Triple Detector Platform, including a refractive index detector, a four capillary viscometer and a 2 angles laser light scattering detector, and a GPCmax Integrated pump, autosampler, and degasser. Molar masses of the samples were determined with universal calibration with the refractive index detector and the viscosity detector. The universal calibration curve was based on polystyrene standards [Polymer Laboratories (Amherst, Mass.) and Aldrich (Oakville, ON)] using the molar masses determined by the manufacturer and the intrinsic viscosities measured by the apparatus. The software OmniSEC™ software from Viscotek was used for data collection and calibration. Separation in THF was performed by injecting 100 µL of 1.5-2 mg/mL solutions of standards or samples into thermostatically controlled SuperRes™ columns [35° C.; PAS-102, PAS102.5, PAS-103L, each 300 mm×8 mm; Poly-Analytik (London, ON)]. The flow rate was 1 mL/min.

1.11 Degradation of Polyesters.

An appropriate amount of cutinase was added to 20 mg of the polymer to be analyzed (PCL, PLA, PHB, and PPA) in 50 mM phosphate buffer, pH 8. The reaction mixture (2 mL) was shaken at 37° C. at 175 rpm on an orbital shaker. Samples were taken after 1, 3, 6, and 24 h and aliquots of 50 µL were analyzed by HPLC; the remaining mixtures were frozen and subsequently lyophilised. The resulting solid (~40-50 mg) was dissolved in THF, filtered, diluted (1.5-2 mg/mL), and analyzed by SEC.

Alternatively, a thin film was prepared from 1 g of commercial available PCL pellets and used for degradation. The polymer was dissolved in dichloromethane in a 1 L beaker. The solvent was allowed to evaporate overnight and the resulting film dried to constant weight under reduced pressure. Prior to enzymatic treatment the film was cut into pieces (20 mg) of approximately 1.5 cm×1.5 cm and thickness of approximately 0.1 mm. The reaction mixture was monitored by HPLC and SEC as described above.

1.12 Action of KrCUT on Plant Material.

Hemp stems (50 cm, 25 g) were treated enzymatically with KrCUT (100 U/g) together with a cloned pectate lyase (20 U/g) described by Xiao et al. (2008). The reaction was carried out in 50 mM Tris-HCl, pH 8.0 supplemented with 0.5 mM $CaCl_2$ (required for pectate lyase). The samples were incubated at 37° C. with gentle shaking at 100 rpm for 16 h. The stems were removed from the enzymatic solution, peeled off by hand, and the resulting fibre washed with hot water to inactivate the enzymes. After removal of the outer layer debris by rinsing with cold water, the fibres were air-dried. A sample of the hemp stem treated only with pectate lyase was prepared for comparison. These experiments were conducted in duplicate. The dried fibres were spread onto a microscope slide and observed by light microscope. A scanning electron microscopy (SEM) analysis was also conducted using a Hitachi S-4700 at a voltage of 2 kV to observe the fibre surface and also fiber bundle.

1.13 Effect of KrCUT in Removing Pectin from Hemp Fibre.

Hemp fibres (German variety, 150 mg) were treated with either pectate lyase (PL, 10 U) or PL combined with various amounts of KrCUT (40, 60 and 100 U). Control experiments containing no enzyme or 100 U of KrCUT were conducted for comparison. After incubation at 37° C., aliquots of the reaction mixture were taken at 1 h 30 min and 3 h, and analyzed for pectin degradation products using the thiobarbituric acid (TBA) method (52) which detects released unsaturated compounds spectrophotometrically at 550 nm.

1.14 Adsorption Assays.

Adsorption assays were carried out following procedures of Kasuya et al. (1999). Purified KrCUT and KrCUT189 at concentrations ranging from 0.16 to 3.2 mg/mL were added to a suspension of 25 mg PHB in 50 mM sodium phosphate (pH 8.0) in a total volume 1 mL. The mixture was incubated at room temperature with gentle shaking for at least 3 h. The PHB polymer was removed by centrifugation and the concentration of protein in the supernatant was determined by the BCA method. The concentration of bound protein at a particular concentration of cutinase was calculated as the difference between a control without added PHB and free cutinase after incubation with PHB. An isotherm of [Bound] (mg/mg PHB) vs [Free] (mM) was generated and binding parameters were determined by non-linear regression using the Langmuir equation:

$$E_{ad} = E_{max}\left(\frac{K[E]e}{1+K[E]e}\right)$$

where $[E]=E_{ad}+[E]e$, is the concentration of the protein added; $E_{max}$ is the maximum amount of protein adsorbed on the polyester granules, and K is the adsorption equilibrium constant of the protein.

Example 2

Sequence and Phylogenetic Analyses of Cutinase from *K. radiotolerans*

Figure 1:
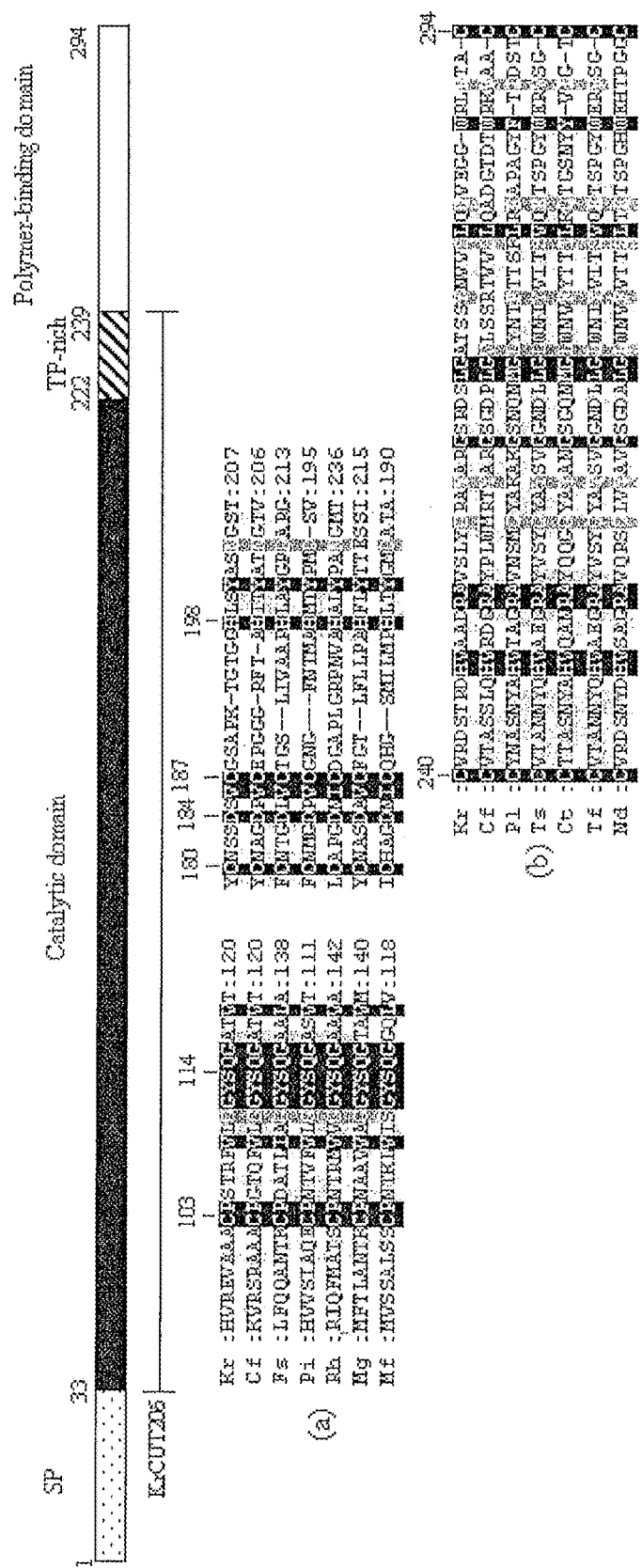
FIG. 1 is a schematic representation of the domain organization of KrCUT and sequence characteristics of some conserved regions. SP, signal peptide; TIP-rich, threonine-praline rich linker; "KrCUT206" (containing 206 amino acids) is a truncated version of KrCUT lacking the polymer-binding domain. "KrCUT189" (containing 189 amino acids) is a truncated version of KrCUT206 further lacking the T/P-rich linker. Inset (a): "cutinase motifs" containing the predicted catalytic triads (S114-D184-H198) and conserved cysteines (C103, C180, C187) according to Wang et al., 2010. The sequences shown in panel (a) are represented in the Sequence Listing as follows.

The 885-bp Krad_4111 locus tag of the *K. radiotolerans* genome (YP_001363838.1; Copeland, 2007) was selected as the result of a BLAST search using the amino acid sequence of FsCUT as a query sequence. A polypeptide having 294 amino acids corresponding to the full length sequence of a cutinase from *K. radiotolerans* was identified. A bioinformatic analysis of the 294-amino acid sequence of full length KrCUT (hereinafter referred to as "ssKrCUT"; SEQ ID NO: 1) revealed a modular domain organization consisting of a 33-amino-acid signal peptide (amino acids 1-33 of SEQ ID NO: 1), a catalytic domain (amino acids 34-222 of SEQ ID NO: 1; SEQ ID NO: 2), and unlike other characterized cutinases, the presence of a C-terminal extension made up of a Pro/Thr-rich linker (amino acids 223-239 of SEQ ID NO: 1; SEQ ID NO: 3), and a designated polymer-binding domain (amino acids 240-294 of SEQ ID NO: 1; SEQ ID NO: 4) (FIG. 1).

Example 3

Cloning of Cutinase-Encoding Gene and Variants

A synthetic gene encoding full-length cutinase from *K. radiotolerans* identified in Example 2 but lacking the 33-amino acid endogenous N-terminal signal sequence was constructed after codon optimization by the reduction of G+C content from 77.2% to 59% for its expression in *E. coli*. The synthetic gene having the nucleotide sequence set forth in SEQ ID NO: 5 was cloned in a recombinant pUC57 plasmid provided by GenScript Corporation (Piscataway, N.J. USA). The specific primers, P1: 5'-GAG CTGCAGGCGACTTGCAGTGACGTC-3' and P2 5'-GCAGAAGCTTTCAAC AAGCAGTTACCAAG-3', were then designed to amplify the mature portion of the KrCUT-encoding gene (amino acids 34-294 of SEQ ID NO: 1; SEQ ID NO: 6; herein referred to as "KrCUT"); P1 and P3: 5'-TGTAAGCTTTCATGTGGTAGGA ACCGGCGT-3' were used to amplify a truncated version KrCUT206 (amino acids 34-222 of SEQ ID NO: 1; SEQ ID NO: 2; herein referred to as "KrCUT189") lacking the C-terminal 72 amino acids, which includes the T/P-rich linker as well as the polymer-binding domain. The indicated primer sets were designed to incorporate a 5' PstI site and 3' HindIII site (underlined) for directional cloning in the IPTG-inducible vector pKK223-3. The PCR parameters were: 94° C. 3 min, 30 cycles of 94° C. for 45 s, Tm-3° C. for 30 s, 68° C. for 1 min, followed by a final extension at 68° C. for 10 min.

To express KrCUT and KrCUT189 in a secreted form, the *E. coli* extracellular carrier protein YebF (Zhang et al., 2006; SEQ ID NO: 8) was used to construct fusion proteins. The gene encoding YebF (366-bp minus stop codon but including the signal peptide; SEQ ID NO: 7) was amplified by oligonucleotides P4: 5'-CGAG GAATTCATGGAGAAAAACATGAAAAAAAG-3' and P5: 5'-GAACTGCAGACGCCGCTGATATTCCGC-3', containing the EcoRI and PstI restriction sites (underlined). The PCR fragment was gel purified and cloned upstream of the cutinase gene in pKK223-2 to produce pKK223-3-YebF-KrCUT and pKK223-3-YebF-KrCUT189. These recombinant plasmids were transformed into *E. coli* JM109 cells by conventional techniques (Sambrook et al., 1989). The cloned genes were verified by DNA sequencing using a Big Dye™ DNA sequencing kit (Applied Biosystems) and an automated DNA sequencer (Model 377, ABI Prism). The nucleotide sequence encoding the YebF-KrCUT fusion protein is set forth in SEQ ID NO: 9 and the corresponding amino acid sequence of YebF-KrCUT is set forth in SEQ ID NO: 10. The nucleotide sequence encoding the YebF-KrCUT189 fusion protein is set forth in SEQ ID NO: 11 and the corresponding amino acid sequence of YebF-KrCUT189 is set forth in SEQ ID NO: 12.

Example 4

Expression and Purification of YebF-KrCUT and YebF-KrCUT189 Fusion Proteins

The YebF-KrCUT and YebF-KrCUT189 fusion proteins were expressed from *E. coli* as described in Example 1, sections 1.2 and 1.3.

Cutinase activity, measured using pNP-butyrate as substrate as described in Example 1, section 1.6, was detected in *E. coli* [pK233-2-YebF-KrCUT and pKK233-2-YebF-KrCUT189] culture 16 h after IPTG induction with the maximum activity found by 20 h (not shown).

Production of the 39-kDa YebF-KrCUT (FIG. 2A, lane 1) fusion protein was confirmed by SDS-PAGE analysis), consistent with the summed masses of the 10-kDa YebF carrier protein and the 29-kDa mature KrCUT. FIG. 2A, lane 1, resulted from one column purification step using the SP-Sepharose™ FF as described in Example 1, section 1.4.

Production of the YebF-KrCUT189 fusion protein was also confirmed by SDS-PAGE analysis.

The YebF-KrCUT fusion protein was further purified as described in Example 1, section 1.4 to electrophoretic homogeneity in two steps involving cation exchange and size exclusion chromatography. Proteins bound on the SP-Sepharose™ eluted in two active peaks: peak 1 (minor) at a lower ionic strength, and peak 2 (major) at higher ionic strength (not shown). The height of peak 1 eluting from the SP-Sepharose™ column increased over time while peak 2 decreased in height, indicating some unknown processing of peak 1 protein species under storage conditions (not shown). This was confirmed by SDS-PAGE analysis of fractions from the major peak 2, which showed two protein bands of $M_r$ 39-kDa and 31-kDa (for YebF-KrCUT). These two species could be separated by an additional SEC step (FIG. 2, lanes 2 and 3). In FIG. 2A, lanes 2 and 3, the two bands from lane 1 were separated by loading the fraction of lane 1 on a HiLoad Superdex™ 75 prep grade (16/60) column.

The YebF-KrCUT189 fusion protein, which also eluted in two active peaks, was purified to electrophoretic homogeneity the same way as for YebF-KrCUT. FIG. 2B, lane 4 represents YebF-KrCUT189 from HiLoad™ Superdex™ 75 prep grade (16/60) column, the fraction was collected after a first column using SP-Sepharose FF.

N-terminal amino acid sequencing performed as described in Example 1, section 1.5 helped to establish the identity of each of the protein bands with respect to YebF-KrCUT and YebF-KrCUT189. The procedure is described with respect to YebF-KrCUT in the following paragraph, but a similar approach was used to establish the identity of each of the protein bands for YebF-KrCUT189.

The sequence ANNETSKSVT derived from the 39 kDa protein band corresponds to the first 10 amino acids of the mature portion of YebF, confirming previous result that the carrier protein is cleaved immediately after the 21-amino acid secretory leader sequence (Zhang et al., 2006). The N-terminal amino acid sequence (AT[A]SDVDVVF) of the 31-kDa species is virtually identical to the first ten amino acids of the mature cutinase. The discrepancy of Ala in the third position versus Cys in the DNA-predicted sequence is due to the fact that Cys without modification is not detectable by Edman degradation.

The above analysis confirmed that when the YebF-KrCUT and YebF-KrCUT189 proteins were purified immediately after fermentation, they exclusively yielded the intact YebF-KrCUT and YebF-KrCUT189 fusion proteins, respectively. Upon storage for several weeks at 4° C., the intact fusion proteins underwent processing to produce a lower molecular weight species corresponding to the cleavage of the YebF portion, resulting in the polypeptides KrCUT and KrCUT189.

The presence of YebF appeared to greatly decrease the activity of the fusion proteins. For example, the processed KrCUT exhibited some three-time higher specific activity compared to that of YebF-KrCUT (162 versus 47 U/mg with pNP-palmitate as substrate). The results are shown in FIG. 6, in which fractions C1-C10 correspond to the first peak (KrCUT) and fractions D9-D11 correspond to the second peak (YebF-KrCUT).

Example 5

Substrate Range

The KrCUT189 protein was purified in a similar way as YebF-KrCUT as described above (FIG. 2B) and its activity towards a number of p-NP esters was compared to those of KrCUT (FIG. 3). With KrCUT, the highest activity was obtained with pNP butyrate showing a 8-fold higher activity over pNP-palmitate which is in accordance with the activity profile of other cutinases (Kim et al., 2003). The KrCUT189 variant generally gave lower activity with various substrates compared to the full length protein. The highest activity of KrCUT189 was towards pNP-myristate, which was surprisingly higher than that of KrCUT. In both cases, there is little activity towards pNB-acetate.

Example 6 pH Optimum and Thermostability

Both KrCUT and KrCUT189 showed a pH optimum of 8 (FIG. 4). Universal Buffer solutions were prepared according to Britton and Robinson (Surinenaite et al., 2002), having the selected pH value from 5-11. Activity of KrCUT and KrCUT189 were measured at the indicated pH, using p-nitrophenyl butyrate as substrate as described in Example 1, section 1.6). Curves were obtained by plotting values of activity against pH.

Enzyme stability was studied over the temperature range of 40-60° C. using purified KrCUT. Aliquots were withdrawn at defined times (10, 30 and 80 min), chilled on ice, and assayed for activity against p-NP butyrate at room temperature. KrCUT appeared thermostable up to 45° C. At 50° C. and above there was virtually no activity left after 10 min of heat treatment (FIG. 5).

Example 7

Potential Inhibitors of Cutinase Activity

KrCUT cutinase activity was assayed as described in Example 1, section 1.6 in the presence of various chemicals using p-NP palmitate as substrate under standard assay conditions. The zinc ion dramatically inhibited cutinase activity with a complete loss of activity at 1 mM and over 90% at 0.1 mM. $Mg^{2+}$ showed only 19% enzyme inhibition at 10 mM; and 50% for $Fe^{2+}$ at 1 mM. $Cu^{2+}$ at 1.0 mM had little effect. The enzyme was not affected by the metal-chelating agent EDTA even at 10 mM. The anionic surfactant SDS was a strong inhibitor of cutinase even at 0.01% retaining only 28% activity. 0.1% SDS resulted in a complete loss of activity. Organic solvents, e.g. alcohols exhibited a strong inhibiting effect on cutinase in concentration above 15-20%. In particular, the 2-propanol used to dissolve the substrate and that is present in the standard assay at 10% (v/v), strongly reduces enzyme activity when it exceeds 15%. Dimethylsulfoxide (at 30%) and dimethylformide (at 5%) inhibited cutinase activity by about 70%. Interestingly, para-chloromercuribenzoate at concentrations 0.01 to 1 mM had no discernible effect on KrCUT implying that there is no free sulfhydryl group among the six cysteines found in KrCUT.

Example 8

Hydrolysis of Cutin

To measure cutinase activity, assays of cutin hydrolysis were performed as described in Example 1, section 1.7 at two different enzyme concentrations. Characteristic cutin components, $C_{16}$ and $C_{18}$ hydroxyl fatty acids, were identified by GC-MS analysis. One representative mass spectrum of the enzymatic reaction is shown in FIG. 7. 18-Hydroxy-octadeca-9,12-dienoic acid, 10,16-dihydroxyhexadecanoic acid and 9,10,18-trihydroxyoctadecanoic acid, with retention times of 55.13, 55.92 and 64.20, respectively, were found to be the major products of hydrolysis (Table 1).

TABLE 1

Momoneric products released from apple cutin by cloned
K. radiotolerans cutinase.

| Retention time | Cutin hydrolysis products | 20 Units Area (%) | 200 Units Area (%) |
|---|---|---|---|
| 55.13 | 18-hydroxy-octadeca-9,12-dienoic acid | 18.0 ± 6.3 | 2.22 ± 0.13 |
| 55.24 | 9,16-dihydroxyhexadecanoic acid | n.d | 3.81 ± 0.62 |
| 55.92 | 10,16-dihydroxyhexadecanoic acid | 39.25 ± 2.5 | 27.74 ± 0.41 |
| 63.37 | 9,10,18-trihydroxyoctadec-10,12-dienoic acid | n.d | 13.25 ± 0.40 |
| 64.20 | 9,10,18-trihydroxyoctadecanoic acid | n.d | 25.55 ± 0.10 |
| 66.19 | 9,10,18-trihydroxyoctadec-9 enoic acid | n.d | 6.25 ± 0.40 |

Hydrolysis was carried out at two different units of activity of cutinase.
Not detected (n.d)

Additional components of C16 and C18 fatty acids were identified as 9,16-dihydroxyhexadecanoic acid (55.24 min), 9,10,18-trihydroxyoctadec-10,12-dienoic acid (63.37 min), and 9,10,18-trihydroxyoctadec-9 enoic acid (66.19 min).

Example 9

Degradation of Synthetic Polyesters by KrCUT and KrCut189

An initial plate clearing assay indicated that a lawn of E. coli JM109 cells harboring YebF-KrCUT was capable of producing a large clearing zone with PCL as substrate (not shown). To quantify this further, pellets of polycaprolactone (PCL) as well as films of PCL were incubated with KrCUT at various enzyme concentrations (1.25 µM, 2.5 µM, and 5 µM representing 4.7, 9.5 and 19 enzyme Units) at 37° C. The degradation of the polymer was followed over time by analyzing aliquots of the reaction mixture by HPLC for the detection of the released monomer (6-hydroxyhexanoic acid) and characterization of the remaining polymer by SEC after lypholization of the sample. KrCUT was able to release nearly 90% of the acidic monomers with enzyme concentration of either 2.5 or 5 µM in 6 hours. Even with a very low concentration of the enzyme (1.25 µM) thin films of PCL were nearly completely degraded after 24 hours (FIG. 8A).

SEC analysis confirmed the results obtained by HPLC. Comparison of the peak area corresponding to that of the polymer showed a gradual decrease over time with complete disappearance of the polymer in experiments conducted with 2.5-5 µM after 24 hours. This correlated well with the increase in acid detected (Table 2).

TABLE 2

Evidence of PCL degradation: comparison of SEC and HPLC analysis

| time (h) | PCL (SEC) | $M_n$ (Daltons) | $M_w$ (Daltons) | acid (HPLC) |
|---|---|---|---|---|
| 0 | 100% | 44000 | 63300 | 0% |
| 1 | 61% | 53800 | 64400 | 28% |
| 3 | 27% | 55000 | 66600 | 60% |
| 6 | 12% | 58200 | 68100 | 85% |
| 24 | 0.3% | 69500 | 74000 | 100% |

A dramatic increase in $M_n$ and $M_w$ from 44000 and 63300 to 69500 and 74000 emphasized the preference of KrCUT for low molecular polymers. The degradation of PCL pellets proceeded more slowly with 18% of the maximum yield of 6-hydroxy hexanoic acid were detected in the reaction mixture after incubation with 2.5 µM of protein for 24 hours (FIG. 8A). The decrease in depolymerization is presumably due to the limited surface area of the PCL pellets compared to the films. Nearly identical results were obtained when PCL pellets and PCL films were incubated with KrCUT189 (2.5 µM) (FIG. 8A).

Both KrCUT and KrCUT189 (2.5 µM; 2 Units) only degraded approximately 5% of PLA (FIG. 8B). However, in the case of poly(1,3-propylene adipate), a polymer consisting of alternating diacid and diol subunits, 12% and 17% of adipic acid were found in the reaction mixture containing KrCUT and KrCUT189, respectively, after 24 hours (FIG. 8B). All in all, it appears that both enzymes exhibited a preference for longer chain monomers such as 6-hydroxy hexanoic acid and adipic acid (both $C_6$ unit in polymer) compared to lactic acid ($C_2$ unit).

Example 10

Polymer-Binding Domain of KrCUT

Different polymers (cellulose, PLA, PCL, and PHB) were tested to evaluate the ability of KrCUT and KrCUT189 to bind these materials. Binding assays for PCL and PLA could not be performed since both polymers were degraded by the enzymes. KrCUT did not bind to cellulose, indicating that the binding domain of the cutinase is distinct from a cellulose binding domain (CBD). On the other hand, KrCUT binds efficiently to PHB but did not degrade. The KrCUT189 variant showed no binding to PHB, indicating that essentiality of the C-terminal extension for this activity.

The kinetics of KrCUT adsorption to PHB is shown in FIG. 9. The curve shows the relation between the adsorbed cutinase and the equilibrium concentration of the enzyme, with the adsorption to the PHB surface expressed by the Langmuir adsorption equation. As a result, the maximum amount of cutinase absorbed on the PHB granules (Emax) was determined to be 23.68±0.03 µg/mg, and the adsorption equilibrium constant (K) was calculated to be 0.12±0.03 ml/mg PHB.

Example 11

Effect of KrCUT on Hemp Fibre

The quantity of pectin released from natural hemp fibre by KrCUT in conjunction with the action of a thermostable pectate lyase was assessed as described in Example 1, section 1.13. The thermostable pectate lyase alone released a certain amount of pectin as expected of the pectinolytic activity (Xiao et al., 2008). With an increasing amount of added cutinase, a higher percentage of pectin degradation products were detected when the quantity of added pectate lyase was fixed. When KrCUT was incubated with hemp fibre at the highest concentration in the absence of pectate lyase, negligible amounts of pectin from the fibre material were detected as compared to a control reaction without any added enzyme (FIG. 10).

The effect of KrCUT on the hemp fibre integrity was visualized using light microscopy and SEM. Light microscopic images revealed that treatment of fibres by both cutinase and pectate lyase appeared to produce more separated fibre bundles, whereas pectate lyase alone showed more fibres embedded in pectin and wax material (FIG. 11). The SEM pictures showed that cutinase treatment gave more separated fibres having a cleaner surface, compared to those of pectate lyase treated samples.

Example 12

Effect of KrCUT on Inactivation of Mycotoxin

Fungi strains *Aspergillus flavus* and *Aspergillus niger* were cultivated and used for Aflatoxin and Ochratoxin isolation, respectively.

Reactions were performed in 2 mL volumes in Eppendorf tubes comprising the mycotoxin to be analyzed and 0.3 mg/mL KrCUT enzyme. Ochratoxin A was added at a concentration of 200 ppb. The samples for Aflatoxin contain the B1 and B2 types of the mycotoxin in the concentration of 600 ppb and 9 ppb, respectively. In control reactions, the enzyme volume was replaced by an equivalent amount of water. The reactions were incubated at 37° C., samples were withdrawn at time periods 0, 1 h, 2 h, followed by the addition of equal volume of methanol 80% (v/v) for extraction. Reactions were stored, if needed until chromatographic analysis.

Analysis: samples were centrifugated and the supernatant analyzed for Ochratoxin A and Aflatoxin by LC-MS/MS as described by Rudrabhatla et al., 2007. Results are shown in Tables 3 and 4.

TABLE 3

Effect of KrCUT on Ochratoxin

| Incubation time (h) | Residual Ochratoxin % |
|---|---|
| 0 | 100 |
| 1 | 56.63 |
| 2 | 0.68 |

TABLE 4

Effect of KrCUT on Aflatoxin mixture

| Incubation time (h) | Residual Aflatoxin B1 (%) | Residual Aflatoxin B2 (%) |
|---|---|---|
| 0 | 100 | 100 |
| 3 | 48 | 48 |

The results in Tables 3 and 4 show that the KrCUT is able to act on both aflatoxin and ochratoxin, in contrast to most other cutinases that can act only on one type of mycotoxin.

Example 13

Effect of KrCUT on Inactivation of Mycotoxin

Fungi strains *Aspergillus flavus* and *Aspergillus niger* were cultivated and used for Aflatoxin and Ochratoxin isolation, respectively.

Reactions were performed in 2 mL volumes in Eppendorf tubes comprising the mycotoxin to be analyzed and 0.3 mg/mL enzyme. The samples for Aflatoxin contain the B1 type of the mycotoxin in the concentration of 1000 ppb. In control reactions, the enzyme volume was replaced by an equivalent amount of water. The reactions were incubated at 37° C., samples were withdrawn at time periods 0, 1 h, 2 h, 4 h and 24 h followed by the addition of equal volume of methanol 80% (v/v) for extraction. Reactions were stored, if needed until chromatographic analysis.

Analysis: samples were centrifugated and the supernatant analysed for Ochratoxin A and Aflatoxin by LC-MS/MS as described by Rudrabhatla et al., 2007. Results are shown in Table 5.

TABLE 5

Effect of KrCUT on Aflatoxin

| Incubation time (h) | Residual Aflatoxin B1 (%) |
|---|---|
| 0 | 100 |
| 1 | 80 |
| 2 | 61.5 |
| 4 | 49 |
| 24 | 20 |

The results in Table 5 show that KrCUT is able to reduce amount of 1000 ppb Aflatoxin B1 to 200 ppb within 24 h.

Example 14

Construction of Recombinant Fusion Polypeptides Having a Cutinase Catalytic Domain Operably Linked to a Polymer-Binding Domain Recombinant fusion polypeptides having a cutinase catalytic domain operably linked to a polymer-binding domain may be constructed using basic recombinant DNA cloning techniques, making use of suitable domains (cutinase catalytic domains, linker domains, and polymer binding-domains) from different cutinases. Examples of different cutinases and the domains therein are shown in Table 6.

TABLE 6

Examples of different cutinases and the domains therein

| Gene/ protein name/ organism | Cutinase amino acid sequence (signal sequences are in lower case letters; cutinase catalytic domains are in bold; linkers are italicized; polymer binding domains are underlined) | SEQ ID NO: |
|---|---|---|
| >GI:502883354 WP_013118330 cutinase [Cellulomonas | mqvtptrrtlagyvaavaalasvttlatgasaAPACPDVEL VFARGTGEAAGLGIVGRPLERALAAELPGRTVVATAVDYAA SSSQASAGPGSGDMVAKVRSRAAACPGTQFVLGGYSQGATV TDLALGIRTGVTAGTALPEDLAARVAAVVVYGNPLGLTRRT | 13 |

TABLE 6-continued

Examples of different cutinases and the domains therein

| Gene/ protein name/ organism | Cutinase amino acid sequence (signal sequences are in lower case letters; cutinase catalytic domains are in bold; linkers are *italicized*; polymer binding domains are <u>underlined</u>) | SEQ ID NO: |
|---|---|---|
| *flavigena*] | IAQAAPAFATRTVEYCNAGDPVCEPGGGRFTAHITYATNGT VLEGARFAAARVTA*PAPTPTPGPTGTPAPVPSAEPTPAPGD* <u>TCVTASSLQHVRDGRAYPLWMRTYARGSGDPLGVLSSRTVV SLQADGTDTWRKVAAC</u> | |
| >gi\|697974256\| gb\|KGM14009.1\| cutinase [*Cellulomonas bogoriensis* 69B4 = DSM 16987] | msitpggrkvaaalittaaltstaaiatpataaapvagpva tsTGDCPDVHVVFARGTGEPRGLGIVGRPFVSDLGDALPTM TVTSYAVNYSANASQTSAGPGAGDMTSHVTSMAARCPGTQF VLGGYSQGATVTSIAVGARSTSIRSRVLPANLEPRVAAVVV FGNPLGLTRRTIASEAPAYAAKSRDYCNRSDTVCGGRGDAR GGHLAYVSNGSVADGAAFAA*SLVGVAPGDPAS*<u>CVTARAVDH VEADRAFRSVLRAYARGSRDPLGRLTSSDLVSLQRTGQDSW SVVPAC</u> | 14 |
| cutinase [*Cellulomonas bogoriensis* 69B4 = DSM 16987]; accession KGM14008.1 | mstspvrrtltaallaaglaatsvalspaasatslpaaapl sAGSCPDVQVVFARGTGERAGLGIIGRPFARALADELPGMT VTSHAVDYAAAASQRSAGPGATAMTDHVTAMAARCPGTQFV LGGYSQGATVTSIALGIRAGTTTGRAIPDELSDRVAAVVVF GNPLGMRGQTIASASRTYADRAKDYCNSGDSICGRQPSTGR GTHTGYATNGSTTDGARFAAGLVTA*NPPEAAPPTAPPTTPP TTPAPP*<u>SDQVTCVTAQVSEHVEARRAIRGLTRAYARGTLED IGRLRSTEEVSLRRSGTFSWTPTASC</u> | 25 |
| >gi\|697886498\| gb\|KGM03336.1\| hypothetical protein Q760_05675 [*Cellulomonas cellasea* DSM 20118] | mhqltppaapsrpraarrprrllaaalalaatsgalstlaa ptavaAPACADVEVLFARGTGEAPGLGVLGTPFVRSVTSAL SDRTVTSYAVNYAAESSQRSAGPGATDLTNHLTATAAACPG TRFVLGGYSQGATVVDLALGIRTGTTTGTAIPAALEPRVAA IVVFGNPLGISGRTIATASPTYAARARDFCATGDPVCGGGS SFAAHLAYRTNGDVTAGADFAA*GLARATTVPVPTPTVPGTP TPSPTAPGTPTPVPTTSPTPAPSPTAPGAA*<u>CVRASTRAHVE AGRAERRHGIAYATGSGDRIGWVSSFVRVSVQQTADGWERV LSC</u> | 15 |
| >gi\|521090090\|ref\| WP_020420995.1\| cutinase [*Amycolatopsis* sp. ATCC 39116] | mvhnrlrkltllacavvglagtatvgtasgatsaaACSDLE IVFARGSGEAPGLGITGTPLVSDVKSALSSASVSSYAVDYA ASYDQTSAGPGATDMSNHIKSTAAACPDTKFAIGGYSQGAS VTDIAIGIRTYLGTGQTIPTELAPRVVAVIAFGNPLGLYGQ TIKTASPTYGPKSLEFCNRGDNVCGGTGTGPGYGHLSYARD GSVDQAAAFIAKQYNAS | 16 |
| >gi\|648619273:1- 219 cutinase [*Frankia* sp. BMG5.12] | mrlarswkqravavfltavagtlgagitaspvsAATCSDVD VVFARGSGELPGLGITGTPFVNSVKQGLTGKTVSSYAVNYA ADIAQTSDGAGATDMTRHVRSVAASCPNTKFVLGGYSQGAS VTDISIGIRTFLGSGETIPTELAPRVAAVVVFGNPLALFGQ KITTASPLYGPKAKEFCNLGDPVCAGGFNVFAHLTYGFDGS TANGASFAVSKVRA | 17 |
| >gi\|383779171\|ref\| YP_005463737.1\| putative cutinase [*Actinoplanes missouriensis* 431] | mnkrrkrnvatvgicaavvaagavitpqafagtlfggratt aAGDCSDVELVFARGTGEPQGLGIVGRPLARELAAALPDLA VGSFAVVYAAAGNQRSAGPGATNMSRHITEVAGECPDTRFV IGGYSQGASVTDIAIGIRGAGTAGEAIPERLADRVAAVVVF GNPLGLQRRTIAGSSAVFGPKAKEFCNTGDPVCGGGGNFAA HLAYPRNGSVQQAAAFAASKIAG | 18 |
| >gi\|589395439\| gb\|EXG80196.1\| Cutinase [*Cryptosporangium arvum* DSM 44712] | msylltvrrvvtavaltatgltgiafaaspaTAACSDVQVV FARGSTEAPGLGILGRPLVSAVQQQLPGLTVDSYAVDYAAN VSQTSAGPGATDMSDHITEVAARCPDTEFVIGGYSQGASVT DIAIGIRTTLGRGGTIPENLAPRIKAVTVFGNPLRLSRQTI NSASQLYGRKAIDICATGDPVCGNGANAAAHLRYAFDGSVT RAAQFAANLVRTT | 19 |
| >gi\|653334177\|ref\| WP_027494901.1\| MULTISPECIES: cutinase [*Rhodococcus*] | mkrrliaysiaalaisatavalptgvasAAPCSDVDVSFAR GTGELPGLGITGTPFVNSVKSQLSDRSVSTYAVNYAADFTQ ASAGPGSRDLVAHLNSVAASCPSTKFVIGGYSQGATVVTNA VGLRTPSSFTGAVIPAAIADRIEAVVVFGNPFGLTGRKIET ASSTYGSRTNSFCNFGDPVCQIGGFNTFAHLTYGTNGSTTQ GASFAAAQVRS | 20 |

Further examples of constructions of fusion proteins are shown below.

14.1 Fusion Protein CfKr

Amino acid sequences of this construct contain the catalytic domain of cutinase from *Cellulomonas flavigena* (CfCUT) fused to the C-terminal region (T/P-rich linker and polymer binding domain) from *Kinecoccus radiotolerans* cutinase. The amino acid sequence of this fusion protein is set forth in SEQ ID NO: 21, in which residues 1-187 correspond to the cutinase catalytic domain from CfCUT, residues 188-206 correspond to the T/P-rich linker of KrCUT, and residues 207-262 correspond to the polymer binding domain of KrCUT. To ensure extracellular secretion of this fusion protein, the N-terminus thereof can be fused to the C-terminus of YebF (SEQ ID NO: 8) to give YebF-CfKr encoded by the nucleotide sequence of SEQ ID NO: 22.

14.2 Fusion Protein KrCf

Amino acid sequences of this construct contain the cutinase catalytic domain of KrCUT (SEQ ID NO: 2) fused to the T/P-rich linker of KrCUT (SEQ ID NO: 3), which in turn is fused to polymer binding domain of CfCUT. The amino acid sequence of this fusion protein is set forth in SEQ ID NO: 23, in which residues 1-189 correspond to the cutinase catalytic domain from KrCUT, residues 190-206 correspond to the T/P-rich linker of KrCUT, and residues 207-262 correspond to the polymer binding domain of CfCUT. To ensure extracellular secretion of this fusion protein, the N-terminus thereof can be fused to the C-terminus of YebF (SEQ ID NO: 8) to give YebF-KrCf encoded by the nucleotide sequence of SEQ ID NO: 24.

Example 15

Long Term Stability of KrCUT in Culture Medium

Stability over time and/or with temperature represents one of the main desirable properties of an enzyme, for their utilization as ingredients in cleaning product formulation. Most enzymes tend to lose activity with the time.

The KrCUT was routinely produced in the form of secreted fusion protein, YebF-KrCUT in culture medium. Culture medium having KrCUT activity was stored at 4° C. without any additives. Activity was determined periodically by using p-nitrophenyl laurate as substrate, and reported in Table 7.

TABLE 7

Storage stability of KrCUT in culture medium at 4° C.

| | Months | | | | |
|---|---|---|---|---|---|
| | 0 | 3 | 4 | 17 | 19 |
| Activity (U/mL) | 3.0 ± 0.94 | 25.67 ± 0.94 | 17.13 ± 0.70 | 16.66 ± 2.47 | 21.94 ± 1.83 |

At room temperature, KrCUT in culture medium without additives retains full activity for a period of 4 months.

Example 16

Stability of KrCUT in Stabilisation Buffer

For stability testing, culture medium showing KrCUT activity, and containing 100 mg total protein was used. Stabilisation buffer composed of sodium gluconate 1-5%, sodium carbonate 1-5%, sodium citrate 1-5% and propylene glycol 1-5% was prepared; 50 mL enzyme solution was added to 200 mL of buffer and stored at room temperature, after mixing. Samples were taken at defined time periods and the enzymatic activity was measured using p-nitrophenyl dodecanoate as substrate.

Activity loss could be observed only after 4 months, and up to 65% of the initial activity was present after 9 months at room temperature.

Data are reported in FIG. 12.

For most of enzymes, more complex mixtures with different ingredients at higher concentrations are used for stabilisation, namely polyol such as propylene glycol and glycerol, boric acid and boron derivatives and sodium formate.

In some test cleaning product formulations, the KrCUT enzyme was combined with a mix of proteases from *Bacillus*. The efficacy of the cleaning product was reduced, demonstrating the contribution of the KrCUT to the overall efficacy of the cleaning product. However, the loss of KrCUT activity could be avoided or substantially reduced by the additional of stabilizers to the formulation (e.g., polyols and/or boric acid).

Example 17

Stability of KrCUT in the Presence of Metal Ions

Enzymes such as lipases, amylases, and proteases are widely used in cleaning product formulations, and these types of enzymes are generally sensitive to the presence or absence of metal ions. For example, lipases generally require calcium for optimal activity. Amylases and proteases also generally require metal ions for optimal activity.

For improved performance, chelating agents (namely EDTA) are often added to cleaning products. These chelating agents sequester metal ions and thus may negatively impact enzyme activity (e.g, of lipases, amylases, and proteases).

Interestingly, activity of KrCUT is not affected by EDTA or other chelating agents often found in cleaning products. More specifically, 10% w/v of EDTA does not inhibit KrCUT activity (data not shown), and the enzyme retains 100% activity in the presence of GLDA (L-Glutamic acid N,N-Diacetic acid Tetra sodium), at a concentration of 5% w/v.

More particularly, stability in the presence of hydrogen peroxide makes KrCUT an interesting candidate for cleaning products with disinfection properties.

Example 18

Construction and Expression of Recombinant Enzymes Having Cutinase Activity

The recombinant enzymes listed in Table 8 were constructed, expressed and purified for further characterization as generally described in Examples 3 and 4.

TABLE 8

Recombinant enzymes having cutinase activity

| Enzyme | Organism(s) | Amino acid sequence (YebF carrier proteins are in lower case letters; cutinase catalytic domains are in bold; linkers are *italicized*; polymer-binding domains are underlined) | SEQ ID NO: (without YebF) |
|---|---|---|---|
| YebF-KrCUT | *Kineococcus radiotolerans* | meknmkkrgaflglllvsacasvfaannetsks vtfpkcedldaagiaasvkrdyqqnrvarwadd qkivgqadpvawvslqdiqgkddkwsvpltvrg ksadihyqvsvdckagmaeyqrrATCSDVDVVF ARGTGETPGLGVVGGPFVRSLTGELSDRTVTSH AVDYAASSSQASAGPGATAMSAHVREVAAACPS TRFVLGGYSQGATVTDIALGIRTGTTTGTPVPA ELAGRVAAVVVFGNPLGLSGRTIATASSTYGPK SKDYCNSSDSVCGSAPKTGTGGHLSYASNGSTT DGARFAAGLVRAAG*TPTTPTPTPTPTPVPTT*<u>CV RDSTRDHVAADRAVSLYGRAYARGSRDSLGATS SYNVVSLQQVEGGWRLVTAC</u> | 6 |
| YebF-AmCUT | *Amycolatopsis* sp. ATCC 39116 | meknmkkrgaflgillvsacasvfaannetsks vtfpkcedldaagiaasvkrdyqqnrvarwadd qkivgqadpvawvslqdiqgkddkwsvpltvrg ksadihyqvsvdckagmaeyqrrACSDLEIVFA RGSGEAPGLGITGTPLVSDVKSALSSASVSSYA VDYAASYDQTSAGPGATDMSNHIKSTAAACPDT KFAIGGYSQGASVTDIAIGIRTYLGTGQTIPTE LAPRVVAVIAFGNPLGLYGQTIKTASPTYGPKS LEFCNRGDNVCGGTGTGPGYGHLSYARDGSVDQ AAAFIAKQYNAS | 26 |
| YebF-Am-Kr | *Amycolatopsis* sp. ATCC 39116; *Kineococcus radiotolerans* | meknmkkrgaflglllvsacasvfaannetsks vtfpkcedldaagiaasvkrdyqqnrvarwadd qkivgqadpvawvslqdiqgkddkwsvpltvrg ksadihyqvsvdckagmaeyqrrACSDLEIVFA RGSGEAPGLGITGTPLVSDVKSALSSASVSSYA VDYAASYDQTSAGPGATDMSNHIKSTAAACPDT KFAIGGYSQGASVTDIAIGIRTYLGTGQTIPTE LAPRVVAVIAFGNPLGLYGQTIKTASPTYGPKS LEFCNRGDNVCGGTGTGPGYGHLSYARDGSVDQ AAAFIAKQYNAS*AGTPTTPTPTPTPTPVPTT*<u>CV RDSTRDHVAADRAVSLYGRAYARGSRDSLGATS SYNVVSLQQVEGGWRLVTAC</u> | 27 |
| YebF-CfCUT | *Cellulomonas flavigena* | meknmkkrgaflglllvsacasvfaannetsks vtfpkcedldaagiaasvkrdyqqnrvarwadd qkivgqadpvawvslqdiqgkddkwsvpltvrg ksadihyqvsvdckagmaeyqrrAPACPDVELV FARGTGEAAGLGIVGRPLERALAAELPGRTVVA TAVDYAASSSQASAGPGSGDMVAKVRSRAAACP GTQFVLGGYSQGATVTDLALGIRTGVTAGTALP EDLAARVAAVVVYGNPLGLTRRTIAQAAPAFAT RTVEYCNAGDPVCEPGGGRFTAHITYATNGTVL EGARFAAARVTA*PAPTPTPGPTGTPAPVPSAEP TPAPGDT*<u>CVTASSLQHVRDGRAYPLWMRTYARG SGDPLGVLSSRTVVSLQADGTDTWRKVAAC</u> | 28 |
| YebF-Cf-TP | *Cellulomonas flavigena*; *Kineococcus radiotolerans* | meknmkkrgaflglllvsacasvfaannetsks vtfpkcedldaagiaasvkrdyqqnrvarwadd qkivgqadpvawvslqdiqgkddkwsvpltvrg ksadihyqvsvdckagmaeyqrrAPACPDVELV FARGTGEAAGLGIVGRPLERALAAELPGRTVVA TAVDYAASSSQASAGPGSGDMVAKVRSRAAACP GTQFVLGGYSQGATVTDLALGIRTGVTAGTALP EDLAARVAAVVVYGNPLGLTRRTIAQAAPAFAT RTVEYCNAGDPVCEPGGGRFTAHITYATNGTVL EGARFAAARVTA*AGTPTTPTPTPTPVPTT*<u>CV TASSLQHVRDGRAYPLWMRTYARGSGDPLGVLS SRTVVSLQADGTDTWRKVAAC</u> | 29 |

The constructed and expressed enzymes include the predicted mature wild-type cutinases from *Kineococcus radiotolerans* ("KrCUT"), *Amycolatopsis* sp. ATCC 39116 ("AmCUT", which lacks a linker domain and a polymer binding domain), and *Cellulomonas flavigena* ("CfCUT"), as well as the chimeric variants "YebF—Am—Kr" (having AmCUT fused to the T/P-rich linker domain and the polymer binding domain of KrCUT), and "YebF-Cf-TP" (having the cutinase catalytic domain of CfCUT, the T/P-rich linker domain of KrCUT, and the polymer binding domain of CfCUT). The domain structures of each of the recombinant enzymes listed in Table 8 are summarized in Table 9 (following autolytic cleavage of the respective YebF carrier proteins).

TABLE 9

Summary of domain structure of recombinant enzymes having cutinase activity

| Enzyme name | Cutinase catalytic domain from: | Linker domain from: | Polymer binding domain from: |
|---|---|---|---|
| KrCUT | Kineococcus radiotolerans | Kineococcus radiotolerans | Kineococcus radiotolerans |
| AmCUT | Amycolatopsis sp. ATCC 39116 | n/a | n/a |
| Am-Kr | Amycolatopsis sp. ATCC 39116 | Kineococcus radiotolerans | Kineococcus radiotolerans |
| Cf | Cellulomonas flavigena | Cellulomonas flavigena | Cellulomonas flavigena |
| Cf-TP | Cellulomonas flavigena | Kineococcus radiotolerans | Cellulomonas flavigena |

Constructions

To ensure expression of the recombinant enzymes, synthetic genes encoding fusion proteins consisting of the carrier protein YebF (357 bp) and the corresponding full-length cutinases lacking the native N-terminal signal sequences were constructed.

The optimized sequences for reduction of G+C content were provided by Biomatik USA. The nucleotide sequences were cloned into the NcoI and HindIII sites of the pTrc2Bd vector, a derivative of the plasmid pTrcHis2B, obtained by deletion of the His Tag. The recombinant plasmids were transformed in the β-galactosidase-positive and lactose inducible E. coli MG1655 strain.

The synthetic gene of Amycolatopsis sp. ATCC 39116, cutinase (AmCUT) corresponds to 564 bp, after optimization the G+C content was reduced from 71% to 55%.

The recombinant enzyme variant Am—Kr was constructed as a 786 bp polynucleotide consisting of 561 bp AmCUT and 225 bp of the C-terminal portion of KrCUT. Codon optimization led to G+C content reduction from 68% to 56%.

The synthetic gene encoding CfCUT corresponded to an 812 bp nucleotide sequence, in which G+C content was reduced from 78% to 59% after codon optimization.

The polynucleotide encoding the variant CfTP represented a DNA fragment of 789 bp.

Production at Small Scale

Expression of the recombinant enzymes were performed by growing the E. coli MG1655 harboring the recombinant plasmids pTrc3Bd. Colonies of the cells on LB agar plates were selected and used to prepare pre-cultures consisting of 5 mL TB media supplemented with ampicillin (50 μg/mL). The culture was incubated at 37° C., on a rotary shaker at 200 rpm, for 16 h. The overnight culture was used to inoculate 1 L of fresh TB media. Recombinant enzyme production was induced by addition of 10 g/L lactose, at optical density (OD) 0.5, cells were allow to grow for 24 h, collected by centrifugation at 4000 rpm, 20 min (Eppendorf Centrifuge 5810R). The supernatant represents the source of cutinase for activity measurements.

Production of Cutinase Variants in Bioreactor

Fermentation was performed in a 30-Liter computer-controlled, in-situ sterilizable bioreactor (INFOR HT Techfors), with a working volume of 20 L. The bioreactor was filled with 18 L of TB culture medium and sterilized at 121° C. for 20 min. A regulation system was used to control the temperature at 30° C. throughout the experiment. A pH of 7.0 was maintained constant by using acidic $H_2SO_4$ and basic NaOH regulation.

The stirring speed was first set at 400 rpm and then linked to dissolved oxygen (DO) concentration at 25% saturation. The airflow velocity was set to 1 wm. The bioreactor was inoculated with 5% volume of culture under aseptic conditions, using pre-culture. First pre-culture was performed in 5 mL TB media, supplemented by ampicillin (50 μg/mL), and incubated at 37° C., 16 h, using bacteria colonies from LB agar plate. This culture was used to inoculate the second pre-culture, in a 1 L flask, TB medium, incubation under the same conditions.

Expression of recombinant enzymes was initiated at OD600 of 7, by adding lactose at a concentration of 10 g/L. The cultivation was allowed to continue for 24 h, after induction, fermentation liquid was collected by centrifugation, 8000 rpm for 30 min (Beckman centrifuge, Model Avanti J26 XPI).

The following crude culture supernatants were obtained:
KrCUT (~8 L); 1.6 U/mL (pNP-dodecanoate);
AmCUT (~8 L); 1.2 U/mL (pNP-dodecanoate);
Am—Kr (~16 L); 0.5 U/mL (pNP-dodecanoate);
CfCUT (~16 L); 0.5 U/mL (pNP-dodecanoate); and
Cf-TP (~8 L); 0.6 U/mL (pNP-dodecanoate).

Purification

In a first step, all 5 enzymes were concentrated to about 0.5 L using a 10 kD cut-off holo fiber membrane. During this step, the enzyme containing solutions became much darker, probably due to medium ingredients that remained loosely bound to proteins contained in the solution and thus did not pass the 10 kD barrier.

After concentration, each enzyme solution was subjected to dynamic dialysis on a SPECTRA/POR™ 500-016 HP-75 dialysis module, 10 kD, 6500 cm². In this step, the individual protein concentration was kept constant, but salt and medium components were removed gradually. The enzyme-containing solution was dialyzed against 20 mM sodium phosphate, pH 6.0 until the conductivity of the solution was lower than 2 mS/cm².

Theoretical isoelectric points and the molecular masses of the enzymes were calculated using their putative amino acid sequences. The results and properties of each of the enzyme variants are shown in Table 10.

TABLE 10

Properties of recombinant enzymes expressed

| Enzyme | Length (aa) | Calc. MW (kD) | 1 microgram = (pmol) | Molar extinction coefficient | 1 Absorbance Unit [280 nm] corr. to (mg/mL) | Absorbance [280 nm] of 1 mg/mL | Isoelectric point | Predicted charge at pH 7 |
|---|---|---|---|---|---|---|---|---|
| YebF-KrCUT | 393 | 39.5 | 25.31 | 37920 | 1.04 | 0.96 | 8.81 | 6.13 |
| KrCUT | 261 | 26.1 | 38.37 | 16650 | 1.57 | 0.64 | 8.59 | 3.07 |

TABLE 10-continued

Properties of recombinant enzymes expressed

| Enzyme | Length (aa) | Calc. MW (kD) | 1 microgram = (pmol) | Molar extinction coefficient | 1 Absorbance Unit [280 nm] corr. to (mg/mL) | Absorbance [280 nm] of 1 mg/mL | Isoelectric point | Predicted charge at pH 7 |
|---|---|---|---|---|---|---|---|---|
| YebF-AmCUT | 309 | 32.3 | 30.98 | 34550 | 0.93 | 1.07 | 6.98 | −0.03 |
| AmCUT | 187 | 18.8 | 53.11 | 13280 | 1.42 | 0.71 | 5.20 | −3.10 |
| YebF-Am-Kr | 383 | 40 | 25.0 | 44320 | 0.90 | 1.11 | 8.04 | 2.04 |
| Am-Kr | 261 | 26.6 | 37.65 | 23050 | 1.15 | 0.87 | 6.32 | −1.03 |
| YebF-CfCUT | 393 | 40.6 | 24.60 | 42320 | 0.96 | 1.04 | 8.69 | 4.97 |
| CfCUT | 271 | 27.2 | 36.77 | 21060 | 1.29 | 0.77 | 8.29 | 1.90 |
| YebF-Cf-TP | 384 | 39.9 | 25.06 | 42330 | 0.94 | 1.06 | 8.94 | 6.97 |
| Cf-TP | 262 | 26.5 | 37.80 | 21060 | 1.26 | 0.80 | 8.84 | 3.90 |

Based on their calculated molecular weights, their isoelectric points, and other properties, the enzymes YebF-KrCUT and KrCUT, YebF-CfCUT and CfCUT, as well as YebF-Cf-TP and Cf-TP, were all predicted to bind to a cation exchanger (Capto™-S at a pH of 6.0 and a conductivity below 2 mS/cm$^2$). The enzyme YebF-AmCUT was predicted to weakly bind to the cation exchanger, but not the enzyme AmCUT. The enzyme Yeb-F—Am—Kr was predicted to bind to the cation exchanger, whereas the enzyme Am—Kr was considered to bind minimally.

Despite the generally positive binding assessment of the above enzymes (with exception of AmCUT) to a cation exchanger (Capto™-S and SP-Sepharose™ XL were tested) under the selected conditions (pH 6.0, 2 mS/cm$^2$), only KrCUT bound completely to the resin. CfCUT did not bind at all and appeared completely in the flow through, whereas active enzyme for AmCUT, Am—Kr, and Cf-TP were found in both the column flow through and in bound fractions.

Bound fractions of each enzyme (with the exclusion of CfCUT) were concentrated using stirring cell with a cut-off membrane of 10 kD, and subjected to size exclusion chromatography using a Hi-Load™ Superdex™ pg 16/60 column, which also allowed the assessment of the native molecular mass of the enzymes based on their retention time.

For KrCUT separated on SP-Sepharose™ XL, two active fractions (A7/A8, and A11-B1; chromatogram on shown) were collected. Both fractions showed similar activity but, due to the higher yield, fraction A11-B1 was selected for further studies and purified by size exclusion chromatography.

For AmCUT separated on Capto™-S, only a very small amount of active enzyme bound to the column and was subsequently concentrated and subjected to size exclusion chromatography (chromatogram not shown). In parallel, the flow through containing most of the active Am enzyme was collected, concentrated, dialysed against 20 mM Na-phosphate, pH 7.0, and applied to a DEAE-Sepharose™ FF 16/10. Under the chosen conditions, active enzyme did not bind to the column and appeared in the flow through that was collected, concentrated and subjected to size exclusion chromatography. Even though AmCUT did not bind to DEAE-Sepharose™, most of the contaminating proteins did and thus this step resulted in an almost pure enzyme. Active almost pure AmCUT was thus only found in fraction X1 (flow through). All bound factions did not contain enzyme activity.

For Am—Kr separated on Capto™-S, in contrast to AmCUT, Am—Kr did bind to the cation exchanger in much larger quantity, although active enzyme was also found in the flow through. Fractions B3-B9 were active and were pooled (chromatograph not shown), concentrated and subjected to size exclusion chromatography as final purification step.

For CfCUT separated on Capto™-S, CfCUT did not bind to the cation exchanger at all. Thus, a similar purification approach was chosen as for AmCUT cutinase. The active flow-through of CfCUT was collected, concentrated and diafiltrated against 20 mM sodium phosphate pH 7.0, and the enzyme was loaded to a DEAE-Sepharose™ FF column (16/10). The flow through contained the active enzyme and was collected, concentrated and subjected to size exclusion chromatography on Superdex™ 75 μg. Active CfCUT was exclusively found in fraction X1 (chromatograph not shown). None of the bound fractions contained active enzyme.

For Cf-TP separated on Capto™-S, in contrast to CfCUT, parts of Cf-TP did bind to the cation exchanger, although active enzyme was also found in the flow through. Fractions B3-B7 (chromatograph not shown) were active and were pooled, concentrated and subjected to size exclusion chromatography as final purification step.

In summary, using different techniques for enzyme purification, pure enzyme preparations were obtained and tested for their activity towards a standard esterase substrate, pNP-palmitate. Enzymatic activities of the purified variants are summarized below:

| | |
|---|---|
| KrCUT | 197 ± 3 U/mg |
| AmCUT | 244 ± 18 U/mg |
| Am-Kr | 174 ± 11 U/mg |
| CfCUT | 26 ± 1 U/mg |
| Cf-TP | 30 ± 2 U/mg |

The active fraction of KrCUT (Superdex™ 75) was shown to have a native molar mass of about 28 kD (deducted from its retention time, using a standard curve), showing a single band in SDS-PAGE at about 27 kD (FIG. 13A), which corresponds well with the theoretical molar mass for full length Kr (26 kD, after YebF cleavage).

AmCUT and Am—Kr behaved unusual in size exclusion chromatography, which made determining their native molar masses impossible, as the retention time of both enzymes did not correspond to their predicted molar mass. Instead, both enzymes were retained on the column, suggesting some interaction of the enzymes with the column matrix. SDS-PAGE of Am—Kr (FIG. 13B) revealed two distinct species with molar masses of about 40 kD (which is in agreement with the predicted molar mass for YebF—Am—Kr) and about 22 kD which is slightly below the predicted molar mass of full length Am—Kr (YebF removed, 26 kDa).

Example 19

Circular Dichroism Spectroscopy and Estimation of Melting Temperature (Tm)

The enzymes purified in Example 18 were characterized to determine their melting temperatures.
19.1 Methods CD spectra were recorded using a Jasco™ J-815 spectrometer operating with the Spectra™ Manager software. Temperature was controlled using a Jasco™ PFD-452S peltier unit. Previously purified protein solutions were adjusted to 0.15 mg/mL (if quantities allowed for) and CD spectra were recorded between 190 and 250 nm using a Quartz cuvette (ID=0.1 cm). Blanks containing buffer only were prepared and used as baseline. Temperature dependent protein unfolding was monitored at 222 nm with thermo profiles ranging from 20 up to 90° C. (2° C. min-1). Samples were kept for 5 min at the respective maximum temperature and protein refolding was monitored using the same conditions as above reversing the thermo profiles. Thermodynamic parameters (Tm, ΔH, ΔS, ΔG) for the folding/unfolding process, if applicable, were calculated using the Spectra™ Manager software.
19.2 Results Variable temperature measurement using CD spectroscopy (monitored at 222 nm) shows the unfolding of KrCUT with increased temperature (FIG. 14A). The melting temperature (Tm) was estimated to be 50.7° C.±0.1. KrCUT also showed refolding to some extent (FIG. 14A, upper curve, going from high to low temperature) with a midpoint transition temperature of 42.7° C.±0.2.

The Tm of Am—Kr was estimated to be 55.0° C.±0.1 (FIG. 14B). In contrast to KrCUT, Am—Kr did not show any refolding.

The Tm of CfCUT was estimated to be 65.2° C.±0.1 (FIG. 14C). CfCUT did not show any refolding.

The CD signal of Cf-TP was a slightly low, probably due to lower protein concentration. The Tm of Cf-TP was estimated to be 56.6° C.±0.1 (FIG. 14D). Cf-TP showed some refolding, but to a much lower extend when compared to KrCUT.

The CD signal of AmCUT was too weak to allow for the estimation of a Tm for this enzyme.

All enzymes showed the typical spectrum of alpha-helix dominant secondary structure, as expected being hydrolases.

Example 20

Enzyme Substrate Profiles

The enzymes purified in Example 18 were characterized to determine their substrate profiles on common esterase substrates.
20.1 Methods: Esterase Assays Esterase activity was determined by monitoring the formation of para-nitrophenol (pNP) at 410 nm from various pNP-esters using a Beckman UV spectrophotometer (model DU 640). Substrates were completely dissolved in 2-propanol (8 mM) and were then added to 50 mM Tris/HCl buffer pH 8.0 to give a final substrate concentration of 0.8 mM. The reaction (1 mL) was started by adding an appropriate amount of enzyme. One enzyme unit (U) was defined as the amount of enzyme that produced 1 μmol of product (pNP) per min; specific activity was expressed as U/mg protein. A molar extinction coefficient of 15 $mM^{-1}$ $cm^{-1}$ was used for the calculation.
20.2 Results

TABLE 11

Substrate profiles of enzymes tested

| Substrates | KrCUT | AmCUT | Am-Kr | CfCUT | Cf-TP |
|---|---|---|---|---|---|
| pNP-acetate (C2) | 2 | 8 | 9 ± 1 | 6 | 5 |
| pNP-butyrate (C4) | 26 ± 2 | 20 ± 2 | 75 ± 8 | 93 ± 8 | 80 ± 3 |
| pNP-caprylate (C8) | 25 ± 3 | 76 ± 2 | 100* | 11 ± 2 | 33 ± 1 |
| pNP-decanoate (C10) | 25 ± 3 | 80 ± 2 | 72 ± 2 | 40 ± 5 | 66 ± 8 |
| pNP-myristate (C14) | 100* | 100* | 46 ± 8 | 47 ± 8 | 40 ± 4 |
| pNP-palmitate (C16) | 98 ± 6 | 78 ± 2 | 49 ± 6 | 100* | 100* |

*Relative activities in % for the respective cutinase, highest activity towards a specific substrate set to 100%

As can be seen in Table 11, the highest enzymatic activity for KrCUT and AmCUT was achieved with pNP-myristate, whereas the CfCUT and Cf-TP variants showed the highest activity towards pNP-palmitate. In contrast, Am—Kr seemed to prefer the lower chain substrates with highest activity towards pNP-caprylate. pNP-acetate seems to be a relatively poor substrate for all variants. KrCUT, AmCUT and Am—Kr showed preference for the longer carbon chain substrates, whereas the CfCUT and Cf-TP substrate profile seemed to be more inhomogeneous, with preference for both pNP-butyrate and pNP-palmitate.

Example 21

Determination of Enzyme Optimal Temperatures and Thermostability

The enzymes purified in Example 18 were characterized to determine their optimum temperatures.
21.1 Methods: Temperature Optimum For estimation of the temperature optimum, buffer containing pNP-palmitate (see esterase assay in Example 20.1) was pre-incubated to reach the desired temperature, enzyme was then added, and the formation of pNP was assayed. For this experiment, Tris/HCl buffer was replaced with sodium phosphate buffer (50 mM, pH 8.0) to avoid a pH shift at the different temperatures.
21.2 Results: Temperature Optimum

TABLE 12

Temperature dependence of the different enzymes tested

| Temperature (° C.) | KrCUT | AmCUT | Am-Kr | CfCUT | Cf-TP |
|---|---|---|---|---|---|
| 20 | 83 ± 5 | 92 ± 11 | 50 ± 2 | 69 ± 2 | 54 ± 5 |
| 25 | 84 ± 4 | 100* | 61 ± 2 | 100* | 84 ± 9 |
| 30 | 83 ± 4 | 67 ± 3 | 69 ± 2 | 63 ± 7 | 95 ± 5 |
| 35 | 84 ± 4 | 27 ± 4 | 78 ± 1 | 45 ± 5 | 100* |
| 40 | 89 ± 6 | 15 ± 2 | 87 ± 2 | 38 ± 8 | 89 ± 6 |
| 45 | 100* | — | 100* | 1 | 72 ± 7 |
| 50 | 90 ± 4 | — | 81 ± 10 | — | 37 ± 6 |

TABLE 12-continued

Temperature dependence of the different enzymes tested

| Temperature (° C.) | KrCUT | AmCUT | Am-Kr | CfCUT | Cf-TP |
|---|---|---|---|---|---|
| 55 | 38 ± 3 | — | 37 ± 5 | — | 9 ± 1 |
| 60 | 15 ± 5 | — | 9 ± 1 | — | — |

*Relative activities in % for the respective cutinase, highest activity at a specific temperature set to 100%

As shown in the results above, the multi-domain enzyme KrCUT showed enzymatic activity at a broader range of temperatures than single-domain AmCUT and fellow multi-domain CfCUT (despite CfCUT having an higher estimated melting temperature than KrCUT, see Example 19.2). Interestingly, fusing the T/P-rich linker domain and the polymer binding domains from KrCUT to the cutinase catalytic domain of AmCUT, resulted in a chimeric enzyme (Am—Kr) having higher enzymatic activity at broader range of temperatures than AmCUT. Furthermore, replacing only the T/P-rich linker domain of CfCUT with the corresponding domain from KrCUT was sufficient to produce a chimeric enzyme (Cf-TP) having enzymatic activity at broader range of temperatures than CfCUT.

21.3 Methods: Thermostability

Enzyme thermostability was studied over a temperature range of 50-95° C. using the purified enzyme preparations. Aliquots were incubated at the desired temperature for 5, 10, 30, 60, and 120 minutes, chilled on ice, and assayed for remaining activity towards p-NP-palmitate (pNPP) at room temperature.

21.4 Results: Thermostability

TABLE 13

Thermostability of the cutinase variants is shown in the following table and graphs.

| Time (min) | 50° C. | 55° C. | 60° C. | 65° C. | 70° C. |
|---|---|---|---|---|---|
| KrCUT* | | | | | |
| 5 | 61 ± 5 | 45 ± 4 | 34 ± 4 | 19 ± 2 | — |
| 10 | 31 ± 4 | 26 ± 4 | 12 ± 2 | — | — |
| 30 | 12 ± 2 | 4 | — | — | — |
| 60 | 6 | — | — | — | — |
| 120 | — | — | — | — | — |
| AmCUT* | | | | | |
| 5 | 46 ± 6 | 21 ± 4 | 3 | — | — |
| 10 | 18 ± 3 | 10 ± 2 | — | — | — |
| 30 | 5 | — | — | — | — |
| 60 | — | — | — | — | — |
| 120 | — | — | — | — | — |
| Am-Kr* | | | | | |
| 5 | 96 ± 3 | 82 ± 17 | 19 ± 2 | 12 ± 1 | — |
| 10 | 85 ± 8 | 64 ± 3 | 15 ± 2 | — | — |
| 30 | 75 ± 15 | 56 ± 8 | 5 ± 1 | — | — |
| 60 | 79 ± 12 | 42 ± 8 | — | — | — |
| 120 | 80 ± 9 | 30 ± 3 | — | — | — |
| cfCUT* | | | | | |
| 5 | 109 ± 3 | 72 ± 7 | 70 ± 6 | 65 ± 5 | 40 ± 5 |
| 10 | 118 ± 3 | 75 ± 10 | 75 ± 7 | 64 ± 4 | 37 ± 6 |
| 30 | 129 ± 9 | 77 ± 9 | 56 ± 10 | 55 ± 1 | 33 ± 3 |
| 60 | 120 ± 6 | 65 ± 10 | 40 ± 4 | 30 ± 5 | 26 ± 3 |
| 120 | 125 ± 20 | 58 ± 2 | 28 ± 4 | 25 ± 4 | 15 ± 1 |
| Cf-TP* | | | | | |
| 5 | 68 ± 8 | 42 ± 4 | 35 ± 3 | 31 ± 3 | — |
| 10 | 43 ± 3 | — | — | — | — |
| 30 | 42 ± 3 | 31 ± 1 | 30 ± 3 | 25 ± 3 | — |
| 60 | — | — | 22 ± 4 | 15 ± 2 | — |
| 120 | — | 21 ± 3 | 15 ± 3 | 9 ± 2 | — |

*Relative activities in % for the respective cutinase, activity set to 100% at time 0.

The results above show that single-domain enzyme AmCUT seemed to be very unstable at higher temperatures, whereas all the multi-domain enzymes (particularly the CfCUT) showed higher thermostability. The letter variant was also shown to have the highest melting temperature, however, the optimal temperature does not seem to reflect the enzyme's higher thermostability.

Example 22

Enzymatic Activity in the Presence of Organic Solvents

The enzymes purified in Example 18 were characterized to determine their stability and activity in presence of diverse organic solvents.

22.1 Methods

Enzyme activity in various organic solvents was studied over a concentration range of 1-30% at room temperature. pNP-palmitate was completely dissolved in 2-propanol (8 mM) and then added to 50 mM Tris/HCl buffer pH 8.0 containing up to 30% organic solvent to give a final substrate concentration of 0.8 mM. The reaction was started by addition of enzyme and the formation of pNP was assayed as described above in Example 20.1.

22.2 Results

TABLE 14

Enzymatic activity in the presence of organic solvents

| Solvent addition to assay | Solvent conc. (v/v) | Relative enzymatic activity (%) | | | | |
|---|---|---|---|---|---|---|
| | | KrCUT | AmCUT | Am-Kr | CfCUT | Cf-TP |
| Buffer only | | 100* | 100* | 100* | 100* | 100* |
| Methanol | 10% | 91 ± 12 | 116 ± 4 | 87 ± 10 | 115 ± 11 | 121 ± 14 |
| | 20% | 8 | 16 ± 2 | 60 ± 13 | 62 ± 3 | 94 ± 1 |
| 2-Propanol | 5% | 55 ± 11 | 60 ± 2 | 70 ± 10 | 70 ± 3 | 93 ± 1 |
| | 10% | 8 | 9 ± 2 | 23 ± 2 | 17 ± 8 | 92 ± 2 |
| Dimethyl sulfoxide (DMSO) | 10% | 106 ± 4 | 142 ± 12 | 114 ± 2 | 105 ± 11 | 150 ± 14 |
| | 20% | 14 ± 2 | 53 ± 2 | 90 ± 8 | 107 ± 1 | 146 ± 23 |
| | 30% | 2 | 7 ± 2 | 60 ± 5 | 57 ± 15 | 129 ± 18 |
| Dimethylformamide (DMF) | 5% | 55 ± 11 | 149 ± 7 | 120 ± 11 | 101 ± 17 | 134 ± 10 |

TABLE 14-continued

Enzymatic activity in the presence of organic solvents

| Solvent addition to assay | Solvent conc. (v/v) | Relative enzymatic activity (%) | | | | |
|---|---|---|---|---|---|---|
| | | KrCUT | AmCUT | Am-Kr | CfCUT | Cf-TP |
| Acetone | 1% | 71 ± 2 | 170 ± 2 | 118 ± 1 | 92 ± 9 | 103 ± 12 |
| | 5% | 47 ± 7 | 126 ± 5 | 90 ± 14 | 95 ± 1 | 112 ± 10 |
| | 10% | — | 26 ± 7 | 74 ± 7 | 52 ± 5 | 109 ± 6 |

*Relative activities in % for the respective cutinase, activity with buffer only as negative control set to 100%

The results above show that the chimeric enzymes Am—Kr and Cf-TP impressively exhibited increased tolerance to higher concentrations of most of the organic solvents tested. More particularly, the chimeric Am—Kr enzymes exhibited higher relative activity in the presence of methanol (20% v/v), 2-propanol (10% v/v), dimethyl sulfoxide (DMSO; 20% or 30% v/v), and acetone (10% v/v), as compared to its corresponding wild-type enzymes (KrCUT and AmCUT). Similarly, the chimeric Cf-TP enzyme exhibited higher relative activity in the presence of all the organic solvents tested, as compared to its corresponding wild-type enzymes (KrCUT and CfCUT).

Example 23 pH Dependence of Enzymes

The enzymes purified in Example 18 were characterized to determine their stability and activity at different pHs.

23.1 Methods: pH Optimum

The influence of different pH values (from 5.5 to 11) on the activities of the purified enzymes was examined in three buffer systems (sodium acetate, sodium phosphate, and Tris-HCl) at room temperature using pNP-palmitate (see esterase assay in Example 20.1) as a substrate at a final substrate concentration of 0.8 mM.

23.2 Results

TABLE 15 pH dependence of each of the enzymes

| | Relative activity (%) | | | | |
|---|---|---|---|---|---|
| pH | KrCUT | AmCUT | Am-Kr | CfCUT | Cf-TP |
| 6.5 | 22 ± 1 | 35 ± 6 | 23 ± 2 | 13 ± 2 | 12 ± 1 |
| 7.0 | 53 ± 2 | 56 ± 6 | 46 ± 3 | 40 ± 4 | 22 ± 1 |
| 7.5 | 72 ± 4 | 56 ± 2 | 54 ± 3 | 65 ± 5 | 36 ± 1 |
| 8.0 | 87 ± 6 | 38 ± 8 | 84 ± 2 | 62 ± 2 | 65 ± 7 |
| 8.5 | 100* | 69 ± 4 | 88 ± 9 | 85 ± 6 | 88 ± 8 |
| 9.0 | 96 ± 4 | 94 ± 4 | 91 ± 5 | 93 ± 9 | 95 ± 3 |
| 9.5 | 76 ± 7 | 100* | 100* | 100* | 100* |
| 10 | 37 ± 5 | 73 ± 2 | 47 ± 4 | 31 ± 1 | 35 ± 4 |
| 10.5 | — | 60 ± 2 | 10 ± 1 | — | — |

*Relative activities in % for the respective cutinase, highest activity at a specific pH set to 100%, sodium phosphate buffer (6.5-7.5), Tris/HCl (8.0-10.5)

Example 24

Stability of Enzymes Towards Oxidizing Agent

The enzymes purified in Example 18 were characterized to determine their stability and activity after being exposed to an oxidizing agent (i.e., hydrogen peroxide).

24.1 Methods: Stability in the Presence of Hydrogen Peroxide

Purified cutinases were incubated at room temperature in the presence of 0, 30, 100, 300, 1500, and 3000 ppm of hydrogen peroxide. Residual enzyme activity was assayed (see Example 20.1) after 1, 2, 3, and 7 days of incubation.

24.1 Results

TABLE 16

Enzyme stability following exposure to hydrogen peroxide

| | Relative activity (%) | | | | |
|---|---|---|---|---|---|
| $H_2O_2$ (ppm) | Day 0 | Day 1 | Day 2 | Day 3 | Day 7 |
| KrCUT* | | | | | |
| 30 | 100 ± 9 | 90 ± 6 | 75 ± 3 | 75 ± 8 | 76 ± 2 |
| 100 | 104 ± 6 | 91 ± 6 | 88 ± 6 | 76 ± 2 | 66 ± 2 |
| 300 | 102 ± 4 | 87 ± 2 | 74 ± 1 | 63 ± 2 | 49 ± 4 |
| 1,500 | 102 ± 10 | 80 ± 4 | 67 ± 4 | 44 ± 2 | 11 ± 1 |
| 3,000 | 98 ± 9 | 60 ± 2 | 33 ± 1 | 20 ± 4 | — |
| AmCUT* | | | | | |
| 30 | 94 ± 6 | — | — | — | — |
| 100 | 94 ± 6 | — | — | — | — |
| 300 | 85 ± 12 | — | — | — | — |
| 1,500 | 65 ± 6 | — | — | — | — |
| 3,000 | 44 ± 10 | — | — | — | — |
| Am-Kr* | | | | | |
| 30 | 92 ± 3 | 90 ± 15 | 82 ± 8 | 71 ± 4 | 63 ± 5 |
| 100 | 101 ± 3 | 97 ± 5 | 83 ± 2 | 73 ± 5 | 69 ± 4 |
| 300 | 100 ± 9 | 88 ± 5 | 83 ± 2 | 72 ± 10 | 61 ± 4 |
| 1,500 | 91 ± 8 | 97 ± 9 | 75 ± 15 | 73 ± 3 | 60 ± 6 |
| 3,000 | 86 ± 6 | 68 ± 9 | 63 ± 4 | 67 ± 2 | 55 ± 3 |
| CfCUT* | | | | | |
| 30 | 101 ± 22 | 89 ± 8 | 82 ± 8 | 76 ± 6 | 72 ± 7 |
| 100 | 92 ± 5 | 114 ± 15 | 118 ± 15 | 92 ± 11 | 94 ± 7 |
| 300 | 93 ± 12 | 106 ± 20 | 118 ± 12 | 102 ± 14 | 106 ± 13 |
| 1,500 | 126 ± 1 | 106 ± 12 | 109 ± 2 | 95 ± 4 | 54 ± 16 |
| 3,000 | 128 ± 18 | 115 ± 2 | 99 ± 23 | 60 ± 6 | 35 ± 1 |
| Cf-TP* | | | | | |
| 30 | 97 ± 1 | 89 ± 4 | 78 ± 3 | 86 ± 2 | 65 ± 7 |
| 100 | 98 ± 6 | 91 ± 3 | 89 ± 7 | 94 ± 7 | 74 ± 6 |
| 300 | 95 ± 6 | 88 ± 3 | 85 ± 12 | 98 ± 3 | 77 ± 5 |
| 1,500 | 95 ± 9 | 89 ± 3 | 88 ± 6 | 87 ± 4 | 68 ± 7 |
| 3,000 | 80 ± 2 | 74 ± 5 | 77 ± 2 | 78 ± 5 | 57 ± 5 |

*Relative activities in % for the respective cutinase, activity with buffer only as negative control set to 100% at day 0.

As shown above, all of the multi-domain enzymes that were tested (i.e., KrCUT, Kr-Am, CfCUT, and Cf-TP) retained some level of activity after 1 or more days exposure to hydrogen peroxide, whereas the single-domain enzyme AmCUT did not. Furthermore, chimeric enzymes (Kr-Am and Cf-TP) exhibited increased resistance to hydrogen peroxide, as compared to their corresponding wild-type multi-domain enzymes (KrCUT and CfCUT). For example, after exposure to 3000 ppm hydrogen peroxide for 7 days, no activity was detected for the wild-type KrCUT enzyme. In contrast, the chimeric enzyme Am—Kr (containing the cutinase catalytic domain of AmCUT on the backbone of KrCUT), retained 55% of its activity under the same conditions. Moreover, the relative activity of CfCUT was reduced from 128% at day 0 to 35% at day 7 of exposure to 3000 ppm hydrogen peroxide. In contrast, the relative activity of the chimeric enzyme Cf-TP (containing the T/P-rich linker domain of KrCUT on the backbone of CfCUT) went from 80% to 57% under the same conditions.

Example 25

Summary of Biochemical Properties of the Enzymes

A summary of some of the results shown in Examples 19-24 is provided below.

TABLE 17

Summary of biochemical properties of the tested enzymes

| Enzyme | Mol. Mass (native)[1] | Mol. Mass (SDS) | Temp. opt. (° C.) | pH opt. | Spec. Act. (U/mg)[2] | Tm (° C.)[3] |
|---|---|---|---|---|---|---|
| KrCUT | 28,000 | 27,000 | 45 | 8.5 | 197 ± 3 | 51 ± 1 |
| AmCUT | n.a.[4] | 20,000 | 25 | 9.5 | 244 ± 18 | n.d.[5] |
| Am-Kr | n.a.[5] | 22,000 | 45 | 9.5 | 174 ± 11 | 55 ± 1 |
| CfCUT[6] | 53,000 | 27,000 | 25 | 9.5 | 26 ± 1 | 65 ± 1 |
| Cf-TP[7] | 42,000 | 25,000 | 35 | 9.5 | 30 ± 2 | 57 ± 1 |

[1]Estimated by retention time of the active fraction on Superdex ™ 75 pg using a standard curve
[2]Towards pNP-palmitate (standard assay)
[3]Melting temperature of the enzyme, estimated using CD-spectroscopy
[4]Not applicable, Am and Am-Kr showed some interaction with the resin and thus a delayed retention time
[5]Not determined, Am concentration was too low to give a good signal in CD spectroscopy
[6]Cf shows a higher molecular mass native than in SDS-PAGE, which may be due to dimer formation
[7]Cf-TP showed more than one band in SDS-PAGE: 25,000 and 28,000 Da.

Example 26

Assessment of Ochratoxin A Degradation Ability by the Enzymes

The enzymes purified in Example 18 were tested for their ability to degrade the mycotoxin Ochratoxin A. In general, the mycotoxin was incubated with different concentrations of the enzyme, and the remaining mycotoxin concentration, as well the respective degradation products, were monitored by LC-MS over time (where possible/applicable).

26.1 Methods: Mycotoxin Testing

Reactions were performed in 1 mL volumes in glass HPLC vials comprising the mycotoxin to be analyzed and the enzyme to be tested. For Ochratoxin A (*Petromyces albertensis*, 01877 Sigma), 50 μL of a 100 ppm stock solution in methanol (final concentration of 5 ppm) was added to 910 μL of distilled water and 40 μL of the enzyme to be tested. In control reactions, the volume of enzyme was substituted with distilled water. The reactions were incubated in an Eppendorf thermomixer at 37° C. with shaking at 750 rpm. 100 μL samples were withdrawn at 1, 4 and 24 h for chromatographic analysis.

Mycotoxin analysis was carried out using a Shimadzu LCMS-2020 equipped with a UV/vis detector. Chromatographic separation of 10 μL injected sample was carried out at 30° C. on a Kinetex 2.6 μm XB-C18 column 100 Å (50×2.1 mm) using a binary gradient. For Ochratoxin A, eluent A consisted of water and eluent B consisted of acetonitrile and the UV detection wavelength was 360 nm. Gradient elution at a flow rate of 0.4 mL/min was performed as follows: 0-2 min, 10% B; 2.01-10.0 min, 10 to 80% B; 10.01-12.0 min, 80% B; 12.01-15 min, 10% B. The electrospray interface (ESI) was operated simultaneously in positive and negative mode, scanning from m/z 50-1,000.

26.2 Results

The degradation of Ochratoxin A was monitored by HPLC-UV at 360 nm and LCMS. Possible degradation products that would arise from either hydrolysis of the amide bond or hydrolysis of the lactone moiety are shown below.

Chemical Structures of Ochratoxin A and Hypothetical Degradation Products

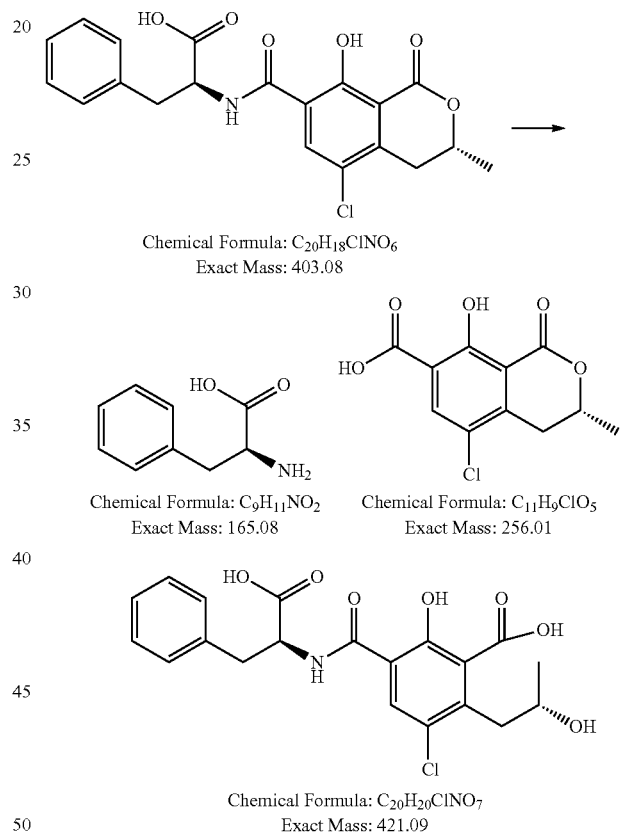

The five enzymes tested were screened for their ability to degrade 5 ppm (5,000 ppb) Ochratoxin A at 37° C. The results are summarized in Table 18.

TABLE 18

Results of Enzyme testing for Ochratoxin A degradation

| Enzyme | Activity (U)[1] | Residual ochratoxin A (%)[2] | | | Ochratoxin A Degradation[3] per U and h (μmol) |
|---|---|---|---|---|---|
| | | 1 h | 4 h | 24 h | |
| KrCUT | 3.272 | 63 | 17 | 7 | 0.02 |
| Am-Kr | 0.072 | 6 | 0 | 0 | 3 |
| AmCUT | 0.048 | 59 | 20 | 6 | 2 |

TABLE 18-continued

Results of Enzyme testing for Ochratoxin A degradation

| Enzyme | Activity (U)[1] | Residual ochratoxin A (%)[2] | | | Ochratoxin A Degradation[3] per U and h (μmol) |
|---|---|---|---|---|---|
| | | 1 h | 4 h | 24 h | |
| CfCUT | 0.056 | 11 | 2 | 0 | 3 |
| Cf-TP | 0.002 | 5 | 0 | 0 | 98 |

[1]Activity used in assay towards p-nitrophenyl palmitate (standard assay)
[2]Relative to Ochratoxin A incubated without enzyme
[3]Describes the potency of 1 U of enzyme (pNP standard test) to degrade a specific amount of ochratoxin per hour of incubation at 37° C.

Degradation of Ochratoxin A was observed with all enzymes, even after 1 h incubation. The chimeric enzymes AM-Kr and Cf-TP degraded 94-95% of the Ochratoxin A after 1 hours, and 100% after 4 hours. Cf-TP showed the highest "potency" in terms of the amount of Ochratoxin A that 1 U the enzyme (pNP standard test) can degrade per hour of incubation at 37° C.

Example 27

Alignment and Phylogenic Analyses of Multi-Domain Cutinase Enzymes

A database search for other multi-domain enzymes using KrCUT (SEQ ID NO: 6) as query sequence revealed five hits, as shown in Table 19.

TABLE 19

Native cutinase orthologs having multi-domain organization

| Enzyme name | Organism | Query coverage | Identity | Accession | SEQ ID NO: |
|---|---|---|---|---|---|
| ssKrCUT | Kineococcus radiotolerans SRS30216 = ATCC BAA-149 | 100% | 100% | ABS05574.1 | 1 |
| ssCbCUT2 | Cellulomonas bogoriensis 69B4 = DSM 16987 | 95% | 60% | KGM14008.1 | 25 |
| ssCcCUT | Cellulomonas cellasea DSM 20118 | 98% | 56% | KGM03336.1 | 15 |
| ssCbCUT1 | Cellulomonas bogoriensis 69B4 = DSM 16987 | 99% | 55% | KGM14009.1 | 14 |
| ssCfCUT | Cellulomonas flavigena DSM 20109 | 99% | 56% | ADG75999.1 | 13 |

A multiple sequence alignment was performed for the enzymes listed in Table 19, after omitting their predicted N-terminal signal sequences, as shown in Table 20. The results of the alignment are shown in FIG. 15A, and a phylogenic tree is shown in FIG. 15B.

TABLE 20

KrCUT orthologs without their predicted N-terminal signal sequences

| Enzyme name | Amino acid sequence (cutinase catalytic domains are in bold; linkers are *italicized*; polymer binding domains are underlined) | SEQ ID NO: |
|---|---|---|
| KrCUT | ATCSDVDVVFARGTGETPGLGVVGGPFVRSLTGELSDRTVTSHA VDYAASSSQASAGPGATAMSAHVREVAAACPSTRFVLGGYSQGA TVTDIALGIRTGTTTGTPVPAELAGRVAAVVVFGNPLGLSGRTI ATASSTYGPKSKDYCNSSDSVCGSAPKTGTGGHLSYASNGSTTD GARFAAGLVRAAG*TPTTPTPTPTPVPTT*<u>CVRDSTRDHVAADR AVSLYGRAYARGSRDSLGATSSYNVVSLQQVEGGWRLVTAC</u> | 6 |
| CbCUT2 | AGSCPDVQVVFARGTGERAGLGIIGRPFARALADELPGMTVTSH AVDYAAAASQRSAGPGATAMTDHVTAMAARCPGTQFVLGGYSQG ATVTSIALGIRAGTTTGRAIPDELSDRVAAVVVFGNPLGMRGQT IASASRTYADRAKDYCNSGDSICGRQPSTGRGTHTGYATNGSTT DGARFAAGLVTA*NPPEAAPPTAPPTTPPTTPAPP*<u>SDQVTCVTAQ VSEHVEARRAIRGLTRAYARGTLEDIGRLRSTEEVSLRRSGTFS WTPTASC</u> | 46 |
| CcCUT | APACADVEVLFARGTGEAPGLGVLGTPFVRSVTSALSDRTVTSY AVNYAAESSQRSAGPGATDLTNHLTATAAACPGTRFVLGGYSQG ATVVDLALGIRTGTTTGTAIPAALEPRVAAIVVFGNPLGISGRT IATASPTYAARARDFCATGDPVCGGGSSFAAHLAYRTNGDVTAG ADFAAGLARA*TTVPVPTPTVPGTPTPSPTAPGTPTPVPTTSPTP APSPTAPG*<u>AACVRASTRAHVEAGRAERRHGIAYATGSGDRIGWV SSFVRVSVQQTADGWERVLSC</u> | 47 |
| CbCUT1 | TGDCPDVHVVFARGTGEPRGLGIVGRPFVSDLGDALPTMTVTSY AVNYSANASQTSAGPGAGDMTSHVTSMAARCPGTQFVLGGYSQG ATVTSIAVGARSTSIRSRVLPANLEPRVAAVVVFGNPLGLTRRT | 48 |

TABLE 20-continued

KrCUT orthologs without their predicted
N-terminal signal sequences

| Enzyme name | Amino acid sequence (cutinase catalytic domains are in bold; linkers are *italicized*; polymer binding domains are <u>underlined</u>) | SEQ ID NO: |
|---|---|---|
| | IASEAPAYAAKSRDYCNRSDTVCGGRGDARGGHLAYVSNGSVAD GAAFAA*SLVGVAPGDPAS*CVTARAVDHVEADRAFRSVLRAYARG SRDPLGRLTSSDLVSLQRTGQDSWSVVPAC | |
| CfCUT | APACPDVELVFARGTGEAAGLGIVGRPLERALAAELPGRTVVAT AVDYAASSSQASAGPGSGDMVAKVRSRAAACPGTQFVLGGYSQG ATVTDLALGIRTGVTAGTALPEDLAARVAAVVVYGNPLGLTRRT IAQAAPAFATRTVEYCNAGDPVCEPGGGRFTAHITYATNGTVLE GARFAAARVTA*PAPTPTPGPTGTPAPVPSAEPTPAPGDT*<u>CVTAS SLQHVRDGRAYPLWMRTYARGSGDPLGVLSSRTVVSLQADGTDT WRKVAAC</u> | 28 |

The threonine/proline contents of the T/P-rich linker domains of four of the enzymes listed above are shown in Table 21.

TABLE 21

Threonine/proline content of selected multi-domain cutinases

| Enzyme name | Amino acid sequence of T/P-rich linker | SEQ ID NO: | # of T or P residues | Linker length | T/P content |
|---|---|---|---|---|---|
| KrCUT | TPTTPTPTPTPTPVPTT | 3 | 16 | 17 | 94.1% |
| CbCUT2 | NPPEAAPPTAPPTTPPTTPAPP | 37 | 16 | 22 | 72.7% |
| CcCUT | GLARATTVPVPTPTVPGTPTPSP TAPGTPTPVPTTSPTPAPSPTAP GAA | 40 | 17 | 28 | 60.7% |
| CfCUT | PAPTPTPGPTGTPAPVPSAEPTP APGDT | 31 | 29 | 49 | 59% |

The present description refers to a number of documents, the content of which is herein incorporated by reference in their entirety.

The scope of the claims should not be limited by the preferred embodiments set forth in the examples, but should be given the broadest interpretation consistent with the description as a whole.

REFERENCES

Bligh, E. G. and W. J. Dyer. 1959. A rapid method for total lipid extraction and purification. Can. J. Biochem. Physiol. 37:911-917.

Copeland A., S. Lucas, A. Lapidus, K. Barry, T. Glavina del Rio, N. Hammon, S. Israni, E. Dalin, H. Tice, S. Pitluck, E. Saunders, T. Brettin, D. Bruce, J. C. Detter, C. Han, J. Schmutz, F. Larimer, M. Land, L. Hauser, N. Kyrpides, A. Lykidis, C. E. Bagwell, L. Shimkets, C. J. Berry, C. Fliermans, and P. Richardson. 2007. Complete sequence of chromosome of *Kineococcus radiotolerans* SRS30216. EMBL/GenBank/DDBJ databases Gerard, H. C., W. F. Fett, S. F. Osamn, and R. A. Moreau. 1993. Evaluation of cutinase activity of various industrial lipases. Biotechnol. Appl. Biochem. 17:181-189.

Kallio, H., R. Nieminen, S. Tuomasjukkas, and M. Hakala. 2006. Cutin composition of five finnish berries. J. Agric. Food Chem. 54: 457-462.

Kasuya, K., T. Ohura, K. Masuda, and Y. Doi. 1999. Substrate and binding specificities of bacterial polyhydroxybutyrate depolymerases. Int. J. Biol. Macromol. 24: 329-336.

Kim, Y.-H., J. Lee, and S.-H. Moon. 2003. Uniqueness of microbial cutinases in hydrolysis of p-nitrophenyl esters. J. Microbiol. Biotechnol. 13:57-63.

Martinez, C., P. de Geus, M. Lauwereys, G. Matthyssens, and C. Cambillau. 1992. *Fusarium solani* cutinase is a lipolytic enzyme with a catalytic serine accessible to solvent. Nature 356:615-618.

Phillips, R. W., J. Wiegel, C. J. Berry, C. Fliermans, A. D. Peacock, D. C. White, and L. J. Shimkets. 2002. *Kineococcus radiotolerans* sp. nov., a radiation-resistant, Gram-positive bacterium. Int. J. System. Evol. Biol. 52:933-938.

Rudrabhatla, M., George, J. E, & Faye, T. (2007). Multi-componentmycotoxin analysis by LC/MS/MS. The 10th annual meeting of the Israel analytical chemistry society conference and exhibition; Israel Analytical Chemistry Society.

Sambrook J, E. F. Fritsch and T. Maniatis. 1989. Molecular Cloning: A Laboratory Manual, 2nd edn. Cold Spring Harbor Laboratory Press, Cold Spring Harbor, N.Y.

Soliday, C. L., W. H. Flurkey, T. W. Okita, and P. E. Kolattukudy. 1984. Cloning and structure determination of cDNA for cutinase, an enzyme involved in fungal penetration of plants. Proc. Natl. Acad. Sci. USA. 81:3939-3943.

Smith, P. K., R. I. Krohn, G. T. Hermanson, A. K. Mallia, F. H. Gartner, E. K. Provenzano, E. K. Fujimoto, N. M. Goeke, B. J. Olson, and D. C. Klenk. 1985. Measurement of protein using bicinchoninic acid. Analyt. Biochem. 150:76-85.

Surinenaite et al., Biotechnol Appl Biochem. 2002 August; 36(Pt 1):47-55.

Tamura, K., J. Dudley, M. Nei, and S. Kumar. 2007. MEGA4: Molecular Evolutionary Genetics Analysis (MEGA) software version 4.0. Mol. Biol. Evol. 24:1596-1599.

Wang, P., L. Cui, Q. Wang, X. Fan, X. Zhao, and J. Wu. 2010. Combined use of mild oxidation and cutinase/lipase pretreatments for enzymatic processing of wool fabrics. Eng. Life. Sci. 10:19-25.

Xiao, Z., H. Bergeron, S. Grosse, M. Beauchemin, M.-L. Garron, D. Shaya, T. Sulea, M. Cygler, and P. C. K. Lau. 2008. Improvement of the thermostability and activity of a pectate lyase by single amino acid substitutions, using a strategy based on melting-temperature-guided sequence alignment. Appl. Environ. Microbiol. 74:1183-1189.

Zhang, G., S. Brokx, and J. H. Weiner. 2006. Extracellular accumulation of recombinant proteins fused to the carrier protein YebF in *Escherichia coli*. Nat. Biotechnol. 24:100-104.

What is claimed is:

1. An isolated chimeric recombinant protein having cutinase activity, said protein comprising a cutinase catalytic domain and a polymer binding domain operably linked by a proline/threonine-rich linker domain, wherein the proline/threonine-rich linker domain comprises at least 85% proline or threonine residues over a stretch of at least 17 consecutive amino acids, or comprises an amino acid sequence at least 85% identical to SEP ID NO: 3.

2. The isolated chimeric recombinant protein of claim 1, wherein the proline/threonine-rich linker domain comprises at least 90% proline or threonine residues over a stretch of at least 17 consecutive amino acids, or comprises an amino acid sequence at least 90% identical to SEQ ID NO: 3.

3. The isolated chimeric recombinant protein of claim 1, wherein at least two of the cutinase catalytic domain, the polymer binding domain, and the proline/threonine-rich linker domain originate from native enzymes of different species.

4. The isolated chimeric recombinant protein of claim 3, wherein the polymer binding domain and the proline/threonine-rich linker domain are selected from a multi-domain cutinase from the species *Kineococcus radiotolerans, Cellulomonas flavigena, Cellulomonas bogoriensis*, and *Cellulomonas cellasea*.

5. The isolated chimeric recombinant protein of claim 3, wherein the polymer binding domain is from a poly(3-hydroxybutyrate) (PHB) depolymerase of the species *Paucimonas lemoignei, Thermobifida* sp. BCC23166, *Comamonas testosterone, Thermobifida fusca*, or *Nocardiopsis dassonvillei*.

6. The isolated chimeric recombinant protein of claim 1, which is recombinantly produced fused to a heterologous carrier protein or heterologous tag that enables secretion of said recombinant protein, and/or facilitates purification or detection of said recombinant protein.

7. The isolated chimeric recombinant protein of claim 6, wherein said carrier protein is YebF.

8. A composition comprising:
 (i) an isolated recombinant protein having cutinase activity, said protein comprising a cutinase catalytic domain and a polymer binding domain operably linked by a proline/threonine-rich linker domain, wherein the proline/threonine-rich linker domain comprises at least 85% proline or threonine residues over a stretch of at least 17 consecutive amino acids, or comprises an amino acid sequence at least 85% identical to SEQ ID NO: 3; and
 (ii) a bleaching agent and/or an organic solvent,
 wherein said recombinant protein retains said cutinase activity when present in said composition, and
 wherein the composition is: a cleaning product, a degreaser, a disinfectant, a bleaching product, a product for controlling biofilm, or any combination thereof; feed or a feed additive;
a product for inactivating mycotoxin; a product for bioscouring or other treatment of fabrics or textiles; a product for catalyzing trans-esterification reactions; a product for vegetable oil extraction; or a product for enhancing oil recovery.

9. The composition of claim 8 comprising a bleaching agent which is: hydrogen peroxide, a peroxide other than hydrogen peroxide, a non-peroxide oxidizing agent, ozone, sodium percarbonate, sodium perborate, and any combination thereof.

10. The composition of claim 8 comprising a peroxide.

11. The composition of claim 8 comprising a bleaching agent which is: sodium dithionite, sodium dithionite, sulfur dioxide, a sulfite, a bisulfite, a sodium borohydride, or any combination thereof.

12. The composition of claim 8 comprising an organic solvent which is: methanol, 2-propanol, or an alcohol other than methanol or 2-propanol, dimethyl sulfoxide (DMSO), dimethylformamide (DMF), or acetone.

13. The composition of claim 8 having a pH between 7.5 and 9.5.

14. The composition of claim 8, further comprising: a detergent, a surfactant, a buffer, a chelator, or any combination thereof.

15. The composition of claim 8, further comprising a chelator which is EDTA or GLDA.

16. The composition of claim 8, further comprising a polyol and/or boric acid as a stabilizer.

17. The composition of claim 8, further comprising an additional recombinant enzyme which is: a lipase, an esterase, a pectate lyase, a pectinase, a cutinase, a cellulase, a hemicellulose, an amylase, or any combination thereof.

18. The composition of claim 8, wherein the proline/threonine-rich linker domain comprises at least 90% proline or threonine residues over a stretch of at least 17 consecutive amino acids, or comprises an amino acid sequence at least 90% identical to SEQ ID NO: 3.

19. The composition of claim 8, wherein at least two of the cutinase catalytic domain, the polymer binding domain, and the proline/threonine-rich linker domain originate from native enzymes of different species.

20. The composition of claim 8, wherein:
 (a) the proline/threonine-rich linker domain is selected from a multi-domain cutinase from the species *Kineococcus radiotolerans, Cellulomonas flavigena, Cellulomonas bogoriensis*, and *Cellulomonas cellasea*; or
 (b) the polymer binding domain is selected from a multi-domain cutinase from the species *Kineococcus radiotolerans, Cellulomonas flavigena, Cellulomonas bogoriensis*, and *Cellulomonas cellasea*; or
 from a poly(3-hydroxybutyrate) (PHB) depolymerase of the species *Paucimonas lemoignei, Thermobifida* sp. BCC23166, *Comamonas testosterone, Thermobifida fusca*, and *Nocardiopsis dassonvillei*.

\* \* \* \* \*